(12) United States Patent
Donaldson et al.

(10) Patent No.: US 6,444,878 B1
(45) Date of Patent: Sep. 3, 2002

(54) METHOD OF PLANT SELECTION USING GLUCOSAMINE-6-PHOSPHATE DEAMINASE

(75) Inventors: Iain A. Donaldson, Tinglev; Kirsten Bojsen, Allerod; Kirsten Jorgensen, Guldborg; Morten Jorsboe, Nykobing Falster, all of (DK)

(73) Assignee: Danisco A/S, Copenhagen (DK)

( * ) Notice: Subject to any disclaimer, the term of this patent is extended or adjusted under 35 U.S.C. 154(b) by 0 days.

(21) Appl. No.: 09/367,293

(22) PCT Filed: Feb. 5, 1998

(86) PCT No.: PCT/GB98/00367
§ 371 (c)(1),
(2), (4) Date: Dec. 23, 1999

(87) PCT Pub. No.: WO98/35047
PCT Pub. Date: Aug. 13, 1998

(30) Foreign Application Priority Data

Feb. 7, 1997 (GB) .............................................. 9702592

(51) Int. Cl.$^7$ ........................... C12N 15/82; C12N 5/04; C12N 15/31; C12N 15/09; A01H 5/00
(52) U.S. Cl. .................... 800/300; 800/288; 800/317.2; 800/320.1; 800/278; 435/418; 435/419; 435/320.1; 435/468; 536/23.2; 536/23.7
(58) Field of Search ................................ 435/410, 419, 435/440, 455, 468, 471, 418, 320.1; 536/23.1, 23.2, 23.7; 800/317.2, 320.1, 278, 284, 288, 300

(56) References Cited

FOREIGN PATENT DOCUMENTS

| WO | WO93/05263 | 3/1993 |
| WO | WO93/06220 | 4/1993 |
| WO | WO94/20627 | 9/1994 |
| WO | WO96/31612 | 10/1996 |

OTHER PUBLICATIONS

Rogers et al. Nucleotide sequences of the *Escherichia colia* and nagE and nagB genes: the strucutral genes for . . . for glucosamine–6–phosphate deaminase. Gene 62:197–207. 1988.*

Vancanneyt et al. Construction of an intron–containing marker gene: Splicing of the intron intransgenic plants and its use in monitoring early events in Agrobacterium–mediated plant transformation. Mol. Gen. Genet. 220:245–250, 1990.*

Yuan et al. Modification of plant components. Current Opinion in Biotechnology 8(2):227–233, 1997.*

Johansen, Elisabeth; Proc.Natl.Acad.Sci. USA;vol. 93, pp. 12400–12405; Oct. 1996; Genetics; Intron Insertion Facilitates Amplificatino of Cloned Virus cDNA in *Escherichia coli* While Biological Activity is Reestablished After Transcription in Vivo.

* cited by examiner

*Primary Examiner*—David T. Fox
*Assistant Examiner*—David H Kruse
(74) *Attorney, Agent, or Firm*—Knobbe, Martens, Olson & Bear, LLP

(57) ABSTRACT

A selection method for selecting from a population of plant cells one or more genetically transformed plant cells is described. In the method, the population of plant cells includes selectable genetically transformed plant cells and possible non-transformed plant cells. Each of the selectable genetically transformed plant cells comprises a first expressible nucleotide sequence and optionally a second expressible nucleotide sequence. In the method, a component or a metabolic derivative thereof when present in a low concentration in a medium is a nutrient for both the selectable genetically transformed plant cells and the non-transformed plant cells. In the method, the component or the metabolic derivative thereof when present in a high concentration in a medium is toxic to the non-transformed plant cells. The first nucleotide sequence codes for a gene product having glucosamine-6-phosphate deaminase activity which is capable of converting the component or the metabolic derivative thereof when present in a high concentration in a medium to a nutrient for the selectable genetically transformed plant cells. The method includes the step of introducing the population of plant cells to a medium, wherein the medium includes a high concentration of the component or the metabolic derivative thereof. In the method, the component or the metabolic derivative thereof is a source of both carbohydrate and nitrogen for the selectable genetically transformed plant cells.

25 Claims, 28 Drawing Sheets

```
              10        20        30        40        50
NAG1   MRQAIFSNPNDAAEYLANYIIAKIN----STPRTFVLGLPTGSSPEGIYAKLIEANKQGR
       ::          ..:.....::      .. :.::::::::..: ...: :.: .:.:.
NAG3   MRLIPLTTAEQVGKWAARHIVNRINAFKPTADRPFVLGLPTGGTPMTTYKALVEMHKAGQ
              10        20        30        40        50        60

60        70        80        90       100       110
NAG1   VSFKNVVTFNMDEYLGFAPSDLQSYHYFMYDKFFNHIDIPRENIHILNGLAANIDEECAN
       :::::.::::::.. ..  .::. ::. .::.:.::: :::..::: :...::: .
NAG3   VSFKHVVTFNMDEYVGLPKEHPESYYSFMHERNFFDHVDIPAENINLLNGNAPDIDAECRQ
              70        80        90       100       110       120

120       130       140       150       160       170
NAG1   YEKKIKQYGRIDLFLGGLGPEGHLAFNEAGSSRNSKTRKVELVESTIKANCRFFGNDESK
       ::.::. ::.:: :.. ...: .:::::::..::  .::: .:....: ::.::.. ..
NAG3   YEEKIRSYGKIHLFMGGVGNDGHIAFNEPASSLASRTRIKTLTHDTRVANSRFFDNDVNQ
              130       140       150       160       170       180

180       190       200       210       220       230
NAG1   VPKYALSVGISTILDNSDEIAIIVLGKSKQFALDKTVNGKPNDPKYPSSYLQDHANVLIV
       ::::::::.::..:::. ...: ..:::. .  ...:.: :    ..:: :.......:
NAG3   VPKYALTVGVGTLLD-AEEVMILVLGSQKALALQAAVEG-CVNHMWTISCLQLHPKAIMV
              190       200       210       220       230

240
NAG1   CDNAAA-GLKSKL    SEQ ID NO:5
       ::....  .::  :
NAG3   CDEPSTMELKVKTLRYFNELEAENIKGL    SEQ ID NO:3
              240       250       260
```

*FIG. 4*

Upstream primer    SEQ ID NO:6

<u>Bgl II</u>    <u>Plant 5'</u>  <u>Start</u>
TAAGATCTAAACAACAACATGAGACTGATCCCCCTGAC Downstream primer    SEQ ID NO:7

<u>Xho I</u>         <u>Stop</u>
ACCTCGAGCAGGGATAACAATTACAGAC

*FIG.5*

A. Concensus sequence for plant introns   SEQ ID NO:21
B. DNA sequence of nagB coding region.   SEQ ID NO:22
C. Amino acid sequence of nagB coding region.   SEQ ID NO:4
D. DNA sequence of splice sites of IV2 intron in nagB   SEQ ID NO:23

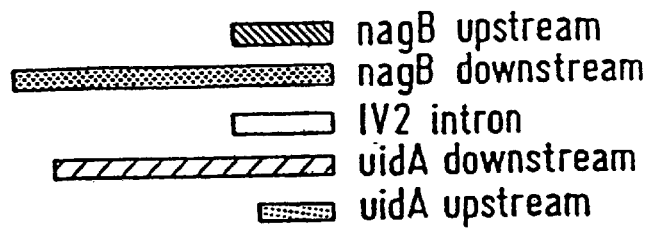
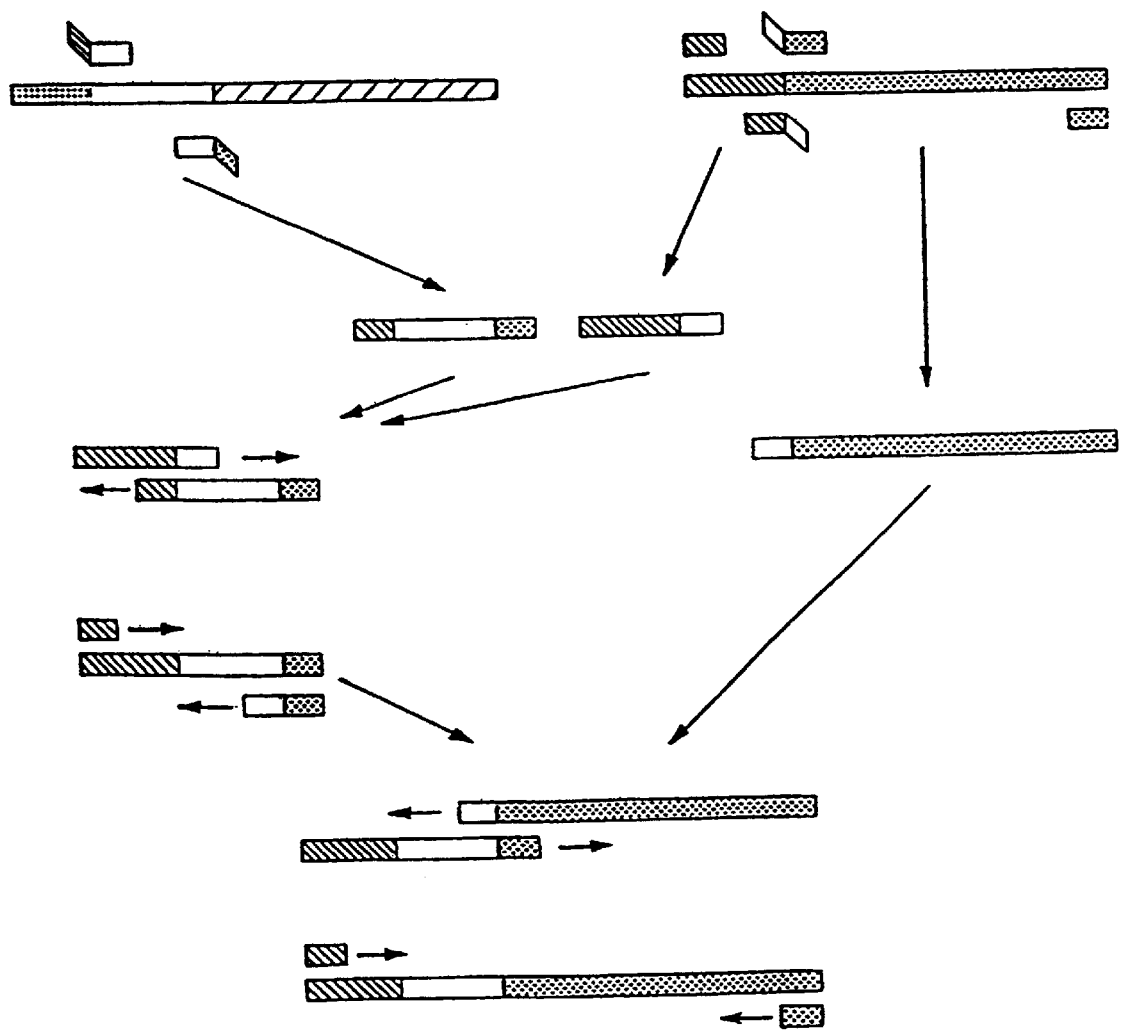
FIG. 7

SEQ ID NO 1

GATCTAAACAACAACATGAGACTGATCCCCCTGACTACCGCTGAACAGGTCGGCAAATGGG
CTGCTCGCCATATCGTCAATCGTATCAATGCGTTCAAACCGACTGCCGATCGTCCGTTTGT
ACTGGGCCTGCCGACTGGCGGCACGCCGATGACCACCTATAAAGCGTTAGTCGAAATGCAT
AAAGCAGGCCAGGTCAGCTTTAAGCACGTTGTCACCTTCAACATGGACGAATATGTCGGTC
TGCCGAAAGAGCATCCGGAAAGCTACTACAGCTTTATGCACCGTAATTTCTTCGATCACGT
TGATATTCCAGCAGAAAACATCAACCTTCTCAACGGCAACGCCCCGGATATCGACGCCGAG
TGCCGCCAGTATGAAGAAAAAATCCGTTCTTACGGAAAAATTCATCTGTTTATGGGCGGTG
TAGGTAACGACGGTCATATTGCATTTAACGAACCGGCGTCTTCTCTGGCTTCTCGTACTCG
TATCAAAACCCTGACTCATGACACTCGCGTCGCAAACTCTCGTTTCTTTGATAACGATGTT
AATCAGGTGCCAAAATATGCCCTGACTGTCGGTGTTGGTACACTGCTGGATGCCGAAGAGG
TGATGATTCTGGTGCTGGGTAGCCAGAAAGCACTGGCGCTGCAGGCCGCCGTTGAAGGTTG
CGTGAACCATATGTGGACCATCAGCTGTCTGCAACTGCATCCGAAAGCGATCATGGTGTGC
GTAGAACCTTCCACCATGGAGCTGAAAGTTAAGACTTTAAGATATTTCAATGAATTAGAAG
CAGAAAATATCAAAGGTCTGTAATTGTTATCCCTGCTCGAG

SEQ ID NO 2

TGCAGAGATCTAAACAACAACATGAGACTGATCCCCCTGACTACCGCTGAACAGGTCGGCA
AATGGGCTGCTCGCCATATCGTCAATCGTATCAATGCGTTCAAACCGACTGCCGATCGTCC
GTTTGTACTGGGCCTGCCGACTGGCGGCACGCCGATGACCACCTATAAAGCGTTAGTCGAA
ATGCATAAAGCAGGCCAGGTCAGCTTTAAGCACGTTGTCACCTTCAACATGGTAAGTTTCT
GCTTCTACCTTTGATATATATATAATAATTATCATTAATTAGTAGTAATATAATATTTCAA
ATATTTTTTCAAAATAAAAGAATGTAGTATATAGCAATTGCTTTTCTGTAGTTTATAAGT
GTGTATATTTTAATTTATAACTTTTCTAATATATGACCAAAATTTGTTGATGTGCAGGACG
AATATGTCGGTCTGCCGAAAGAGCATCCGGAAAGCTACTACAGCTTTATGCACCGTAATTT
CTTCGATCACGTTGATATTCCAGCAGAAAACATCAACCTTCTCAACGGCAACGCCCCGGAT
ATCGACGCCGAGTGCCGCCAGTATGAAGAAAAAATCCGTTCTTACGGAAAAATTCATCTGT
TTATGGGCGGTGTAGGTAACGACGGTCATATTGCATTTAACGAACCGGCGTCTTCTCTGGC
TTCTCGTACTCGTATCAAAACCCTGACTCATGACACTCGCGTCGCAAACTCTCGTTTCTTT
GATAACGATGTTAATCAGGTGCCAAAATATGCCCTGACTGTCGGTGTTGGTACACTGCTGG
ATGCCGAAGAAGTGATGATTCTGGTGCTGGGTAGCCAGAAAGCACTGGCGCTGCAGGCCGC
CGTTGAAGGTTGCGTGAACCATATGTGGACCATCAGCTGTCTGCAACTGCATCCGAAAGCG
ATCATGGTGTGCGATGAACCTTCCACCATGGAGCTGAAAGTTAAGACTTTAAGATATTTCA
ATGAATTAGAAGCAGAAAATATCAAAGGTCTGTAATTGTTATCCCTGCTCGAGGCATG

SEQ ID NO 3

MRLIPLTTAEQVGKWAARHIVNRINAFKPTADRPFVLGLPTGGTPMTTYKALVEMHKAGQV
SFKHVVTFNMDEYVGLPKEHPESYYSFMHRNFFDHVDIPAENINLLNGNAPDIDAECRQYE
EKIRSYGKIHLFMGGVGNDGHIAFNEPASSLASRTRIKTLTEDTRVANSRFFDNDVNQVPK
YALTVGVGTLLDAEEVMILVLGSQKALALQAAVEGCVNHMWTISCLQLHPKAIMVCDEPST
MELKVKTLRYFNELEAENIKGL*

FIG.28

METHOD OF PLANT SELECTION USING GLUCOSAMINE-6-PHOSPHATE DEAMINASE

RELATED APPLICATIONS

This is the U.S. national phase under 35 U.S.C. §371 of International Application PCT/GB98/00367, filed Jul. 12, 1996, which claims priority to GB 9702592.8, filed Feb. 7, 1997.

FIELD OF THE INVENTION

The present invention relates to a selection method.

The present invention also relates to an enzyme and a nucleotide sequence coding for same that are useful in a selection method.

In particular, the present invention relates to a method for the selection (e.g. identification and/or separation) of genetically transformed cells and compounds and genetic material for use in the method.

BACKGROUND OF THE INVENTION

It is well known that when a nucleotide sequence of interest ("NOI") is to be introduced into a population of cells by transformation, only a certain number of the cells are successfully transformed, i.e. receive the NOI. It is then necessary to identify the genetically transformed cells so that these cells may be separated from the non-transformed cells in the population.

A common technique for a selection method includes introducing transformed cells and non-transformed cells into a medium that comprises a substance which the transformed cells are able to tolerate. In that medium the transformed cells are able to survive and grow, while the non-transformed cells are prone to growth inhibition and, in some cases, are killed.

To date, if a population of plant cells has been subjected to genetic transformation, selection of the transformed cells typically takes place using a selection gene which codes for antibiotic resistance or herbicide resistance. The selection gene is coupled to or co-introduced with the NOI to be incorporated into the plant in question, so that both of the two genes are incorporated into some or all of the population of cells.

As not all of the cells may have been transformed, the cells are then cultivated on or in a medium containing the respective antibiotic or herbicide to which the genetically transformed cells are resistant by virtue of the selection gene. In this medium, the transformed cells are able to grow and thus be identified out of the total cell population, since the non-transformed cells— which do not contain the antibiotic or herbicide resistance gene in question—have an inhibited growth or even are killed.

These selection methods which rely on the use of antibiotics or herbicides suffer from a number of disadvantages. For example, there is concern amongst some people, such as environmental groups and governmental authorities, as to whether it is environmentally safe to incorporate genes coding for antibiotic resistance and/or herbicide resistance into plants and micro-organisms. This concern is of particular significance for food plants and for micro-organisms which are not designed and/or intended to be used in a closed environment (e.g. micro-organisms for use in agriculture), and also for micro-organisms which are designed for use in a closed environment but which may be released from the closed environment. While these concerns may prove to be unfounded, each concern may nevertheless lead to governmental restrictions on the use of antibiotic resistance genes and/or herbicide resistance genes in e.g. plants.

It is therefore desirable to develop new methods for selecting genetically transformed cells or organisms (or parts thereof) comprising such.

SUMMARY OF THE INVENTION

According to a first aspect of the present invention there is provided a selection method for selecting from a population of cells one or more selectable genetically transformed cells, wherein the population of cells comprises selectable genetically transformed cells and possible non-transformed cells; wherein each of the selectable genetically transformed cells comprises a first expressable nucleotide sequence and optionally a second expressable nucleotide sequence; wherein a component or a metabolic derivative thereof when present in a low concentration in a medium is a nutrient for both the selectable genetically transformed cells and the non-transformed cells; wherein the component or the metabolic derivative thereof when present in a high concentration in a medium is toxic to the non-transformed cells; wherein the first nucleotide sequence codes for a gene product capable of converting the component or the metabolic derivative thereof when present in a high concentration in a medium to a nutrient for the selectable genetically transformed cells; the method comprising the step of introducing the population of cells to a medium, wherein the medium optionally comprises a high concentration of the component or the metabolic derivative thereof, and either wherein the component or the metabolic derivative thereof is a source of both carbohydrate and nitrogen for the selectable genetically transformed cells; or wherein if a portion of the component serves as a metabolic substrate and is metabolically converted to a derivatised substrate, then that derivatised substrate is capable of providing an allosteric effect on the gene product.

According to a second aspect of the present invention there is provided a composition comprising a population of cells comprising selectable genetically transformed cells and possible non-transformed cells; and a medium, wherein each of the selectable genetically transformed cells comprises a first expressable nucleotide sequence and optionally a second expressable nucleotide sequence; wherein a component or a metabolic derivative thereof when present in a low concentration in a medium is a nutrient for both the selectable genetically transformed cells and the non-transformed cells; wherein the component or the metabolic derivative thereof when present in a high concentration in a medium is toxic to the non-transformed cells; wherein the first nucleotide sequence codes for a gene product capable of converting the component or the metabolic derivative thereof when present in a high concentration in a medium to a nutrient for the selectable genetically transformed cells; the medium optionally comprising a high concentration of the component or the metabolic derivative thereof, and either wherein the component or the metabolic derivative thereof is a source of both carbohydrate and nitrogen for the selectable genetically transformed cells; or wherein if a portion of the component serves as a metabolic substrate and is metabolically converted to a derivatised substrate, then that derivatised substrate is capable of providing an allosteric effect on the gene product.

According to a third aspect of the present invention there is provided a population of cells comprising selectable genetically transformed cells and possible non-transformed cells; wherein each of the selectable genetically transformed cells comprises a first expressable nucleotide sequence and optionally a second expressable nucleotide sequence; wherein a component or a metabolic derivative thereof when present in a low concentration in a medium is a nutrient for both the selectable genetically transformed cells and the non-transformed cells; wherein the component or the metabolic derivative thereof when present in a high concentration in a medium is toxic to the non-transformed cells; wherein the first nucleotide sequence codes for a gene product capable of converting the component or the metabolic derivative thereof when present in a high concentration in a medium to a nutrient for the selectable genetically transformed cells; and either wherein the component or the metabolic derivative thereof is a source of both carbohydrate and nitrogen for the selectable genetically transformed cells; or wherein if a portion of the component serves as a metabolic substrate and is metabolically converted to a derivatised substrate, then that derivatised substrate is capable of providing an allosteric effect on the gene product.

According to a fourth aspect of the present invention there is provided a selectable genetically transformed cell comprising a first expressable nucleotide sequence and optionally a second expressable nucleotide sequence; wherein a component or a metabolic derivative thereof when present in a low concentration in a medium is a nutrient for the selectable genetically transformed cell and a non-transformed cell; wherein the component or the metabolic derivative thereof when present in a high concentration in a medium is toxic to a non-transformed cell; wherein the first nucleotide sequence codes for a gene product capable of converting the component or the metabolic derivative thereof when present in a high concentration in a medium to a nutrient for the selectable genetically transformed cell; and either wherein the component or the metabolic derivative thereof is a source of both carbohydrate and nitrogen for the selectable genetically transformed cell; or wherein if a portion of the component serves as a metabolic substrate and is metabolically converted to a derivatised substrate, then that derivatised substrate is capable of providing an allosteric effect on the gene product.

According to a fifth aspect of the present invention there is provided a construct for genetically transforming a non-transformed cell to produce a selectable genetically transformed cell; the construct comprising a first expressable nucleotide sequence and optionally a second expressable nucleotide sequence; wherein a component or a metabolic derivative thereof when present in a low concentration in a medium is a nutrient for the selectable genetically transformed cell and a non-transformed cell; wherein the component or the metabolic derivative thereof when present in a high concentration in a medium is toxic to a non-transformed cell; wherein the first nucleotide sequence codes for a gene product capable of converting the component or the metabolic derivative thereof when present in a high concentration in a medium to a nutrient for the selectable genetically transformed cell; and either wherein the component or the metabolic derivative thereof is a source of both carbohydrate and nitrogen for the selectable genetically transformed cell; or wherein if a portion of the component serves as a metabolic substrate and is metabolically converted to a derivatised substrate, then that derivatised substrate is capable of providing an allosteric effect on the gene product.

According to a sixth aspect of the present invention there is provided a vector comprising a construct for genetically transforming a non-transformed cell to produce a selectable genetically transformed cell; the construct comprising a first expressable nucleotide sequence and optionally a second expressable nucleotide sequence; wherein a component or a metabolic derivative thereof when present in a low concentration in a medium is a nutrient for the selectable genetically transformed cell and a non-transformed cell; wherein the component or the metabolic derivative thereof when present in a high concentration in a medium is toxic to a non-transformed cell; wherein the first nucleotide sequence codes for a gene product capable of converting the component or the metabolic derivative thereof when present in a high concentration in a medium to a nutrient for the selectable genetically transformed cell, and either wherein the component or the metabolic derivative thereof is a source of both carbohydrate and nitrogen for the selectable genetically transformed cell; or wherein if a portion of the component serves as a metabolic substrate and is metabolically converted to a derivatised substrate, then that derivatised substrate is capable of providing an allosteric effect on the gene product.

According to a seventh aspect of the present invention there is provided a plasmid comprising a construct for genetically transforming a non-transformed cell to produce a selectable genetically transformed cell; the construct comprising a first expressable nucleotide sequence and optionally a second expressable nucleotide sequence; wherein a component or a metabolic derivative thereof when present in a low concentration in a medium is a nutrient for the selectable genetically transformed cell and a non-transformed cell; wherein the component or the metabolic derivative thereof when present in a high concentration in a medium is toxic to a non-transformed cell; wherein the first nucleotide sequence codes for a gene product capable of converting the component or the metabolic derivative thereof when present in a high concentration in a medium to a nutrient for the selectable genetically transformed cell; and either wherein the component or the metabolic derivative thereof is a source of both carbohydrate and nitrogen for the selectable genetically transformed cell; or wherein if a portion of the component serves as a metabolic substrate and is metabolically converted to a derivatised substrate, then that derivatised substrate is capable of providing an allosteric effect on the gene product.

According to an eighth aspect of the present invention there is provided an organism comprising a selectable genetically transformed cell; wherein the selectable genetically transformed cell comprises a first expressable nucleotide sequence and optionally a second expressable nucleotide sequence; wherein a component or a metabolic derivative thereof when present in a low concentration in a medium is a nutrient for the selectable genetically transformed cell and a non-transformed cell; wherein the component or the metabolic derivative thereof when present in a high concentration in a medium is toxic to a non-transformed cell; wherein the first nucleotide sequence codes for a gene product capable of converting the component or the metabolic derivative thereof when present in a high concentration in a medium to a nutrient for the selectable genetically transformed cell; and either wherein the component or the metabolic derivative thereof is a source of both carbohydrate and nitrogen for the selectable genetically transformed cell; or wherein if a portion of the component serves as a metabolic substrate and is metabolically converted to a derivatised substrate, then that derivatised substrate is capable of providing an allosteric effect on the gene product.

According to a ninth aspect of the present invention there is provided a kit comprising a construct (such as when contained within or on a vector or in a plasmid) for genetically transforming a non-transformed cell to produce a selectable genetically transformed cell; and a medium; the construct comprising a first expressable nucleotide sequence and optionally a second expressable nucleotide sequence; wherein a component or a metabolic derivative thereof when present in a low concentration in a medium is a nutrient for the selectable genetically transformed cell and a non-transformed cell; wherein the component or the metabolic derivative thereof when present in a high concentration in a medium is toxic to a non-transformed cell; wherein the first nucleotide sequence codes for a gene product capable of converting the component or the metabolic derivative thereof when present in a high concentration in a medium to a nutrient for the selectable genetically transformed cell; the medium optionally comprising a high concentration of the component or the metabolic derivative thereof; and either wherein the component or the metabolic derivative thereof is a source of both carbohydrate and nitrogen for the selectable genetically transformed cell; or wherein if a portion of the component serves as a metabolic substrate and is metabolically converted to a derivatised substrate, then that dervatised substrate is capable of providing an allosteric effect on the gene product.

According to a tenth aspect of the present invention there is provided a plant or plant cell prepared from or comprising the above-mentioned aspects of the present invention.

According to an eleventh aspect of the present invention there is provided a plant or plant cell comprising a heterologous enzyme and/or nucleotide sequence encoding same, wherein the heterologous enzyme is glucosamine-6-phosphate deaminase.

This aspect of the present invention is very advantageous. In this regard, not only does the enzyme itself act as a selection means for some transformed cells (for example potato cells) but furthermore it beneficially affects the mobilisation of glycloproteins during conditions of limited nitrogen availability. An example of the latter advantageous aspect is the mobilisation of seed glycoproteins in germinating legumninous seedlings before they have established their symbiotic relationship with micro-organisms (e.g. bacterium) that are capable of fixing atmospheric nitrogen. In this case, the glycoproteins would for example be converted to N-acteyl-glucosamine and then into glucosamine-6-phosphate, which would then be converted to fructose-6-phosphate by the glucosamine-6-phosphate deaminase.

According to a twelfth aspect of the present invention there is provided a foodstuff or food prepared from or comprising the above-mentioned aspects according to the present invention.

In each aspect of the present invention, the metabolic substrate is preferably metabolically converted to a derivatised substrate by the transformed cell.

If component or the metabolic derivative thereof is present in the medium then the component or the metabolic derivative thereof is present in an amount that does not detrimentally affect a major proportion of the transformed cells.

Preferably, if component or the metabolic derivative thereof is present in the medium then the component or the metabolic derivative thereof is present in an amount that does not detrimentally affect substantially most of the transformed cells.

More preferably, if a component or the metabolic derivative thereof is present in the medium then the component or the metabolic derivative thereof is present in an amount that does not detrimentally affect substantially all of the transformed cells.

In one embodiment of the present invention the medium comprises a high concentration of the component or the metabolic derivative thereof.

However, in an alternative embodiment the medium does not necessarily have to comprise a high concentration of the component or the metabolic derivative thereof. In a further aspect, we have even surprisingly found that in some cases the medium need not contain any added quantities of the component or the metabolic derivative according to the present invention. By way of example, this surprising finding was observed in transgenic potato plants according to the present invention wherein those plants comprise cells containing the nagB gene (as discussed herein). In this regard, it is believed that the levels of glucosamine and/or glucosamine-6-phosphate already present (including the endogeneous levels) were sufficiently high as a result of exposure of the plants to the particular culture medium that was used such that the transformed potato cells could metabolise any endogenous glucosamine-6-phosphate whereas in the wild type plants the levels of endogenous glucosamine-6-phosphate were sufficiently toxic so as to destroy their viability.

Thus, other aspects of the present invention include:

The use of glucosamine-6-phosphate deaminase as a selection means for selecting a genetically transformed cell over a non-transformed cell.

The use of a gene coding for glucosamine-6-phosphate deaminase for providing a selection means for selecting a genetically transformed cell over a non-transformed cell.

A gene for providing a selection means for selecting a genetically transformed cell over a non-transformed cell; wherein the gene is obtainable from NCIMB 40852 or NCIMB 40853 or NCIMB 40854.

The use of a gene obtainable from NCIMB 40852 or NCIMB 40853 or NCIMB 40854 for providing a selection means for selecting a genetically transformed cell over a non-transformed cell.

NCIMB 40852 or NCIMB 40853 or NCIMB 40854.

Additional aspects of the present invention include:

A process of inactivating a gene or gene product that is potentially detrimental to a prokaryote when present in the prokaryote by the insertion of at least one intron into the gene (in particular into the coding portion) thereby inactivating the gene or the gene product vis-à-vis the prokaryote.

A prokaryote comprising a gene that would have been potentially detrimental to a prokaryote when present in the prokaryote, but wherein the gene comprises at least one intron which inactivates the gene or the product thereof in the prokaryote—in particular wherein the intron is present within a coding portion of the gene.

With these additional aspects of the present invention, preferably the at least one intron is inserted into a conserved region of the gene, preferably a conserved region within a coding region.

The enzyme glucosamine-6-phosphate deaminase can also be called 2-amino-2-deoxy-D-glucose-6-phosphate ketol isomerase (deaminating). This enzyme has the enzyme commission number EC 5.3.1.10.

In the above aspects, the phrase " . . . for selecting a genetically transformed cell over a non-transformed cell . . . " can be alternatively expressed as—for example " . . . for selecting a genetically transformed cell from one or more non-transformed cells . . . ".

Thus, according to one aspect of the present invention there is provided a selection system for selecting at least one genetically transformed cell from a population of cells in a medium, wherein the at least one genetically transformed cell is transformed with a nucleotide sequence which encodes a gene product capable of converting a component present in the medium at a level that is toxic to non-transformed cells into a nutrient for the at least one transformed cell; wherein said component provides a source of nitrogen and carbohydrate for the transformed cell and/or wherein said component serves as a metabolic substrate, at least one metabolite of which has an allosteric effect on the gene product. The present invention also provides enzymes and nucleotides useful in that system.

Preferably the component or the metabolic derivative thereof is a source of both carbohydrate and nitrogen for the selectable genetically transformed cell(s); and wherein if a portion of the component serves as a metabolic substrate and is metabolically converted to a derivatised substrate, then that derivatised substrate is capable of providing an allosteric effect on the gene product.

Preferably the component is capable of furnishing to the selectable genetically transformed cell(s) a source of both carbohydrate and nitrogen.

Preferably the component or the metabolic derivative thereof comprises an amine group.

Preferably the component is glucosamine.

Preferably the metabolic derivative of the component that is toxic to the non-transformed cells comprises a phosphate group and/or is formed by phosphate groups that would otherwise be beneficially utilised by a wild type cell. Alternatively or in addition, the metabolic derivative of the component that is toxic to the non-transformed cells is responsible for sequestration of phosphate groups that would otherwise be beneficially utilised by a wild type cell.

Preferably the metabolic derivative of the component that is toxic to the non-transformed cells comprises an amine group.

Preferably the metabolic derivative of the component that is toxic to the non-transformed cells is capable of furnishing to the selectable genetically transformed cell(s) a source of both carbohydrate and nitrogen.

Preferably the metabolic derivative of the component that is toxic to the non-transformed cells is glucosamine-6-phosphate.

Preferably the derivatised substrate comprises an amine group and/or a phosphate group.

Preferably the derivatised substrate is N-acetyl-glucosamine-6-phosphate.

Preferably the first nucleotide sequence comprises an intron.

Preferably the gene product is an enzyme.

Preferably the enzyme is capable of modifying a glycoprotein precursor.

Preferably the enzyme is capable of deaminating a glycoprotein precursor.

Preferably the enzyme is glucosamine-6-phosphate deaminase.

Preferably the enzyme is glucosamine-6-phosphate deaminase obtainable from a micro-organism.

Preferably the enzyme is glucosamine-6-phosphate deaminase obtainable from a bacterium.

Preferably the enzyme is glucosamine-6-phosphate deaminase obtainable from E. Coli.

Preferably the enzyme glucosamine-6-phosphate deaminase has the amino acid sequence shown as SEQ ID No. 3 or is a variant, homologue or fragment thereof.

Preferably the enzyme glucosamine-6-phosphate deaminase is encoded by either the nucleotide sequence shown as SEQ ID No. 1 or a variant, homologue or fragment thereof or a sequence that is complementary to a sequence that hybridises thereto, or the nucleotide sequence shown as SEQ ID No. 2 or a variant, homologue or fragment thereof or a sequence that is complementary to a sequence that hybridises thereto.

Preferably the glucosamine-6-phosphate deaminase or the gene encoding same is obtainable from NCIMB 40852 or NCIMB 40853 or NCIMB 40854.

Preferably the selectable genetically transformed cell/cells is/are either in vitro within a culture or in vivo within an organism.

Preferably the selectable genetically transformed cell/cells is/are selectable genetically transformed plant cell/cells.

Preferably the second nucleotide sequence is present and wherein the second nucleotide sequence codes for a nucleotide sequence of interest.

Preferably the plant is capable of providing a foodstuff to humans or animals.

Preferably the plant (or part thereof, including cells thereof) is a monocot or a dicot (including legumes).

Preferably the plant (or part thereof, including cells thereof) is any one of guar, potato or maize.

The present invention therefore provides a method for selecting genetically transformed cells—such as cells into which a nucleotide sequence of interest ("NOI") has been incorporated—by providing the transformed cells with a selective advantage.

The method of the present invention is not dependent on the preparation of genetically transformed plants containing as a selection means a nucleotide sequence coding for antibiotic or herbicide resistance. Nevertheless, the method of the present invention can be used in conjunction with those earlier selection methods should the need arise—if for example it is desirable to prepare cells that have been or are to be transformed with a number of NOIs.

Also, the selection method of the present invention can be used in conjunction with one or more other known selection methods, such as those that are described in WO 93/05163 (the contents of which are incorporated herein by reference) and/or WO 94/20627 (the contents of which are incorporated herein by reference), should the need arise—if for example it is desirable to prepare cells that have been transformed with a number of NOIs.

In addition, the selection method of the present invention can be used in conjunction with one or more other selection methods according to the present invention should the need arise—if for example it is desirable to prepare cells that have been transformed with a number of NOIs.

A further beneficial use of a combination of selection methods according to the present invention results in a very efficient multiple screening technique. As indicated above, the presence of the component or the metabolic derivative thereof in the medium is an optional feature. Moreover, in some cases, it may not be necessary to add the component or the metabolic derivative thereof to the medium. Both of these aspects of the present invention could be used in a combined selection process that comprises two screening steps. In this regard, and by way of example, the medium in the first screen utilising the selection method of the present invention would not contain added amounts of the component or the metabolic derivative thereof. With this first screen, selectable transformed cells are selected over at least the majority of the non-transformed cells. Then should—for example—any non-transformed cells be accidentally be carried over in that first screen then a second screen can be cried out. In the second screen the selected population of cells are subjected to a second selection method according to the present invention but wherein the component or the metabolic derivative thereof is present in the medium, preferably in a high concentration. In the second screen, only the transformed cells would remain viable.

With this combined aspect of the present invention, the population of cells of the earlier aspects of the present invention can therefore be a pre-selected (e.g. pre-screened) population of cells, wherein the population of cells has been prior selected by one or more selection methods, such as those according to the present invention.

This combined aspect of the present invention can be alternatively expressed as: a selection method for selecting from a population of cells one or more selectable genetically transformed cells, wherein the population of cells comprises selectable genetically transformed cells and possible non-transformed cells; wherein each of the selectable genetically transformed cells comprises a first expressable nucleotide sequence and optionally a second expressable nucleotide sequence; wherein a component or a metabolic derivative thereof when present in a low concentration in a medium is a nutrient for both the selectable genetically transformed cells and the non-transformed cells; wherein the component or the metabolic derivative thereof when present in a high concentration in a medium is toxic to the non-transformed cells; wherein the first nucleotide sequence codes for a gene product capable of converting the component or the metabolic derivative thereof when present in a high concentration in a medium to a nutrient for the selectable genetically transformed cells; and either wherein the component or the metabolic derivative thereof is a source of both carbohydrate and nitrogen for the selectable genetically transformed cells; or wherein if a portion of the component serves as a metabolic substrate and is metabolically converted to a derivatised substrate, then that derivatised substrate is capable of providing an allosteric effect on the gene product; the method comprising the step of introducing the population of cells to a medium and then selecting at least a potion of the transformed cells over the non-transformed cells, and subsequently introducing the at least portion of the transformed cells to a medium that comprises a high concentration of the component or the metabolic derivative thereof.

The present invention also encompasses compositions and kits useful for this combined aspect of the present—such as the gene or gene product according to the present invention, a first medium containing no component or metabolic derivative thereon and a second medium comprising a high concentration of the component or metabolic derivative thereof.

Furthermore, the selection method of the present invention can be used in conjunction with further selection methods wherein those further selection methods are a combination of one or more other selection methods according to the present invention and one or more known selection methods—such as those that are dependent on antibiotic or herbicide resistance and/or those that are disclosed in WO 93/05163 and/or WO 94/20627.

In the selection methods of WO 93/05163 and/or WO 94/20627, the manA gene from *Escherichia coli*, which encodes mannose-6-phosphate isomerase (E.C. 5.3.2.8.), was employed as a selectable marker. This selection marker is suitable for infer alia the transformation of *Solanum tuberosum*, conferring positive selection in the presence of mannose. In more detail, the coding region of manA was ligated into a CaMV 35S expression cassette, and introduced into a binary vector for plant transformation mediated by *Agrobacterium tumefaciens*. To allow comparison of kanamycin selection with selection on mannose, the vector also contained a gene for kanamycin resistance, nptII. In order to identify transformants, the construction also contained the B-glucuronidase histochemical marker, uidA. Stable integration of the manA gene was shown by Southern blotting. Extracts from plants transformed with this construct, and selected on mannose, were shown to have specific activities for mannose-6-phosphate isomerase some five hundred fold those of control plants. Expression of manA in transformed cells relieved the metabolic paralysis, usually caused by mannose, while also allowing it to serve as a source of carbohydrate for transformants. These effects combined to impose a stringent selection pressure in favour of transformed cells, which allowed the recovery of transformants with a very low frequency of escapes. The percentage of shoots which were shown to be transgenic after selection on mannose was approximately twice that of shoots selected on kanamycin. The transformants selected on mannose have proven to be stable over three generations of plants propagated from tubers.

Hence, the population of cells of the earlier aspects of the present invention can therefore be a pre-selected (e.g. pre-screened) population of cells, wherein the population of cells has been prior selected by one or more selection methods according to the present invention and/or one or more other selection methods.

In addition, or in the alternative, the transformed cells selected by the selection method of the present invention can be subsequently subjected to one or more selection methods according to the present invention and/or one or more other selection methods.

The present invention also provides an expression system that enables transformed cells to be selected by the selection method of the present invention. The expression system can be expressing or can be capable of expressing the first nucleotide sequence of the present invention. The expression system may be one or more of a vector, construct, plasmid, cell or organism.

If a cell is also to be transformed with a NOI then the expression system will comprise that NOI—which NOI may be present on or in the same vector, construct, plasmid, cell or organism as the first nucleotide sequence. Alternatively the NOI may be present on or in a different vector, construct, plasmid, cell or organism as the first nucleotide sequence. Preferably, the NOI is present on or in the same vector, construct, plasmid, cell or organism as the first nucleotide sequence.

If a cell is to be transformed with one or more NOIs and one or more other genes for one or more other selection methods (such as another selection method according to the present invention and/or a known selection method) those other nucleotide sequences may be present on or in the same vector, construct, plasmid, cell or organism as the first nucleotide sequence. Alternatively one or more of those other nucleotide sequences may be present on or in a different vector, construct, plasmid, cell or organism as the first nucleotide sequence. Preferably, those other nucleotide sequences are present on or in the same vector, construct, plasmid, cell or organism as the first nucleotide sequence. This allows for workers to easily prepare and easily select for cells that have been transformed with a number of NOIs etc.

The term "cells" is intended to refer to any type of cells from which individual genetically transformed cells may be identified and isolated using the method of the invention. Examples of such cells include plant cells, animal cells and micro-organisms such as bacteria, fungi, yeast etc. The term "cells" is also meant to encompass protoplasts, i.e. the protoplasm of a cell enclosed in a membrane but without a cell wall. While it is contemplated that the selection method of the present invention may be used for any type of cell, the method has been found to be particularly suitable for the selection of genetically transformed plant cells.

The term "population of cells" refers to any group of cells which has been subjected to genetic transformation and from which it is desired to identify those cells which have been genetically transformed and to isolate the genetically transformed cells from non-genetically transformed cells. The population may, for example, be a tissue, an organ or a portion thereof, a population of individual cells in or on a substrate, such as a culture of micro-organism cells, for example a population of cells in a solution or suspension, or a whole organism, such as an entire plant.

The term "selecting" refers to the process of identifying and/or isolating the genetically transformed cells from the non-genetically transformed cells using the method of the present invention.

The term "toxic to the non-transformed cells" includes inhibited growth of the non-transformed cells as well as the death thereof.

The term "medium" includes any medium that is capable of providing the transformed cells with a selective advantage, such as a selective growth advantage. For example, the medium may comprise typical ingredients of a growth medium but wherein those ingredients are in such an amount that only the transformed cells are selectively grown. In some embodiments of the present invention, the medium will comprise a component, or a metabolic precursor therefor, according to the present invention, and preferably in a high concentration.

In this regard, that component—such as an added component or derived from the added precursor—or a metabolic derivative thereof is a nutrient for the non-transformed cells when the component is present in low concentrations and wherein the component or a metabolic derivative thereof is toxic to the non-transformed cells when the component is present in high concentrations.

Preferably, the term "low concentration" means greater than 0 $\mu$M to less than 25 $\mu$M. Typical preferred examples of low concentrations are in the $\mu$-molar range.

Preferably, the term "high concentration" means at least 25 $\mu$M and up to 100 mM (or in some instances even higher). Typical preferred examples of high concentrations are in the milli-molar range.

The term "nutrient" includes a substance that is capable of providing directly or indirectly (e.g. via a metabolite thereof) energy or atoms that are beneficially useful for maintenance and/or growth and/or reproduction etc. of the cell, tissue, organ or organism. For example, the term includes a substrate that can be beneficially metabolised and/or beneficially utilised in a metabolic pathway to enable the transformed cells to grow, to proliferate or to be maintained in a viable form.

The term "genetically transformed" includes transformation using recombinant DNA techniques.

The term "introducing the population of cells to a medium" means adding the population of cells to the medium or vice versa.

If a portion of the component serves as a metabolic substrate and is metabolically converted to a derivatised substrate, wherein that derivatised substrate is capable of providing an allosteric effect on the gene product, then the metabolic conversion can be a one step metabolic conversion process or it can be a multi-step metabolic conversion process.

The component of the present invention may be derived from a metabolic precursor therefor.

The terms "non-transformed cells" or "non-transformed cell" mean cells or a cell that do not or does not comprise the first nucleotide sequence according to the present invention. The terms also include cells or a cell that do not or does not comprise another first nucleotide sequence when the genetically transformed cells or cell comprise or comprises two different first nucleotide sequences. The terms also include any previously transformed cell but wherein that previously transformed cell does not comprise a first nucleotide sequence according to the present invention or the same number of first nucleotide sequences as the transformed cell or cells.

In a highly preferred embodiment, the first nucleotide sequence is not in its natural environment. In this regard, the first nucleotide sequence may not be native (i.e. foreign) to the cell or organism. In addition, the first nucleotide sequence may be native to the cell or organism but wherein the first nucleotide sequence is operably linked to a promoter that is heterologous to the first nucleotide sequence.

The first nucleotide sequence may be DNA or RNA. Preferably, the first nucleotide sequence is DNA. More preferably, the first nucleotide sequence is recombinant DNA.

Likewise, the second nucleotide sequence may be DNA or RNA. Preferably, the second nucleotide sequence is DNA. More preferably, the second nucleotide sequence is recombinant DNA.

The term "nucleotide sequence of interest" (i.e. "NOI") means any desired nucleotide sequence for incorporation into the cells in question to produce genetically transformed cells. Introduction of nucleotide sequences into plants, micro-organisms and animals is widely practised, and it is believed that there are no limitations upon the nucleotide sequences whose presence may be selected (eg. detected) by use of the selection method of the present invention.

By use of the method of the present invention the presence of the NOI in the genetically transformed cells may be determined without the above-mentioned disadvantages associated with the selection systems relying solely on antibiotic resistance and/or herbicide resistance.

The NOI can be any nucleotide sequence of interest, such as any gene of interest. A NOI can be any nucleotide sequence that is either foreign or natural to the cell or organism (e.g. a particular plant) in question. Typical examples of a NOI include genes encoding proteins and enzymes that modify metabolic and catabolic processes. The NOI may code for an agent for introducing or increasing resistance to pathogens. The NOI may even be an antisense construct for modifying the expression of natural transcripts present in the relevant tissues. The NOI may even code for a compound that is of benefit to animals or humans. Examples of NOIs include nucleotide sequences encoding any one or more of pectinases, pectin depolymerases, polygalacturonases, pectate lyases, pectin lyases, rhamno-galacturonases, hemicellulases, endo-$\beta$-glucanases, arabinases, or acetyl esterases, or combinations thereof, as well as antisense sequences thereof. The NOI may encode a protein giving nutritional value to a food or crop. Typical examples include plant proteins that can inhibit the formation of anti-nutritive factors and plant proteins that have a more desirable amino acid composition (e.g. a higher lysine content than a non-transgenic plant).

The NOI may even code for an enzyme that can be used in food processing such as chymosin, thaumatin and α-galactosidase. The NOI can be a gene encoding for any one of a pest toxin, an antisense transcript such as that for patatin or α-amylase, ADP-glucose pyrophosphorylase (e.g. see EP-A-0455316), a protease antisense, a glucanase or genomic β1,4-endoglucanase.

The NOI may even code for or comprise an intron of a particular gene. Here the intron can be in sense or antisense orientation. In the latter instance, the particular gene could be DNA encoding β-1,4-endoglucanase. Antisense expression of genorric exon or intron sequences as the NOI would mean that the natural β-1,4-endoglucanase expression would be reduced or eliminated but wherein the expression of a β-1,4-endoglucanase gene according to the present invention would not be affected.

The NOI may be the nucleotide sequence coding for the arabinofuranosidase enzyme which is the subject of PCT patent application PCT/EP96/01009 (incorporated herein by reference). The NOI may be any of the nucleotide sequences coding for the ADP-glucose pyrophosphorylase enzymes which are the subject of PCT patent application PCT/EP94/01092 (incorporated herein by reference). The NOI may be any of the nucleotide sequences coding for the α-glucan lyase enzyme which are described in PCT patent application PCT/EP94/03397 (incorporated herein by reference). The NOI may be any of the nucleotide sequences coding for the glucanase enzyme which are described in PCT patent application PCT/EP96/01008 (incorporated herein by reference).

The NOI may also encode a permease or other transport factor which allows the compound or precursor thereof or metabolised derivative thereof to cross the cell membrane and enter the transformed cells. Instead of facilitating uptake of a compound into a cell, the co-introduced nucleotide sequence may alternatively direct the component or precursor thereof or metabolised derivative thereof to a specific compartment—such as the plasma membrane or into the vacuole or the endoplasmic reticulum.

More than one NOI can be present.

The NOI can be co-introduced with the first nucleotide sequence according to the present invention.

The term "co-introduced" means that the two nucleotide sequences may be coupled to each other, or are otherwise introduced together, in such a manner that the presence of the co-introduced first nucleotide sequence in a cell indicates that the NOI has been introduced into the cell, i.e. if the first nucleotide sequence is shown to have been introduced, the probability that the NOI has also been introduced is significantly increased. The two nucleotide sequences may be part of the same genetic construct and may be introduced by the same vector.

The methods described herein may also be used when the co-introduced first nucleotide sequence and the NOI are introduced independently. This may be performed, for example, by using the same bacteria for incorporation of both genes and incorporating a relatively large number of copies of the NOI into the cells, whereby the probability is relatively high that cells which are shown to express the first nucleotide sequence will also contain and express the NOI.

In order for the introduced first nucleotide sequence and optional NOI to be expressed in the transformed cells, the genetic constructs containing the first nucleotide sequence and/or NOI will typically, but not necessarily, contain regulatory sequences enabling expression of the nucleotide sequences, e.g. known promoters and transcription terminators. Thus, the first nucleotide sequence will typically be associated with a promoter, which may be a constitutive or regulatable promoter, and the NOI will typically also be associated with a constitutive or regulatable promoter.

As mentioned above, preferably the gene product of the present invention is the enzyme glucosamine-6-phosphate deaminase (EC 5.3.1.10). A gene coding for glucosamine-6-phosphate deaminase may be obtainable from non-plant organisms, such as *E. coli*. An example of such a gene is known as the nagB gene. This gene has been cloned and sequenced by Rogers, M J, et al ((1988) Gene 62: 197–207). However, those workers did not suggest the nag B gene could be expressed in plants, let alone be used in a selection method. Alternatively, the glucosamine-6-phosphate deaminase may be obtainable from plants, such as a mung bean shoot. An example of such activity was reported by Veiga, L A ((1968) Plant & Cell Physiol 9: 1–12)—but that author did not report on any sequence information.

The first nucleotide sequence and/or the NOI may comprise one or more introns. In particular, if the first nucleotide sequence and/or the NOI encodes a gene product that can detrimentally affect a bacterium and all or a part (e.g. a plasmid thereof or therein) of that bacterium is used either to propagate the NOI or as a means to transform the cells, then it is highly desirable for that gene product to be inactive in the bacterium. One way of selectively inactivating the gene product in bacteria is to insert one or more introns into the nucleotide sequence of the first nucleotide sequence or the NOI. This intron or those introns would not be removed after transcription in the bacterium but would be so removed in, for example, plants etc.

In a highly preferred embodiment, if the first nucleotide sequence and/or the NOI comprises at least one intron, then that at least one intron is present in a highly conserved region of the first nucleotide sequence or the NOI. Here, the term "intron" is used in its normal sense as meaning a nucleotide sequence lying within a coding sequence but being removable therefrom.

We believe that this is the first time that it has been disclosed or suggested that a gene or gene product that is potentially detrimental to a prokaryote—such as a bacterium—can be inactivated in a prokaryote by the insertion of at least one intron into the gene, especially when the at least one intron is inserted into a conserved region of the gene, more especially when the at least one intron is inserted into a conserved region of a coding region of the gene.

Thus, the present invention also provides a process of inactivating a gene or gene product that is potentially detrimental to a prokaryote when present in the prokaryote by the insertion of at least one intron into the gene thereby inactivating the gene or the gene product vis-à-vis the prokaryote.

Preferably, the present invention also provides a process of inactivating a gene or gene product that is potentially detrimental to a prokaryote when present in the prokaryote by the insertion of at least one intron into the gene thereby inactivating the gene or the gene product, wherein the at least one intron is inserted into a conserved region of the gene.

Alternatively expressed: this aspect of the present invention concerns a process comprising converting a gene or product thereof that is potentially detrimental to a prokaryote to an altered gene or product thereof that is not potentially detrimental to the prokaryote, the process comprising the step of inserting at least one intron into the potentially detrimental gene and in such a manner that the altered gene is formed, preferably wherein the at least one intron is inserted into a conserved region of the gene, more preferably when the at least one intron is inserted into a conserved region of a coding region of the gene.

The present invention also provides a prokaryote comprising a gene that would have been potentially detrimental to a prokaryote when present in the prokaryote, but wherein the gene comprises at least one intron thereby inactivating the gene or the product thereof in the prokaryote.

Preferably, the present invention also provides a prokaryote comprising a gene that would have been potentially detrimental to a prokaryote when present in the prokaryote, but wherein the gene comprises at least one intron thereby inactivating the gene or the product thereof in the prokaryote; and wherein the at least one intron is inserted into a conserved region of the gene, more preferably when the at least one intron is inserted into a conserved region of a coding region of the gene.

The present invention also encompasses products obtainable from the expression of such an altered gene.

In a highly preferred embodiment of this particular aspect of the present invention there is provided a nucleotide sequence shown as SEQ ID No. 2 or a variant, homologue or fragment thereof or a sequence that is complementary thereto. This nucleotide sequence corresponds to the coding region of the nag B gene (see SEQ ID No. 1) but wherein inter alia an intron is present in the sequence. The present invention also covers a construct, vector, plasmid, or transgenic organism (or organ or tissue or cell thereof comprising or expressing this nucleotide sequence. Preferably, the organism is a plant, or cell or tissue thereof.

The present invention also covers the nucleotide sequence shown as SEQ ID No. 2 or a variant, homologue or fragment thereof or a sequence that is complementary thereto when operably linked to and is under the control of a promoter that allows expression of the nucleotide sequence. In this aspect, the promoter may be a cell or tissue specific promoter. If, for example, the organism is a plant then the promoter can be one that affects expression of the nucleotide sequence in any one or more of seed, sterm, sprout, root and leaf tissues.

The term "promoter" is used in the normal sense of the art, e.g. an RNA polymerase binding site in the Jacob-Mond theory of gene expression.

The promoter could additionally include one or more features to ensure or to increase expression in a suitable host. For example, the features can be conserved regions such as a Pribnow Box or a TATA box. The promoters may even contain other sequences to affect (such as to maintain, enhance, decrease) the levels of expression of the nucleotide sequence of the present invention. For example, suitable other sequences include the Shl-intron or an ADH intron. Other sequences include inducible elements—such as temperature, chemical, light or stress inducible elements.

Also, suitable elements to enhance transcription or translation may be present. An example of the latter element is the TMV 5' signal sequence (see Sleat Gene 217 [1987] 217–225; and Dawson Plant Mol. Biol. 23 [1993] 97).

The terms "variant", "homologue" or "fragment" in relation to the amino acid sequence for the preferred enzyme of the present invention include any substitution of, variation of, modification of, replacement of, deletion of or addition of one (or more) amino acid from or to the sequence providing the resultant enzyme has glucosamine-6-phosphate deaminase activity, preferably having at least the same activity of the enzyme shown as SEQ ID No. 3. In particular, the term "homologue" covers homology with respect to structure and/or function. With respect to sequence homology, preferably there is at least 75%, more preferably at least 85%, more preferably at least 90% homology to the sequence shown as SEQ ID No. 3. More preferably there is at least 95%, more preferably at least 98%, homology to the sequence shown as SEQ ID No. 3.

The terms "variant", "homologue" or "fragment" in relation to the nucleotide sequence coding for the preferred enzyme of the present invention include any substitution of, variation of, modification of, replacement of, deletion of or addition of one (or more) nucleic acid from or to the sequence providing the resultant nucleotide sequence codes for or is capable of coding for an enzyme having glucosamine-6-phosphate deaminase activity, preferably having at least the same activity of the enzyme encoded by the sequences shown as SEQ ID No. 1 or SEQ ID No. 2. In particular, the term "homologue" covers homology with respect to structure and/or function providing the resultant nucleotide sequence codes for or is capable of coding for an enzyme having glucosamine-6-phosphate deaminase activity. With respect to sequence homology, preferably there is at least 75%, more preferably at least 85%, more preferably at least 90% homology to the sequence shown as SEQ ID No. 1 or SEQ ID No. 2. More preferably there is at least 95%, more preferably at least 98%, homology to the sequence shown as SEQ ID No. 1 or SEQ ID No. 2. However, preferably, a "variant", "homologue" or "fragment" of SEQ ID No. 2 does not include the nucleotide sequence shown as SEQ ID No. 1 on its own.

Preferably, a "variant", "homologue" or "fragment" of SEQ ID No. 2 includes the nucleotide sequence shown as SEQ ID No 1 but wherein at least one intron is present in the sequence.

Preferably, a "variant", "homologue" or "fragment" of SEQ ID No. 2 includes the nucleotide sequence shown as SEQ ID No. 1 but wherein at least one intron is present in a conserved region of the sequence. Preferably, the intron is inserted into a region which encodes a conserved amino acid sequence. Preferably, that conserved amino acid sequence is VVTFNMDEY SEQ ID NO:4.

The terms "variant", "homologue" or "fragment" are synonymous with allelic variations of the sequences.

The term "variant" also encompasses sequences that are complementary to sequences that are capable of hydridising to the nucleotide sequences presented herein. In this respect, preferably the term "variant" encompasses sequences that are complementary to sequences that are capable of hydridising under stringent conditions (e.g. 65° C. and 0.1 SSC) to the nucleotide sequences presented herein.

The present invention also covers nucleotide sequences that can hybridise to the nucleotide sequence of the present invention.

The term "homology" as used herein can be equated with the term "identity". Relative sequence homology (i.e. relative sequence identity) can be determined by commercially available computer programs that can calculate % homology between two or more sequences. A typical example of such a computer program is CLUSTAL.

The term "vector" includes expression vectors and transformation vectors.

The term "expression vector" means a construct capable of in vivo or in vitro expression.

The term "transformation vector" means a construct capable of being transferred from one species to another—such as from an E.coli plasmid to an Agrobacterium to a plant.

The term "tissue" includes tissue per se and organ.

The term "organism" in relation to the present invention includes any organism that could comprise the nucleotide sequence coding for the enzyme according to the present invention and/or products obtained therefrom, and/or wherein the nucleotide sequence according to the present invention can be expressed when present in the organism. Preferably the organism is a plant.

The term "transgenic organism" in relation to the present invention includes any organism that comprises the nucleotide sequence coding for the enzyme according to the present invention and/or products obtained therefrom and/or wherein the nucleotide sequence according to the present invention can be expressed within the organism. Preferably the nucleotide sequence is incorporated in the genome of the organism. Preferably the transgenic organism is a plant.

In a highly preferred embodiment, the transgenic organism (or part thereof) does not comprise the combination of a promoter and the nucleotide sequence coding for the enzyme according to the present invention, wherein both the promoter and the nucleotide sequence are native to that organism (or part thereof) and are in their natural environment. Thus, in this highly preferred embodiment the present invention does not cover the native nucleotide coding sequence according to the present invention in its natural environment when it is under the control of its native promoter which is also in its natural environment. In addition, in this highly preferred embodiment, the present invention does not cover the native enzyme according to the present invention when it is in its natural environment and when it has been expressed by its native nucleotide coding sequence which is also in its natural environment and when that nucleotide sequence is under the control of its native promoter which is also in its natural environment. In other words, it is preferred that the nucleotide sequence is heterologous to the organism and/or is under the control of a heterologous promoter.

As mentioned above, the method of the present invention is particularly suitable for the selection of genetically transformed plant cells, thereby allowing identification and isolation of such cells without being essentially dependent on the use of selection genes coding for antibiotic or herbicide resistance.

The selection method of the present invention may be used for selecting cells in vitro. However, the selection method of the present invention may also be employed in vivo in the sense that it is possible to selectively grow transformed organisms—such as plants—from cells, tissues etc. that comprise the selection system of the present invention.

In vivo use of the selection method of the present invention is of particular importance in connection with genetic transformation performed on whole plants or on plant parts, in which the plants or plant parts comprise both transformed and non-transformed cells, since selection of the transformed cells can, in some instances, be achieved without directly damaging the neighbouring non-transformed cells. For example, in some instances, the transformed cells have a selective advantage compared to the non-transformed cells—such as the ability to form shoots—but the non-transformed cells do not suffer any severe disadvantage in the sense of being damaged or killed, as is the case with using antibiotics or herbicides.

In certain cases, such as when an improved selection frequency is desired, it may be advantageous for the cells to be transformed with a nucleotide sequence that is a selection gene different to the first nucleotide sequence. This additional, selection nucleotide sequence may be an additional gene coding for an enzyme (or other protein or polypeptide) suitable for selection according to the present invention, or it may be a gene coding for an enzyme (or other protein or polypeptide) for a known selection method, eg coding for resistance to a antibiotic or herbicide or it may be a gene suitable for selection by the selection methods described in WO 93/05163 and/or WO 94/20627. Thus, genetically transformed cells may be selected using a combination of selection techniques. For example, if the transformed cells also possessed genes coding for resistance to at least one antibiotic or herbicide, then the medium could additionally comprise at least one antibiotic or herbicide to which the transformed cells are resistant. In particular, we have found that the medium of the present invention does not impair the effectiveness of the known selection methods that rely on herbicide or antibiotic resistance.

The selective advantage possessed by the transformed cells of the present invention may be any difference or advantage with regard to the non-transformed cells which allows the transformed cells to be readily identified and isolated from the non-transformed cells. This may, for example, be a difference or advantage allowing the transformed cells to be identified by simple visual means, i.e. without the use of a separate assay to determine the presence of a gene that provides the selection means.

As mentioned above, one aspect of the present invention relates to genetically transformed cells which have been selected according to the above method, in particular plant cells, as well as plants, progeny or seeds derived from or derivable from such genetically transformed plant cells. In particular, it is often an advantage that these cells are genetically transformed plant cells whose genome does not contain an introduced (i.e. non-native) nucleotide sequence coding for toxin-resistance, antibiotic-resistance or herbicide-resistance as a selection means. As explained above, there are concerns about whether it is safe to incorporate genes coding for eg antibiotic resistance in eg food plants. Genetically transformed plant cells selected by the method of the present invention which do not contain selection genes for eg antibiotic resistance, as well as plants, progeny and seeds derived from such cells, are therefore clearly advantageous in this respect.

The transformed cells may be prepared by techniques known in the art. For example, if the transformed cells are transformed plant cells reference may be made to EP-B-0470145 and CA-A-2006454.

Even though the selection method according to the present invention is not disclosed in EP-B-0470145 and CA-A-2006454, those two documents do provide some useful background commentary on the types of techniques that may be employed to prepare the transformed plant cells and transgenic plants according to the present invention. Some of these background teachings are now included in the following commentary.

The basic principle in the construction of genetically modified plants is to insert genetic information in the plant genome so as to obtain a stable maintenance of the inserted genetic material.

Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205–225) and Christou (Agro-Food-Industry Hi-Tech Mar./Apr. 17–27, 1994).

Thus, in one aspect, the present invention relates to a vector system which carries a first nucleotide sequence or construct according to the present invention and which is capable of introducing the nucleotide sequence or construct into the genome of an organism, such as a plant.

The vector system may comprise one vector, but it can comprise at least two vectors. In the case of two vectors, the vector system is normally referred to as a binary vector system. Binary vector systems are described in further detail in Gynheung An et al. (1980), Binary Vectors, *Plant Molecular Biology Manual* A3, 1–19.

One extensively employed system for transformation of plant cells with a given promoter or nucleotide sequence or construct is based on the use of a Ti plasmid from *Agrobacterium tumefaciens* or a Ri plasmid from *Agrobacterium rhizogenes* (An et al. (1986), *Plant Physiol.* 81, 301–305 and Butcher D. N. et al. (1980), *Tissue Culture Methods for Plant Pathologists,* eds.: D. S. Ingrams and J. P. Helgeson, 203–208).

Several different Ti and Ri plasmids have been constructed which are suitable for the construction of the plant or plant cell constructs described above.

The first nucleotide sequence or construct of the present invention should preferably be inserted into the Ti-plasmid between the border sequences of the T-DNA or adjacent a T-DNA sequence so as to avoid disruption of the sequences immediately surrounding the T-DNA borders, as at least one of these regions appear to be essential for insertion of modified T-DNA into the plant genome.

As will be understood from the above explanation, if the organism is a plant, then the vector system of the present invention is preferably one which contains the sequences necessary to infect the plant (e.g. the vir region) and at least one border part of a T-DNA sequence, the border part being located on the same vector as the genetic construct. Preferably, the vector system is an *Agrobacterium tumefaciens* Ti-plasmid or an *Agrobacterium rhizogenes* Ri-plasmid or a derivative thereof as these plasmids are well-known and widely employed in the construction of transgenic plants, many vector systems exist which are based on these plasmids or derivatives thereof.

In the construction of a transgenic plant the promoter or nucleotide sequence or construct of the present invention may be first constructed in a microorganism in which the vector can replicate and which is easy to manipulate before insertion into the plant. An example of a useful microorganism is *E. coli.,* but other microorganisms having the above properties may be used. When a vector of a vector system as defined above has been constructed in *E. coli.* it is transferred, if necessary, into a suitable Agrobacterium strain, e.g. *Agrobacterium tumefaciens.* The Ti-plasmid harbouring the first nucleotide sequence or construct of the invention is thus preferably transferred into a suitable Agrobacterium strain, e.g. *A. tumefaciens,* so as to obtain an Agrobacterium cell harbouring the promoter or nucleotide sequence or construct of the invention, which DNA is subsequently transferred into the plant cell to be modified.

As reported in CA-A-2006454, a large number of cloning vectors are available which contain a replication system in *E. coli* and a selection means which allows a selection of the transformed cells. The vectors contain for example pBR322, the pUC series, the M13 mp series, pACYC 184 etc. In this way, the promoter or nucleotide or construct of the present invention can be introduced into a suitable restriction position in the vector. The contained plasmid is used for the transformation in *E.coli.* The *E.coli* cells are cultivated in a suitable nutrient medium and then harvested and lysed. The plasmid is then recovered and then analysed—such as by any one or more of the following techniques: sequence analysis, restriction analysis, electrophoresis and further biochemical-molecular biological methods. After each manipulation, the used DNA sequence can be restricted or selectively amplified by PCR techniques and connected with the next DNA sequence. Each sequence can be cloned in the same or different plasmid.

After each introduction method of the first nucleotide sequence or construct according to the present invention in the plants the presence and/or insertion of further DNA sequences may be necessary. If, for example, for the transformation the Ti- or Ri-plasmid of the plant cells is used, at least the right boundary and often however the right and the left boundary of the Ti- and Ri-plasmid T-DNA, as flanking areas of the introduced genes, can be connected. The use of T-DNA for the transformation of plant cells has been intensively studied and is described in EP-A-120516; Hoekema, in: The Binary Plant Vector System Offset-drukkerij Kanters B. B., Alblasserdam, 1985, Chapter V; Fraley, et al., Crit. Rev. Plant Sci., 4:1–46; and An et al., EMBO J. (1985) 4:277–284.

Direct infection of plant tissues by Agrobacterium is a simple technique which has been widely employed and which is described in Butcher D. N. et al. (1980), *Tissue Culture Methods for Plant Pathologists,* eds.: D. S. Ingrams and J. P. Helgeson, 203–208. For further teachings on this topic see Potrykus (Annu Rev Plant Physiol Plant Mol Biol [1991] 42:205–225) and Christou (Agro-Food-Industry Hi-Tech Mar./Apr. 17–27, 1994). With this technique, infection of a plant may be done on a certain part or tissue of the plant, i.e. on a part of a leaf, a root, a stem or another part of the plant.

Typically, with direct infection of plant tissues by Agrobacterium carrying the first nucleotide sequence or the construct, a plant to be infected is wounded, e.g. by cutting the plant with a razor or puncturing the plant with a needle or rubbing the plant with an abrasive. The wound is then inoculated with the Agrobacterium. The inoculated plant or plant part is then grown on a suitable culture medium.

When plant cells are constructed, these cells are grown and, optionally, maintained in a medium according to the present invention following well-known tissue culturing methods—such as by culturing the cells in a suitable culture medium supplied with the necessary growth factors such as amino acids, plant hormones, vitamins, etc, but wherein the culture medium comprises a component according to the present invention. Regeneration of the transformed cells into genetically modified plants may be accomplished using known methods for the regeneration of plants from cell or tissue cultures, for example by selecting the transformed shoots and by subculturing the shoots on a medium containing the appropriate nutrients, plant hormones, etc.

Further teachings on plant transformation may be found in EP-A-0449375.

Reference may even be made to Spngstad et al (1995 Plant Cell Tissue Organ Culture 40 pp 1–15) as these authors present a general overview on transgenic plant construction.

In a highly preferred embodiment, the present invention is based on our finding that it is possible to use constructs comprising an expressable gene coding for glucosamine-6-phosphate deaminase to prepare transformed cells wherein the transformed cells can be selected from non-transformed cells.

In addition, the present invention also covers transgenic plants comprising the transformed cells or constructs of the present invention.

Thus, in a highly preferred embodiment the present invention covers transgenic plants comprising transformed cells or constructs that comprise an expressable gene coding for glucosamine-6-phosphate deaminase.

In order to explain in more detail these highly preferred aspects of the present invention, reference shall be made to at least FIGS. 1–11.

In this regard, glucosamine in low concentrations (typically in μ-molar concentrations) is metabolised to N-acetyl glucosamine ("NAGA"), which in turn is metabolised to N-acetyl glucosamine 6-phosphate ("NAG6P"), which in turn is metabolised to N-acetyl glucosamine 1-phosphate, which in turn is metabolised to UDP-N-acetyl glucosamine. UDP-N-acetyl glucosamine is a useful biological precursor for glycoproteins (Roberts, R M, Plant Physiol, 45: 263–267). This metabolic pathway is schematically shown in FIG. 1. Hence, in low concentrations, glucosamine is a nutrient for plant cells.

However, glucosamine in high concentrations (typically in milli-molar concentrations) is metabolised to glucosamine-6-phosphate ("GA6P"). This is because when glucosamine is supplied in milli-molar concentrations, the levels of this sugar come within the Km range of hexokinase and, in doing so, phosphorylation occurs to form glucosamine 6-phosphate. This metabolic pathway is schematically shown in FIG. 1.

Thus, administration of micro-molar amounts of glucosamine to plant cells leads to formation of NAGA which can be further metabolised; whereas provision of milli-molar amounts of glucosamine leads to an accumulation of GA6P which is undesirable in non-transformed cells (Chen-She, S (1995), New Phytologist 74: 383–392). In this regard, and unlike NAGA, GA6P is not a nutrient for natural plant cells. In fact, GA6P is toxic to natural plant cells. In this regard, the presence of GA6P renders plant cells less hardy. In some instances, the cells may even die as GA6P does not readily enter plant metabolic pathways. Hence, in high concentrations, metabolism of glucosamine produces a metabolite the accumulation of which is toxic for the non-transformed plant cells.

In accordance with the present invention, we then found that GA6P could be enzymatically converted in plant cells to a nutrient. In particular, we found that the enzyme glucosamine-6-phosphate deaminase (such as the enzyme encoded by the nag B gene) could convert GA6P to fructose 6-phosphate ("F6P") in plant cells. This metabolic pathway is schematically shown in FIG. 2.

As it is well known, F6P is a very beneficial biological substrate as it is a component of the Embden Meyerhof pathway. Hence, in high concentrations, a potentially toxic metabolite of glucosamine can be enzymatically converted to a beneficial nutrient for plant cells. This enzymatic conversion forms the basis of one aspect of the selection method of the present invention.

It is known that the metabolism of glucosamine 6-phosphate by Escherichia coli is facilitated by the enzyme glucosamine 6-phosphate deaminase (EC 5.3.1.10). This enzyme simultaneously catalyses deamination and aldoketose isomerisation to form fructose 6-phosphate (Wolfe, J B & Nakada, H I (1956) Arch Biochem Biophys 64: 489–497. Wolfe J B, et al (1957) Arch Biochem Biophys 66: 333–339). Nevertheless, it has not been suggested before that such an enzyme could be used as a feature of a selection method, let alone be expressed in plant cells.

Of interest, even though the conversion of GA6P to F6P results in the release of $NH_3$—which in high yields is toxic to plants—we have found that the plant cells are not detrimentally affected. Hence, despite the release of a potentially toxic by-product in the highly preferred selection method of the present invention, that release does not detrimentally affect the overall selection method. This result was highly surprising.

One aspect of the selection method of the present invention provides an additional advantageous feature. In this regard, NAG6P has a positive effect (an allosteric effect) on the conversion of GA6P to F6P by the enzyme glucosamine-6-phosphate deaminase encoded by nagB. This aspect of the present invention is schematically shown in FIG. 3. This surprising finding is in accordance with studies done with E. coli (Calcagno, M, et al (1984) Biochim Biophys Acta 787: 165–173). Thus, should any glucosamine be metabolised to NAGA and in turn eventually to NAG6P then that NAG6P would ensure conversion of GA6P to F6P by the enzyme glucosamine-6-phosphate deaminase or at least aid the conversion step. This is an advantageous feature of the highly preferred selection method of the present invention.

In a preferred aspect of the present invention, an intron is inserted in to the gene encoding glucosamme-6-phosphate deaminase, in particular into a highly conserved region thereof. This modification was done to minimise or to eliminate the detrimental, degradative effect of glucosamine-6-phosphate deaminase on the cell walls of bacteria such as Agrobacterium. As Agrobacterium is often the vector of choice to transform plant cells, it may be necessary to inactivate the glucosamine-6-phosphate deaminase vis-a-vis the bacterium, but not vis-a-vis the plant cells. This inactivation can be achieved by insertion of an intron into the gene coding for the glucosamine-6-phosphate deaminase. In particular, inactivation can be achieved by insertion of an intron into a conserved region of the gene coding for the glucosamine-6-phosphate deaminase.

In this regard, FIG. 4 shows sequences coding for glucosamine-6-phosphate deaminase from Candida albicans (nag 1 gene) SEQ ID NO:5 and glucosamine-6-phosphate deaminase from E. coli (nag B gene) SEQ ID NO:3. In our studies, we chose to insert the intron within the region of the gene that encodes a conserved amino acid sequence, in this case the amino acid sequence VVTFNM-DEY SEQ ID NO:4.

Also, FIGS. 5, 6 and 7 schematically present the cloning procedure adopted.

FIGS. 8, 9, 10 and 11 present schematic diagrams of the resultant plasmids.

The following samples were deposited in accordance with the Budapest Treaty at the recognised depositary The National Collections of Industrial and Marine Bacteria Limited (NCIMB) at 23 St. Machar Drive, Aberdeen, Scotland, United Kingdom, AB2 1RY on Jan. 10, 1997:

1. E.coli DH5α containing plasmid pVictorIV GNG E35S nagB IV2. The deposit number is NCIMB 40852. This plasmid comprises the nagB gene with an intron.
2. E.coli DH5α containing plasmid pVictorIV GNG rbc nagB IV2. The deposit number is NCIMB 40853. This plasmid comprises the nagB gene with an intron.
3. E.coli DH5α containing plasmid pVictorIV GNG nagB. The deposit number is NCIMB 40854. This plasmid comprises the nagB gene without an intron.

Highly preferred aspects of the present invention therefore relate to first nucleotide sequences according to the present invention obtainable from those deposits, including expression vectors, constructs, organisms and transgenic organisms comprising those same sequences or plasmids.

The present invention also encompasses a selection means capable of enabling the selection of a transformed cell over a non-transformed cell, wherein the selection means is obtainable from each of those deposits.

For example the present invention encompasses a selection means that is obtainable from deposit number NCIMB 40854. In this regard, the selection means (i.e. the selection means capable of enabling the selection of a transformed cell over a non-transformed cell) may be obtained from this deposit by PCR amplification techniques (such as those mentioned below) and using the following primers:

5'-(B134) (38-mer)
TAAGATCTAAACAACAACATGAGACT-GATCCCCCTGAC (SEQ ID NO:6)
3'-(B137) (28-mer)
ACCTCGAGCAGGGATAACAATTACAGAC (SEQ ID NO:7)

By way of further example, the present invention encompasses a selectaion means capable of enabling the selection of a transformed cell over a non-transformed cell, wherein the selection means is obtainable from deposit number NCIMB 40852 or 40853. In this regard, the selection means may be obtained from this deposit by PCR amplification techniques (such as those mentioned below) and using the following primers:

Primer 1 (B507) 29'MER
TGCAGAGATCTAAACAACAACATGAGACT (SEQ ID NO:8)
Primer 6 (B351) 27'MER
CATGCCTCGAGCAGGGATAACAATTAC (SEQ ID NO:9)

BRIEF DESCRIPTION OF THE DRAWINGS

The present invention will now be described only by way of examples, in which reference may be made to the following Figures:

FIG. 4, which presents a comparison of nucleotide sequences;

FIG. 5, which presents some nucleotide sequences;

FIG. 7, which presents a schematic diagram of a PCR reaction scheme;

FIG. 28, which presents three sequence listings according to the present invention.

Initially, it is to be noted that FIG. 28 presents a number of sequences according to the present invention. In this regard, SEQ ID No. 1 is the nucleotide sequence of the nagB gene encoding glucosamine-6-phosphate deaminase. SEQ ID No. 2 corresponds to the nucleotide sequence of the nagB gene that encodes glucosamine-6-phosphate deaminase but wherein inter alia an intron is present in the sequence. SEQ ID No. 2 is sometimes referred to as nagB IV2. SEQ ID No. 3 corresponds to amino acid sequence of glucosamine-6-phosphate deaminase—which is sometimes referred to as nagB.

DETAILED DESCRIPTION OF THE PREFERRED EMBODIMENT

Preparation of Constructs

Figure 22:
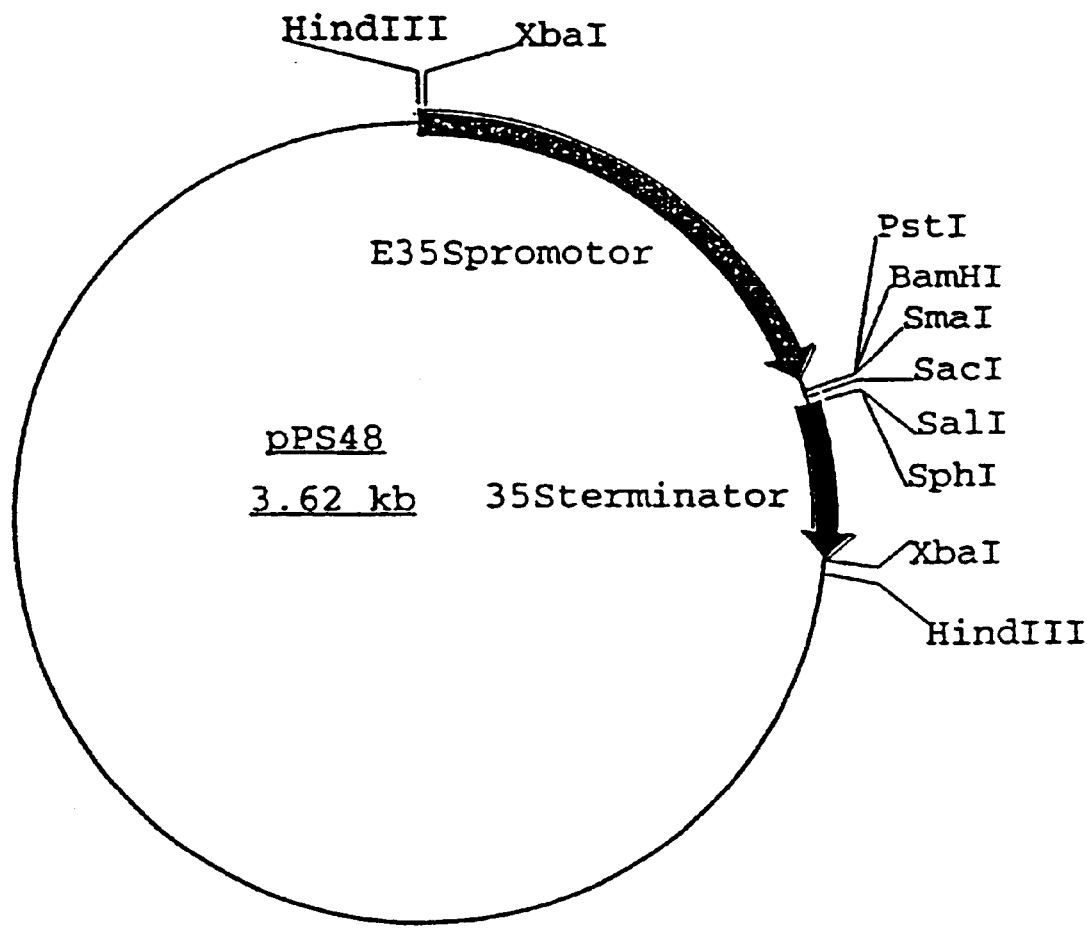
FIG. 22, which presents a schematic diagram of a plasmid.

The coding region of the nagB gene is amplified from the plasmid pUC nagB (Altimaro, M M, et al (1991) BBA 1076 266–272) by PCR. The upstream PCR primer contains a BglII site. The downstream PCR primer contains an XhoI site. Cleavage of the PCR product with these enzymes allows directional cloning of the amplified fragment between the cohesive BamHI and SalI sites of the plasmid pPS48 (see FIG. 22). The resulting construction locates the nagB coding region between the twin CaMV 35S promoter and the CaMV 35S terminator.

Since the 35S promoter is also functional in *E coli* (Bilang, et al, Gene 100 (1991) 247–250), selection of transformants is accomplished by complementation of the nagB-deficient mutant strain IBPC S71CR. This strain has the genotype IBPC 5321 nagB2, asnB50:Tn5, recA1, snl:Tn10. The selection is performed on plates containing n-acetyl glucosamine as a fermentable carbon source.

Amplification of nagB Coding Region
Primers:
5'-(B134) (38-mer)
TA<u>AGATCT</u>AAACAACAACA TGAGACTGATC-CCCCTGAC (SEQ ID NO:6)

The BGlII site is shown as underlined text; the plant upstream region is shown in bold text; and the start codon is shown in italics.

3'-(B137) (28-mer)
AC<u>CTCGAG</u>CAGGGATAACAATTACAGAC (SEQ ID NO:7)

The XhoI site is shown as underlined text; and the stop codon is shown in bold text.

Both of the primers were synthesised with "trityl-ON" and purified on C.O.P cartridges according to the supplier's (Cruachem Ltd, Glasgow, UK—Brochure marked USIN-001-RO2) instructions except that Step 12 was substituted with the following step: The sample was loaded on to a Phamiacia NAP5 column and eluted step wise with 500 μl aliquots of water, the 500 μl aliquots were collected and the $OD_{260}$ determined to locate the oligonucleotides.

Amplification Reaction Mixture

10 μl Amplitaq 10×buffer without Mg

8 μl 25 mM $MgCl_2$

77 μl water 0.5 μl pUC nagB plasmid miniprep 0.76 μl 5'-(B134)

0.91 μl 3'-(B137)

2 μl dNTP mixture (2.5 mM of each)

0.5 μl Amplitaq

Single primer controls adjusted to the same volume with water were also run.

Amplification Reaction Conditions

| Cycle | Block 1 | Block 2 | Block 3 |
|---|---|---|---|
| 1 | 94° C. - 5 mins | 94° C. - 5 mins | 94° C. - 5 mins |
| 2–29 | 94° C. - 1.5 mins | 94° C. - 1.5 mins | 94° C. - 1.5 mins |
|  | 50° C. - 2 mins | 55° C. - 2 mins | 60° C. - 2 mins |
|  | 72° C. - 2 mins | 72° C. - 2 mins | 72° C. - 2 mins |
| 30 | 94° C. - 1.5 mins | 94° C. - 1.5 mins | 94° C. - 5 mins |
|  | 50° C. - 2 mins | 55° C. - 2 mins | 60° C. - 2 mins |
|  | 72° C. - 10 mins | 72° C. - 10 mins | 72° C. - 10 mins |
| 31 | 4 C. - until collection | 4° C. - until collection | 4° C. - until collection |

PCR was run overnight. Then 5 μl of each PCR reaction mixture were mixed with an equal volume of TE (tris-EDTA) pH 7.5 and 2 μl of gel loading solution. All 12 μl of each mixture were loaded onto a 1.2% w/v agarose gel in ½ TBE and electrophoresed at 35V for two hours. Samples were flanked by 4 μl of Boehringer molecular weight markers III and VI.

Figure 23:
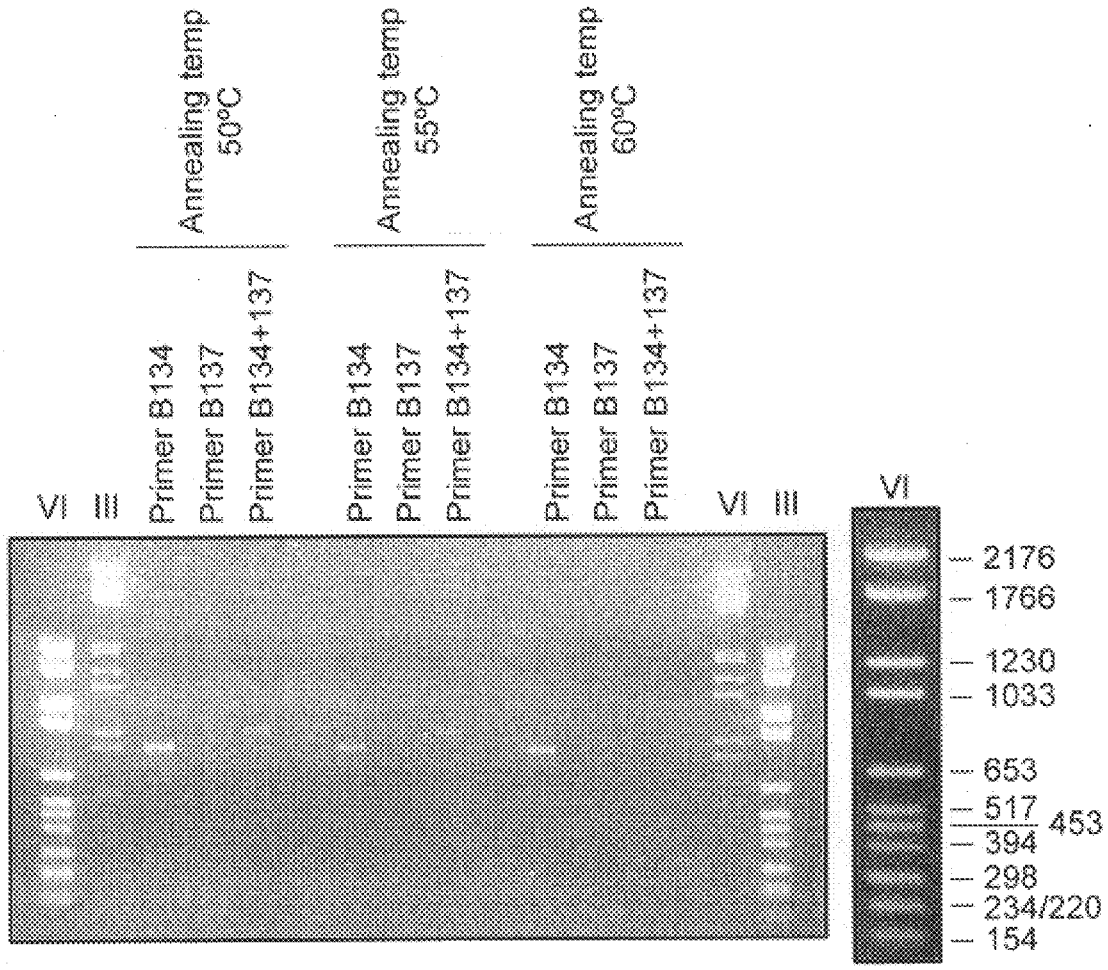
FIG. 23, which presents a photographic result of an electrophoresis study.

The product in the reaction mixture, at all three annealing temperatures, corresponded well with the predicted size of 839 base pairs. The 3'-primer-only control produced an artifactual band of approximately 950 base pairs, which was very weak at 60° C. annealing temperature and absent from the double primer (5'3') reaction (see FIG. 23).

50 μl of the 50° C. annealing temperature double primer (5'3') reaction were then taken and the PCR product purified by Gene Clean II™ (supplied by Bio 101 Inc) treatment using the following protocol.

150 μl NaI mixture was added followed by 15 μl of glass milk. The mixture was vortexed, left to stand on ice for five minutes, and then centrifuged at maximum speed for 20 seconds in an Ole Dich refrigerated centrifuge (4° C.). The pellet was washed three times by resuspension in 400 μl ice-cold New Wash™ (supplied by Bio 101 Inc), and repeating the centrifugation. The pellet was finally resuspended in 15 μl TE pH 7.5, incubated at 50° C. for three minutes and then centrifuged at room temperature in an Eppendorf centrifuge for one minute. The supernatant was collected, and the elution with 15 μl TE pH 7.5 and centrifugation repeated. The resulting supernatant was pooled with the first, and the total volume was 35 μl.

The gene-cleaned PCR product was then cleaved in the following reaction mixture for 18 hours at 37° C.

35 μl gene-cleaned PCR product.

5 μl 10×Boehringer buffer H

5 μl XhoI 10 U/μl

5 μl BglII 10 U/μl

A preparation of pPS48 was sequentially cleaved with SalI and BamHI in the following manner.

The reaction mixture listed below was incubated at 37° C. for four hours.

5 μl pPS48

5 μl 10×Boehringer buffer H

35 μl water

5 μl SalI 50 U/μl

The DNA was purified from the mixture using the gene clean protocol described above. The SalI-cut plasmid was in a final volume of 30 μl TE pH 7.5.

The following reaction mixture was then incubated at 37° C. for four hours.

30 μl SalI pPS48

5 μl 10×Boehringer 10×buffer B

10 μl water

5 μl BamHI 50 U/μl

Figure 24:
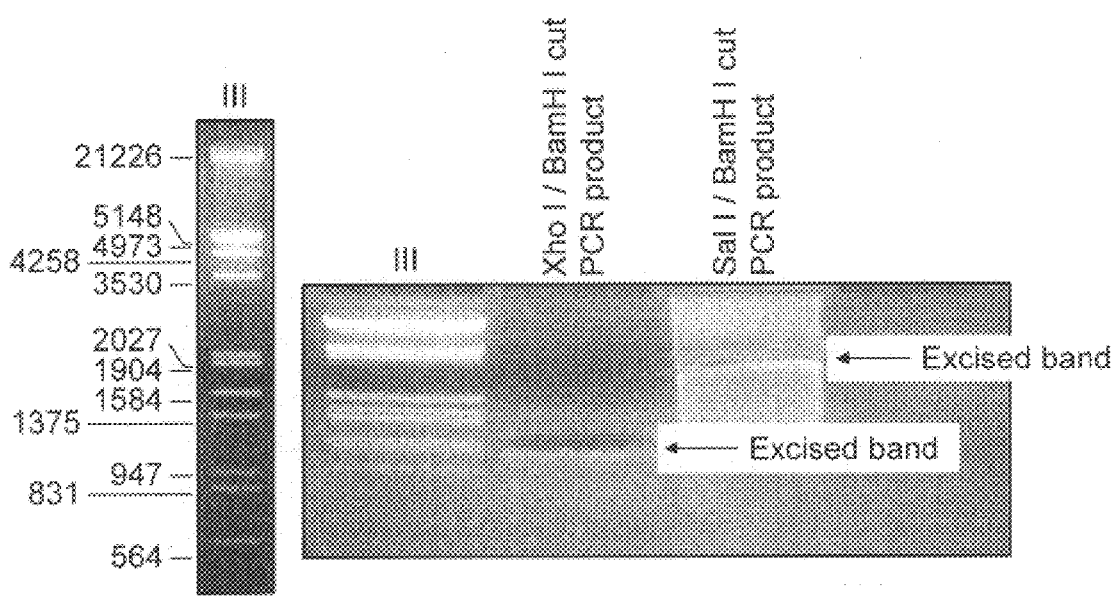
FIG. 24, which presents a photographic result of an electrophoresis study.

10 μl volumes of gel loading solution were added to both the SalI/BamHI-cut pPS48 and the XhoI/BglII-cut PCR product (each in 50 μl). The mixtures were loaded onto a 1.2% w/v agarose gel in IX TAE (triacetic acid and EDTA) with 20 μl of Boehringer molecular weight marker III run in parallel. Electrophoresis at 35V was performed for one hour. The results are shown in FIG. 24.

The bands corresponding to the SalI/BamHI-cut pPS48 (B600 bp) and XhoI/BglII-cut PCR product (839 bp) were excised and weighed in preweighed Eppendorf tubes.

Assuming a density of 1 $g/cm^3$, three volumes of NaI solution were added to each excised band and the samples heated at 50° C. for five minutes. The tubes were vortexed, and returned to 50° C. for a further five minutes. 15 μl of glass milk were added to each and the suspension was vortexed and placed on ice for five minutes. The glass milk was sedimented and washed three times with 400 μl "new wash" as performed in the gene clean protocol described above. Using the purified fragments, the following ligation mixture was incubated at 16° C. for 20 hours.

6 μl XhoI/BglII-cut PCR product

5 μl SalI/BamHI-cut pPS48

4 μl 5×BRL ligation buffer

4 μl water

1 μl T4 ligase (BRL)

A 5 ml culture of E coli IBPC57ICR in LB TET was set up using low salt medium (1% tryptone, 0.5% yeast extract, 0.5% NaCl).

Electrocompetent cells of E coli (glucosamine deaminase deficient) strain IBPC 571CR (IBPC 571CR=IBPC 5321 nagB2, asnB50:Tn5, recA1, sal:Tn10) were prepared as follows.

1. 2 ml of the 5 ml overnight culture were used to inoculate a 500 ml low salt LB TET culture (1% tryptone, 0.5% yeast extract, 0.5% NaCl, 10 μg ml tetracycline—pH not adjusted) pre-warmed to 37° C. in a 2.5 l Erlenmeyer flask on an orbital shaker at 250 rpm. A parallel culture was set up for sampling in order to plot the progress of growth. Both cultures were returned to the 37° C. shaker.

Figure 25:
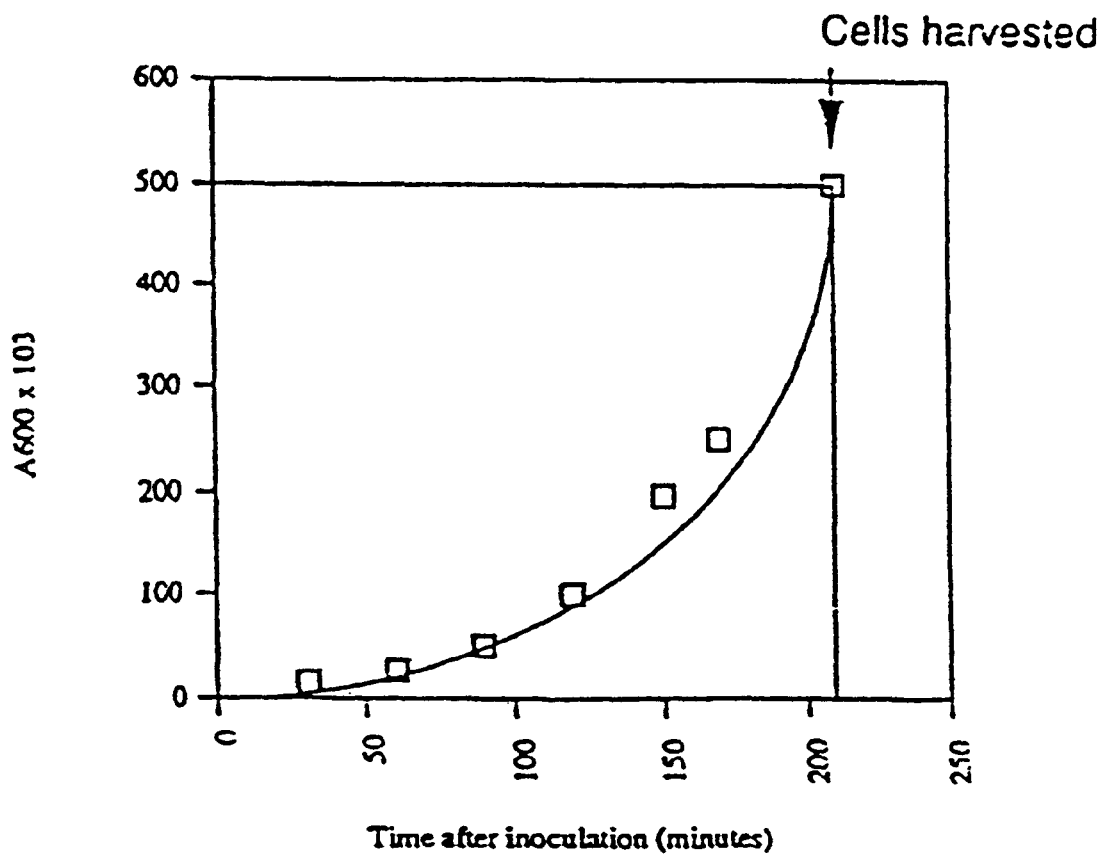
FIG. 25, which presents a graph.

2. A growth curve was plotted (see FIG. 25) and used to predict the time at which $A_{600}$ would reach 0.5, at which time the culture was immediately placed in an ice/water slush, and placed in a cold room (4° C.) for 30 minutes.

3. The culture was divided equally between two sterile 500 ml Beckman centrifuge bottles and centrifuged at 5000 rpm in a JA 10 rotor for 15 minutes at 4° C.

4. The pellets were resuspended in a total of 500 ml cold (4° C.) sterile water and divided equally between centrifuge bottles, before centrifugation as in step 3.

5. The pellets were resuspended in 300 ml cold sterile water (4° C.), divided equally between centrifuge bottles and the centrifugation from step 3 repeated again.
6. Cells were resuspended in 10 ml cold (4° C.) 10% v/s sterile glycerol and divided equally between two snap-capped Falcon tubes which were centrifuged at 6000 rpm for 15 minutes at 4° C. in a Sorvall SM24 rotor.
7. The pellets were resuspended in a total of 1 ml cold (4° C.) sterile 10% v/v glycerol.

A sample was taken for electroporation with the ligation mixture mentioned above and the remainder was frozen in liquid nitrogen as 205 μl aliquots in nunc cryo tubes.

Electrotransformation 1. 1 μl of the ligation mixture was mixed with 40 μl cold sterile water and 40 μl electrocompetent IBPC 571 CR in a cold electroporation cuvette and left on ice for one minute.
2. The Biorad gene pulser apparatus was set to 25 μF, 2.48 kV, 200 W.
3. The cuvette from step 1 was carefully wiped to remove damp from electrode surface contacts and then positioned in the apparatus.
4. The sample was pulsed (4.5 mS), the cuvette immediately removed and 1 ml of SOC was added as rapidly as possible.
5. The contents of the cuvette were transferred to a snap-capped Falcon tube and incubated at 37° C. for one hour on an orbital shaker set at 250 rpm.
6. The contents of the Falcon tube from step 5 were transferred to an eppendorf tube and centrifuged for 30 s at 13000 g. The supernatant was removed and the pellet resuspended in 1 ml sterile water.
7. The following amounts of bacterial suspension from step 6 were spread on to McConkey minimal agar (Difco) containing 1% w/v N-acetyl glucosamine, and 10 μg/ml tetracycline with 50 μg/ml ampicillin.

100 μl undiluted
50 μl transformed suspension+50 μl water
10 μl transformed suspension+90 μl water The plates were incubated for 22 hours at 37° C.

Two positive colonies on the "undiluted" inoculum plate were picked and spread on to fresh McConkey minimal agar (Difco) containing 1% w/v N-acetyl glucosamine, 10 μg/ml tetracycline, and 50 μg/ml ampicillin. The plates were incubated at 37° C. for 22 hours. Isolated colonies from the subcultures from were used to inoculate 5 ml cultures in TB 10 μg/ml tetracycline, 100 μg/ml ampicillin, incubated 16 hours at 37° C. on an orbital shaker at 250 rpm.

The entire volumes of the cultures were then harvested and plasmid minipreps prepared using Qiagen spin columns according to the supplier's (Qiagen) instructions.

The following diagnostic restriction digests were set up for both plasmid minipreps.

Figure 26:
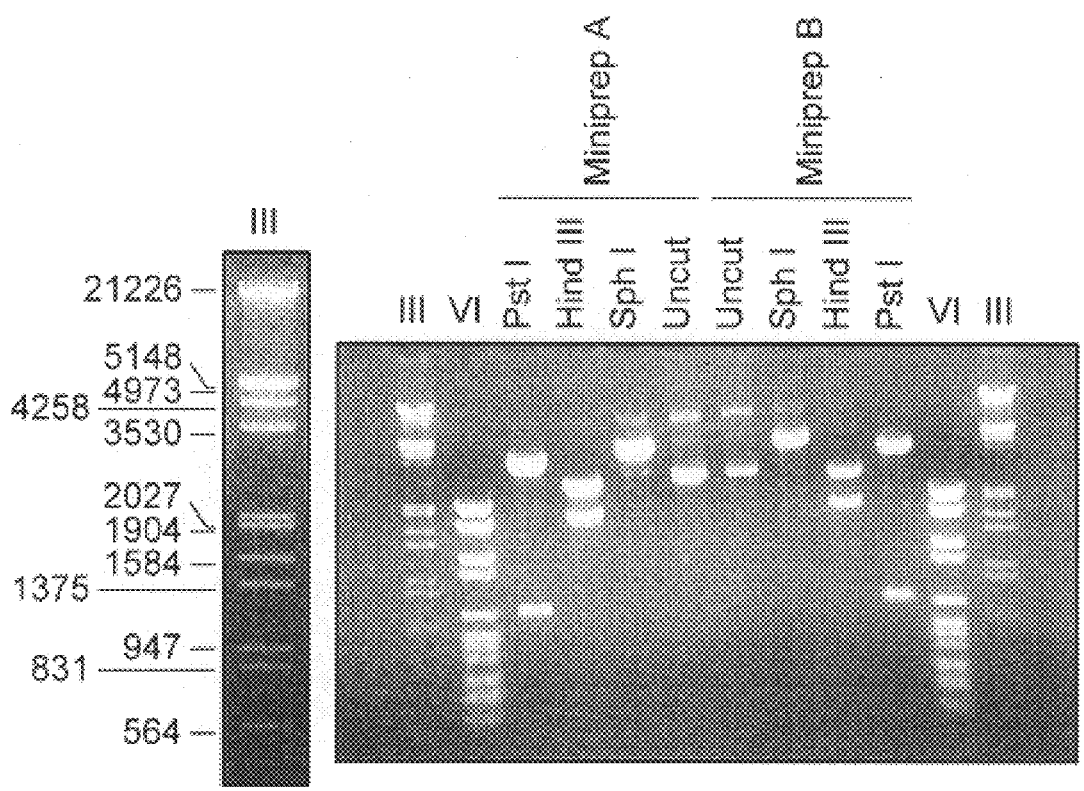
FIG. 26, which presents a photographic result of an electrophoresis study.

1 μl 10×Boehringer buffer H
5 μl water
3 μl plasmid prep
1 μl PstI 10 U/μl
1 μl 10×Boehringer buffer B
5 μl water
3 μl plasmid prep
1 μl HindIII 50 U/μl
1 μl 10×Boehringer buffer M
5 μl water
3 μl plasmid prep
1 SphI 10 U/μl All the above reaction mixtures were incubated at 37° C. for two hours. 2 μl of gel loading solution were added to each and the entire volume loaded on to a 1% w/v agarose gel flanked by Boehringer molecular weight markers III and VI. Electrophoresis was performed in ½ TBE buffer, at 35V for two hours. The results are shown in FIG. 26.

Both minipreps A and B showed identical restriction patterns which are consistent with the ligation of the nagB coding region within the 35S expression cassette of pPS48.

The PstI digest cut in the MCS (multiple cloning site) of pPS48 and at position 634 bp in the coding region of nagB. The contribution of the non-coding upstream region of the 5' PCR primer and A portion of the MCS of pPS48 together with the nagB coding region account for a PstI fragment of 658 bp.

The HindIII digestion excised the entire expression cassette, which without any insert is 970 bp, and incorporating the nagB PCR product (840 bp) is the same value observed—810 bp. Furthermore, the other band of 2.65 kb is consistent with the excision of the 1810 bp fragment from pPS48.

SphI cuts at a unique site within the MCS of pPS48 to give a linear intact construction of 4.45 kb, which is consistent with the cloning of the entire nagB PCR product into pPS48. It is noteworthy that the appearance of a faint band, which is also present in the uncut plasmid tracks, is indicative of incomplete digestion by split.

The following reaction mixture was incubated at 37° C. for six hours, and then placed at 4° C.

Figure 27:
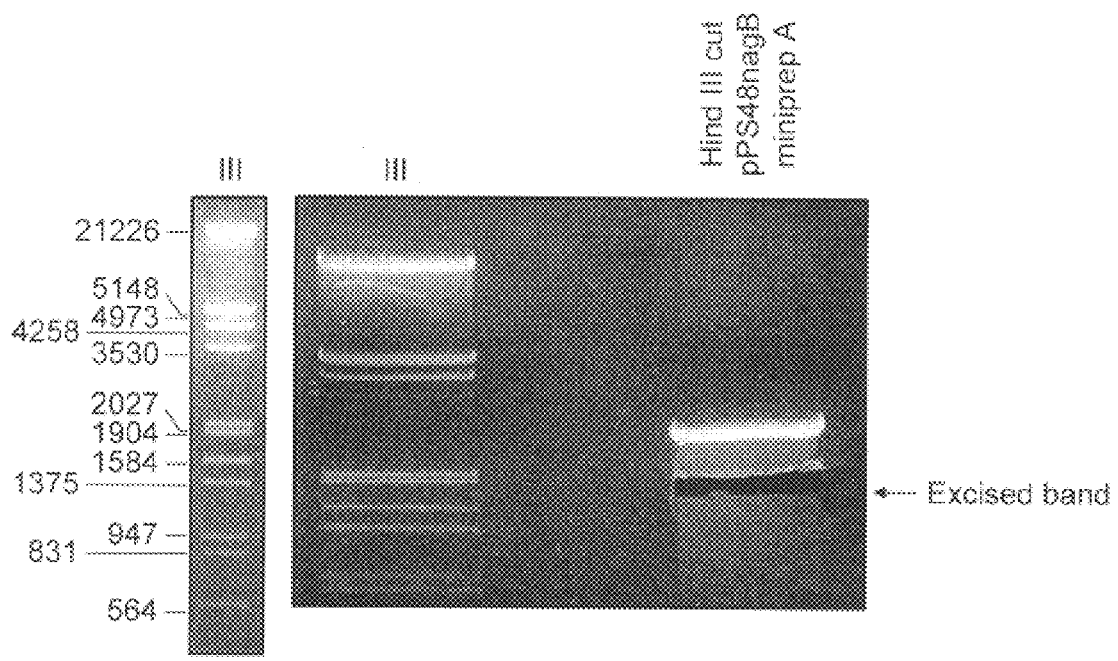
FIG. 27, which presents a photographic result of an electrophoresis study.

15 μl pPS48 nagB miniprep A
1 μl water
2 μl Boehringer 10×buffer B
2 μl Hinds 50 U/μl The HindIII restriction digest of pPS48 nagB was mixed with 4 μl gel loading solution, and electrophoresed in parallel with 20 μl Boehringer molecular weight marker III, in a 1% agarose gel at 35V for one hour, in TAE buffer. The results are shown in FIG. 27. The 1810 bp HindIII fragment was excised from the gel and purified using gene clean II employing the protocols mentioned above.

The purified fragment was then ligated into a plant transformation vector (which is discussed later).

Figure 12:
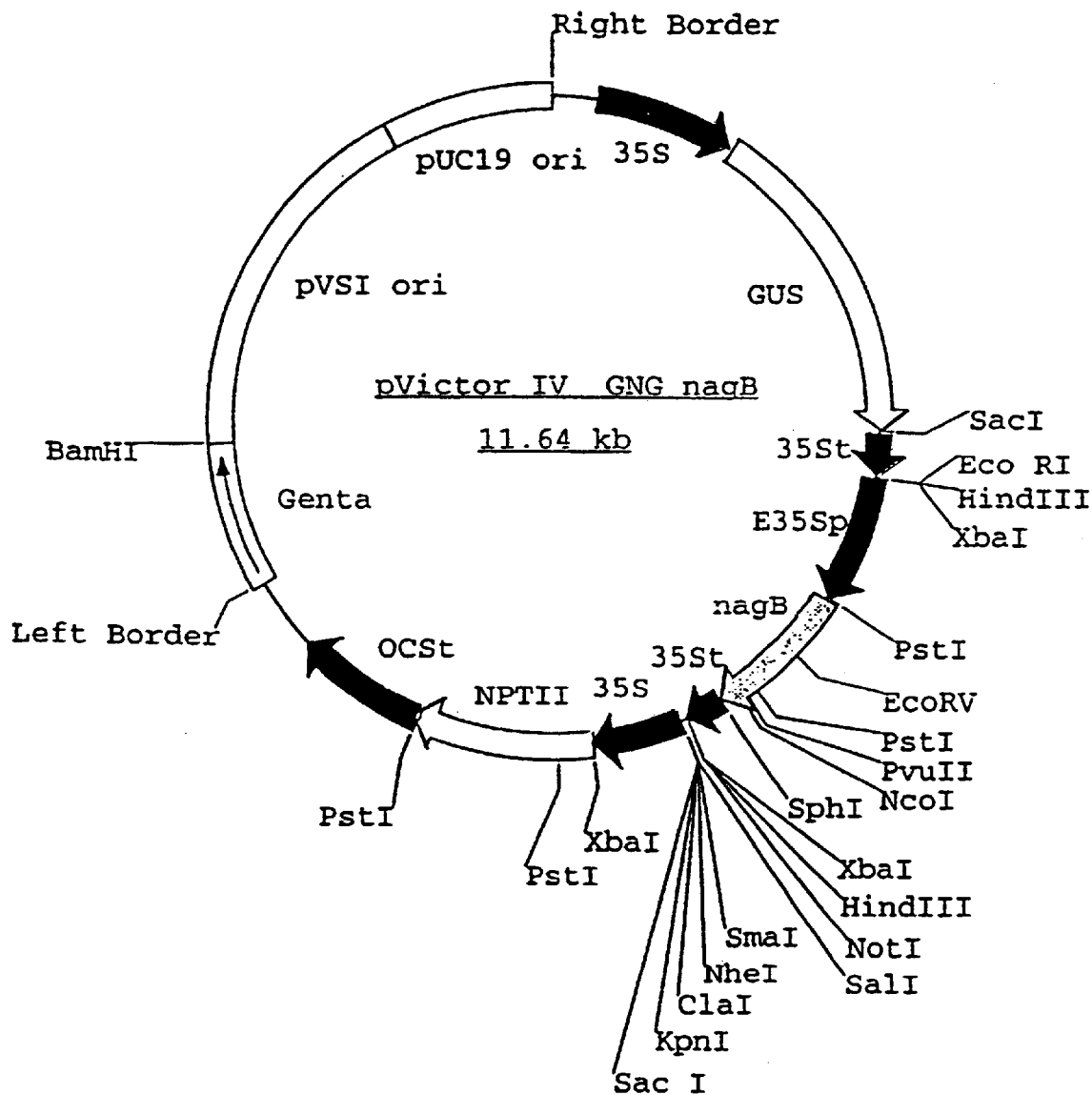
FIG. 12, which presents a schematic diagram of a plasmid.

The 1810 bp HindIII fragment from pPSnagB, containing the coding region of nagB flanked by the 35S expression cassette, was ligated into pVictor IV GNG. The resultant plasmid—pVictor IV GNG nagB—is shown in FIG. 12.

This construction was used to transform *Agrobacterium tumefaciens*. The transformants were found to grow much better on agar plates than when compared to liquid media. By comparison of appropriate control transformations, this was attributed directly to the presence of the nagB gene.

It is likely that the pattern of sensitivity of a *A. tumefaciens* to the presence of pVictor IV GNG nagB results from enhanced turnover of the bacterial cell wall, rendering the bacteria susceptible to the lower osmotic pressure of liquid media. A preferable aspect of the present invention was therefore to prevent adverse expression of nagB in the bacterial transformants, while allowing such expression to occur after it has been integrated into the plant genome.

The strategy employed was based on that used to prevent expression of the histochemical marker gene for β-glucuronidase (uidA) in *A. tumefaciens*, by the insertion of the IV2 intron into the coding region of the gene (Vancanneyt, C et al (1990) Mol Gen Genet 220:245–250). This intron is known to be spliced out of the uidA construct in our target plants, including guar and potato. The site of splicing of the IV2 intron into nagB was chosen to be between the codons for MET70 and ASP71, which lie within a highly conserved region comprising VAL VAL THR PHE ASN MET ASP GLU TYR (SEQ ID NO:4) (Natarajan and Datta Assis (1993) 268 pp 9206–9241). This splice junction conforms to the consensus sequence for plant introns (Shapiro, M B & Senapathy, P (1987) NAR 15 7155–7174). The method chosen to insert the IV2 intron into nagB was SOE (splicing by overlap extension) PCR. Primers and reaction conditions were designed using "OLIGO4" program. (National Biosciences Inc)

PCR Primers

The following primers were used:
Primer 1 (B507) 29'MER
TGCAGAGATCTAAACAACAACATGAGACT (SEQ ID NO:8)

Here the BglII site is shown in bold type; the plant upstream consensus sequence is shown in underlined text; and the start codon is shown in italics.

Primer 2 (B506) 34'MER,
TAGAAGCAGAAACTTACCATGTTGAAGGTGACAA (SEQ ID NO:10)

Here the IV2 intron is shown in bold text; the nagB sequence is shown in italics; and the is underlined portion denotes MET 70.

Primer 3 (B508) 34'MER
TTGTCACCTTCAACATGGTAAGTTTCTGCTTCTA (SEQ ID NO:11)

Here the IV2 intron is shown in bold text; the nagB sequence is shown in italics; and the underlined portion denotes MET 70.

Primer 4 (B509) 34'MER
AGACCGACATATTCGTCCTCCACATCAACAAATT (SEQ ID NO:12)

Here the IV2 intron is shown in bold text; the nagB sequence is shown in italics; and the underlined portion denotes TYR73 GLU72 ASP70.

Primer (B510) 34'MER
AATTTGTTGATGTGCAGGACGAATATGTCGGTCT (SEQ ID NO:13)

Here the IV2 intron is shown in bold text; the nagB sequence is shown in italics; and the underlined portion denotes ASP71 GLU72 TYR73.

Primer 6 (B511) 27'MER
CATGCCTCGAGCAGGGATAACAATTAC(SEQ ID NO:14)

Here the nagB 3' untranslated region is shown in italics; the stop codon is underlined; and the XhoI site is shown in bold.

All the above oligonucleotide primers were synthesised using "trityl-ON" and purified on "C.O.P" cartridges (see before).

The following three segments to be spliced were synthesised by PCR.

Segment 1

Produced by amplification of NT 1–234 of the coding region of nogB attaching a plant upstream region and a BglII site at the 5' end and overlap with NT 1–17 of the IV2 intron at the 3' end (Reaction 1).

Segment 2

Produced by amplification of the IV2 intron (189 BP) attaching an overlap with NT 218–234 of the coding region of nagB at the 5' end and another overlap with NT 235–251 of the nagB coding region at the 3' end (Reaction 2).

Segment 3

Produced by amplification of NT 235–801 of the coding region and stop codon of nagB, attaching an overlap with NT 172–189 of IV2 at the 5' end and an XhoI site at the 3' end (Reaction 3).

Reaction 1:
  73/69/65 µl water
  4/8/12 µl MgCl$_2$ 25 mM
  0.5 µl pPS48 nagB
  5 µl primer 1 (B507) 4 pmole/µl
  5 µl primer 2 (B506) 4 pmole/µl
  2 µl dNTP mix (2.5 mM each)
  0.5 µl Amplitaq Reaction 2:
  73/69/65 µl water
  4/8/12 µl MgCl$_1$ 25 mM
  0.5 µl pUC.GUS.intron
  5 µl primer 3 (B508)
  5 µl primer 4 (B509)
  2 µl dNTP mixture (2.5 mM of each)
  0.5 µl Amplitaq Reaction 3:
  73/69/65 µl water
  4/8/12 µl MgCl$_2$ 25 nM
  0.5 µl pPS48 nagB
  5 µl (B510) primer 5
  5 µl primer 6 (B511)
  2 µl dNTP mixture (2.5 nM of each)
  0.5 µl Amplitaq Temperature Programmes

| Cycle | Reactions 1 aud 3 | Reaction 2 |
|---|---|---|
| 1 | 94° C. - 5 mins | 94° C. - 5 mins |
| 2–29 | 94° C. - 1.5 mins | 94° C. - 1.5 mins |
|  | 58° C. - 1 min | 50° C. - 1 min |
|  | 72° C. - 2 mins | 72° C. - 2 mins |
| 30 | 94° C. - 1.5 mins | 94° C. - 1.5 mins |
|  | 58° C. - 1 min | 50° C. - 1 min |
|  | 72° C. - 10 mins | 72° C. - 10 mins |
| 31 | 4° C. - until collection | 4° C. - until collection |

The above reactions were run overnight.

Figure 13:
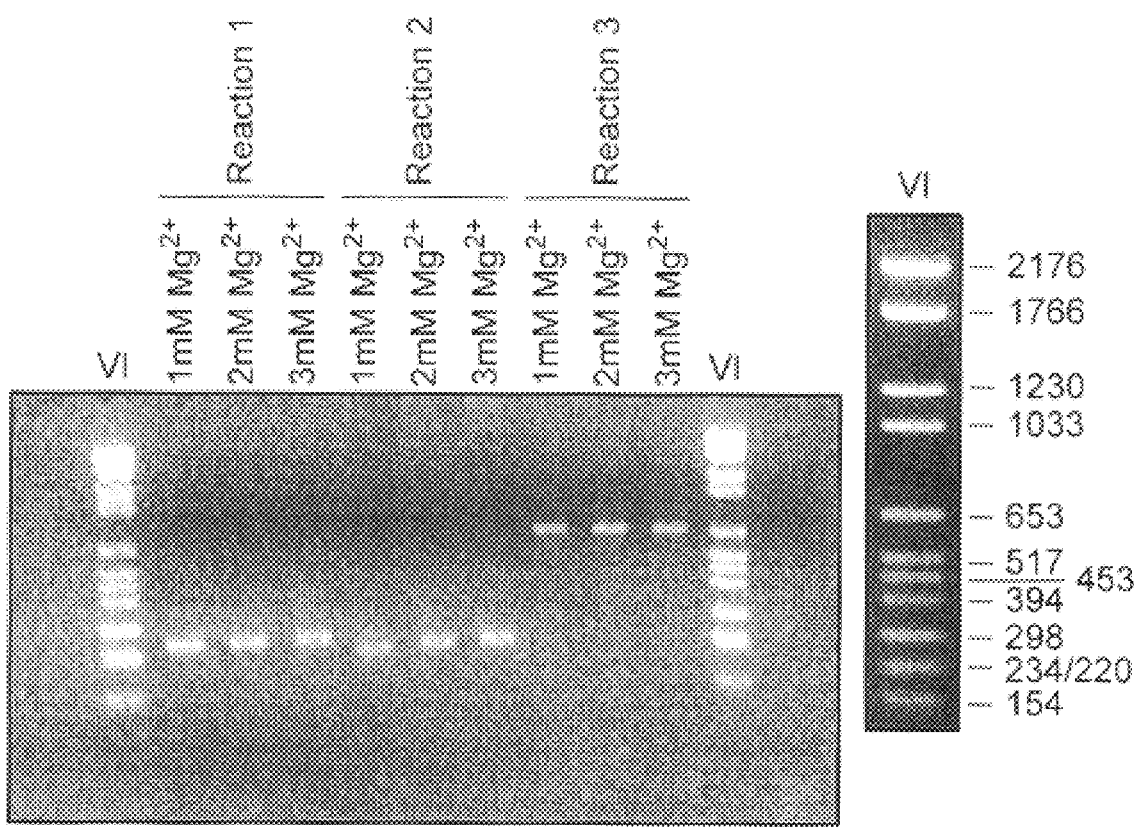
FIG. 13, which presents a photographic result of an electrophoresis study.
Figure 14:
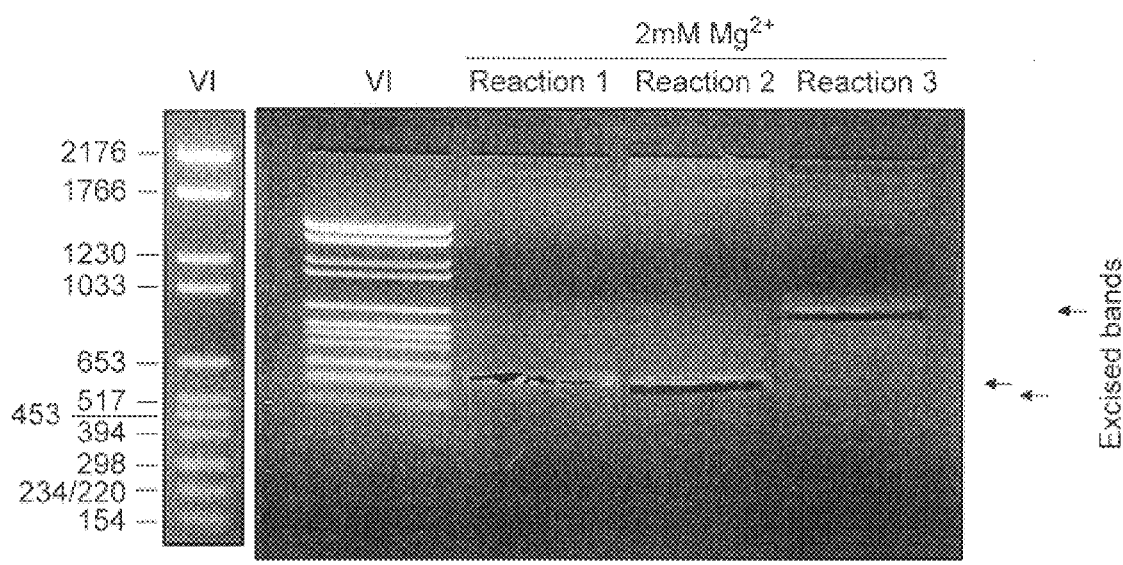
FIG. 14, which presents a photographic result of an electrophoresis study.

The PCRs were analysed by adding 2 µl of each reaction mixture to 8 µl water and 2 µl gel loading buffer (0.25% bromophenol blue/0.25% xylene cyanol FF/30% glycerol in water), and electrophoresis of the entire volume through a 2% w/v agarose gel in TAE buffer at 35V for approximately two hours. Samples were electrophoresed in parallel with Boehringer DNA MWT marker VI. The results are shown in FIG. 13. FIG. 14 shows a preparative gel of the same and also indicates the positions of the excised bands.

The migration of each product in the gel closely corresponded to the expected molecular size (reaction 1: 251 bp, reaction 2: 223 bp, reaction 3: 628 bp).

50 µl samples from each reaction performed at 2 mM MgCl$_2$ were added to 10 µl of gel loading buffer and resolved by electrophoresis in a 2% w/v agarose gel in TAE buffer at 35V for approximately two hours.

Bands were excised and the DNA extracted by placing the gel section in an Eppendorf tube, freezing in liquid N$_2$, thawing for five minutes at 37° C., and then centrifugation of the buffer out of the gel in a Millipore Ultrafree MC filtration tube at 13000 g for five minutes. The DNA in the filtrate was then precipitated with 1/10 volume acetate and 2 volumes of ice cold ethanol (96%) followed by centrifugation at 13000 g for five minutes. The sedimented DNA was washed with iceold 70% v/v ethanol, dried and resuspended in 10 µl of TE.

In order to check that the bands observed after PCR were not artifacts, a set of single primer control reactions were run.

The single primer control reactions were compared with primer pair reactions by taking 2 µl samples of each, adding them to 8 µl water and 2 µl buffer and electrophoresis of the entire volume through a 2% w/v agarose gel in TAE buffer at 35V for approximately two hours.

Figure 15:
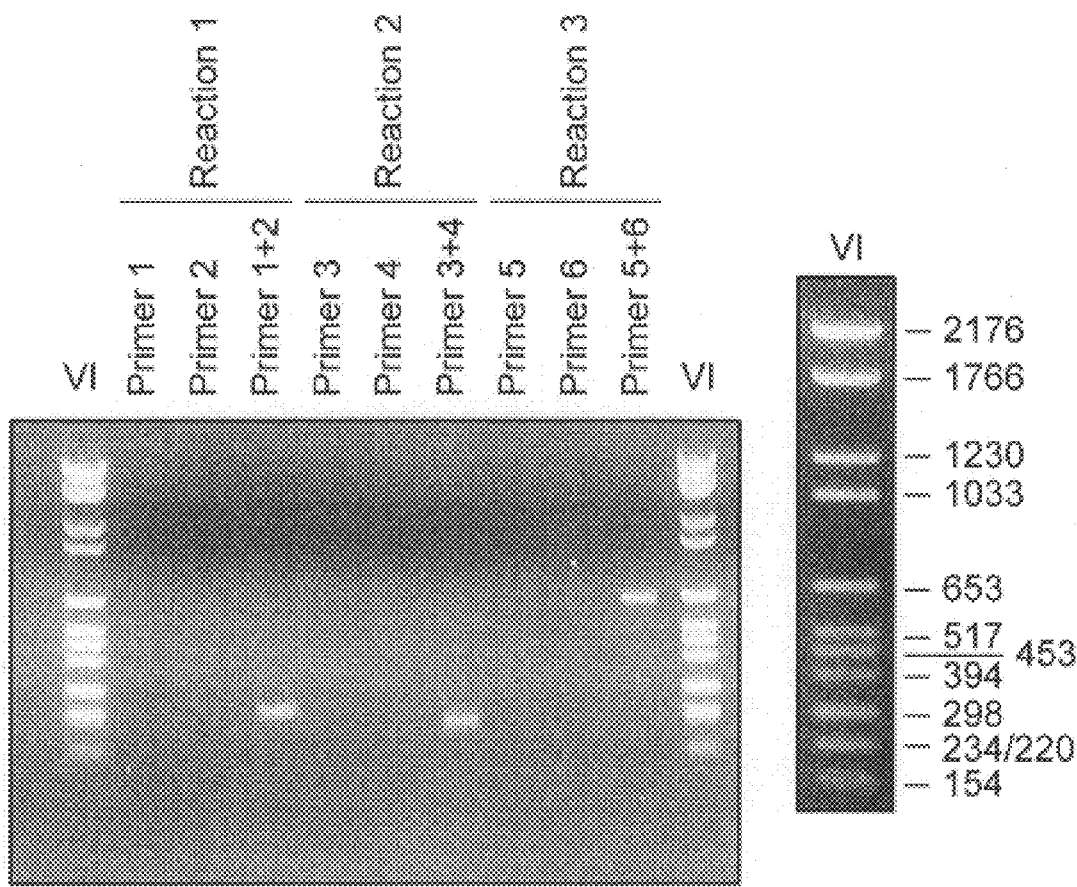
FIG. 15, which presents a photographic result of an electrophoresis study.

The results of this study are shown in FIG. 15.

As shown in FIG. 15, no artifactual bands appeared in the single primer controls.

The splicing of sections 1 and 2 together was accomplished using the following PCR reaction mixture:

51 µl water
8 µl MgCl$_2$ 25 mM
10 µl Amplitaq 10×buffer without Mg
1 µl section 1
8 µl section 2
5 µl primer 1 (B507) 4 pmoles/µl
5 µl primer 4 (B509) 4 pmoles/µl
2 µl dNTP mixture (2.5 mM each)
0.5 µl Amplitaq buffer (Perkin Elmer)

The splicing reaction was run overnight using the following temperature programme.

| Cycle | Splicing reaction (Sections 1 & 2) |
|---|---|
| 1 | 94° C. - 5 mins |
| 2–29 | 94° C. - 15 mins |
|  | 54° C. - 1 min |
|  | 72° C. - 2 mins |
| 30 | 94° C. - 1.5 mins |
|  | 54° C. - 1 min |
|  | 72° C. - 10 mins |
| 31 | 4° C. - until collection |

In order to furnish more product for future use, reaction 2 was repeated and run in parallel.

Figure 16:
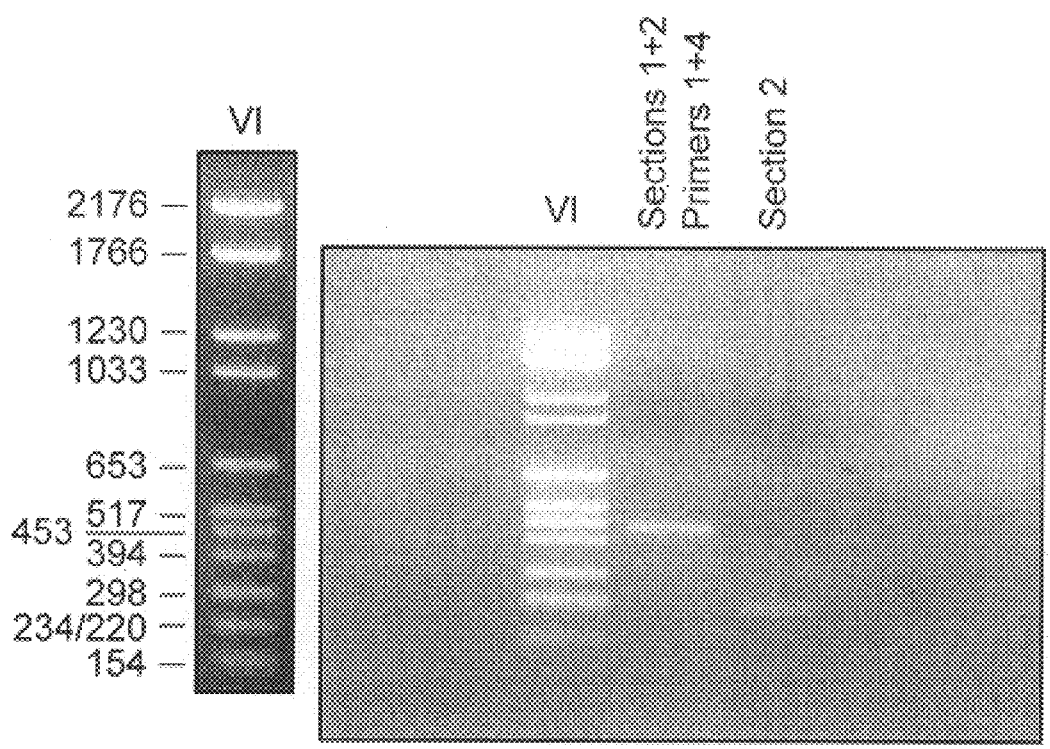
FIG. 16, which presents a photographic result of an electrophoresis study.

6 µl samples of each of the PCR reactions were added to 24 µl water and 6 µl of gel loading buffer (Amplitaq buffer—supplied by Perkin Elmer). The entire volume of each mixture was loaded on to a 2% w/v agarose gel in TAE buffer and electrophoresed at 35V for approximately two hours. The results are shown in FIG. 16.

Figure 17:
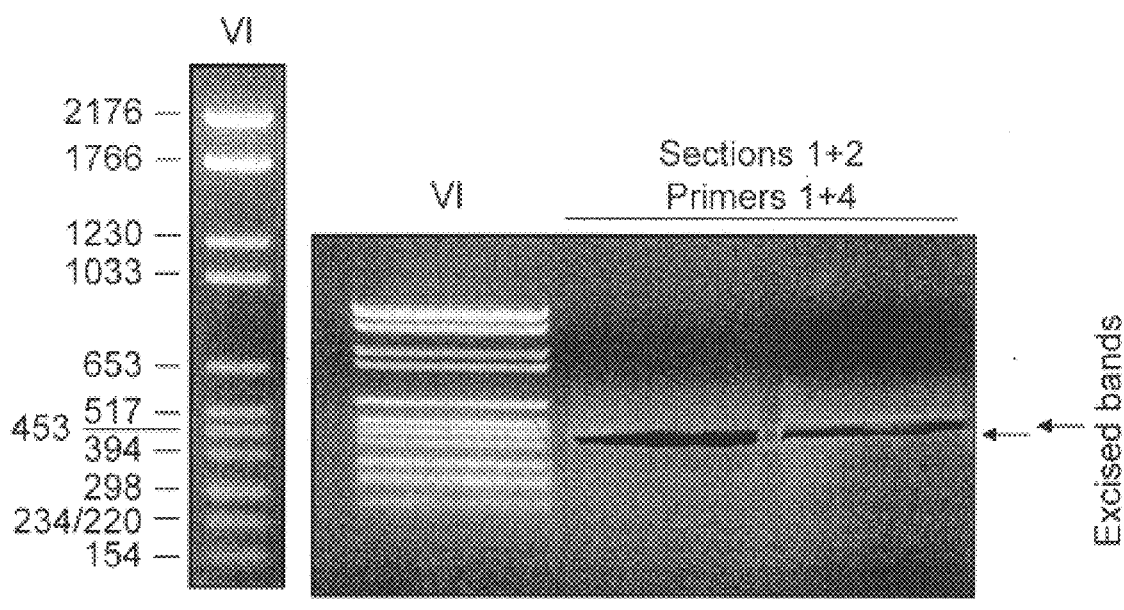
FIG. 17, which presents a photographic result of an electrophoresis study.

The mobility of the spliced product corresponded very closely with the expected size of 440 bp. 2×50 µl samples of the spliced product of sections 1 and 2 were electrophoresed and the DNA extracted from the product bands in the same manner as described above. The results are shown in FIG. 17.

The splicing of the fused sections 1 and 2 with section 3 was accomplished using the following PCR reaction mixture:

67 µl water
10 µl Amplitaq 10×buffer without Mg
8 µl MgCl$_2$ 25 mM
1 µl fused sections 1 and 2
2 µl section 3
5 µl primer 1 (B507) 4 pmoles/µl
5 µl primer 6 (B511) 4 pmoles/µl
2 µl dNTP mixture (2.5 mM of each)
0.5 µl Amplitaq buffer The splicing reaction was run overnight using the following temperature programmes

| Cycle | Lower annealing temp | higher annealing temp |
|---|---|---|
| 1 | 94° C. - 5 mins | 94° C. - 5 mins |
| 2–29 | 94° C. - 1.5 mins | 94° C. - 1.5 mins |
|  | 56° C. - 1 min | 60° C. - 1 min |
|  | 72° C. - 2 mins | 72° C. - 2 mins |
| 30 | 94° C. - 1.5 mins | 94° C. - 1.5 mins |
|  | 56° C. - 1 min | 60° C. - 1 min |
|  | 72° C. - 10 mins | 72° C. - 10 mins |
| 31 | 4° C. - until collection | 4° C. - until collection |

Single primer controls containing either primer 1 alone or primer 6 alone were also run at the lower annealing temperature.

Figure 18:
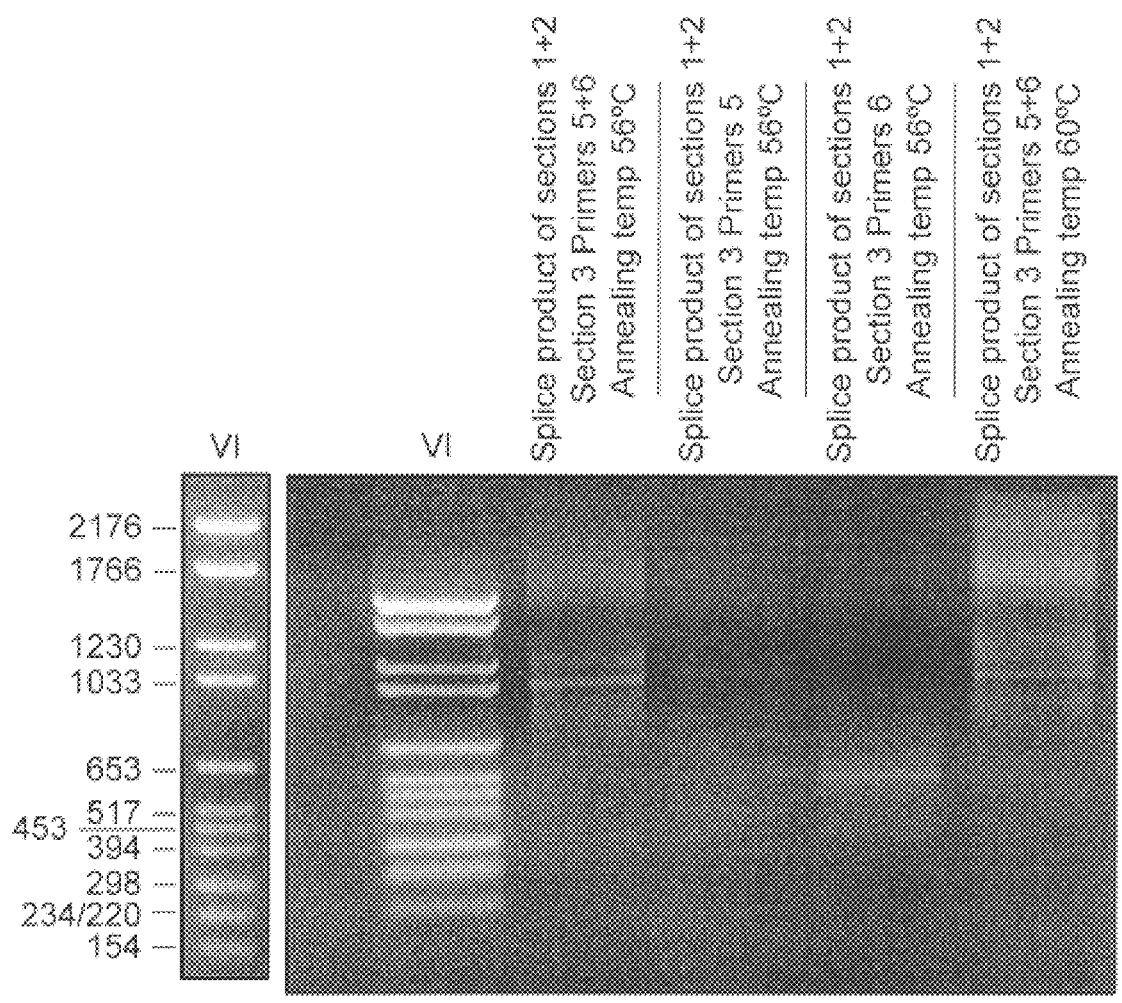
FIG. 18, which presents a photographic result of an electrophoresis study.

The PCR reactions were analysed by electrophoresis in an identical manner to that described above. The results are shown in FIG. 18.

The splicing reaction produced a prominent band on the gel which corresponds reasonably well with the expected molecular size of 1034 bp. The primer 6 single primer control also produced a product but slightly larger than this and the primer 5 single primer control produced a much smaller product. Interestingly, the higher annealing temperature of 60° C. did not decrease the background but, on the contrary, increased it.

The spliced product of the fused sections 1 and 2 and section 3 was separated by electrophoresis in an identical manner to that described above for the purification of segments 1, 2 and 3. The band was excised from the gel and purified using gene clean II.

Figure 19:
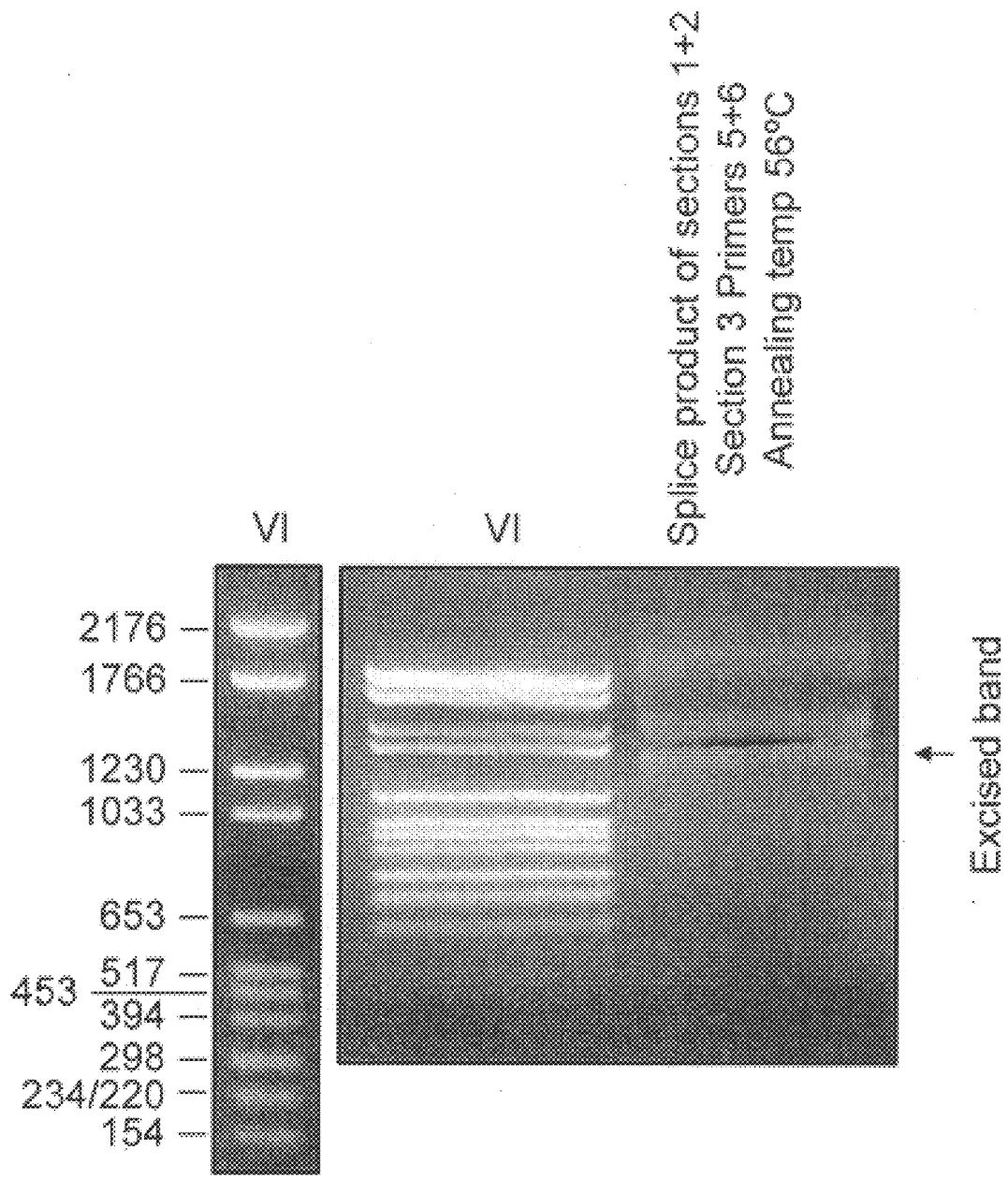
FIG. 19, which presents a photographic result of an electrophoresis study.

A further electrophoresis run was performed and the results are shown in FIG. 19.

Cloning and Sequencing

The PCR products from amplification of nagB, and nagB into which the IV2 intron had been spliced, were cloned into the EcorRV site of pT7Blue (Novagen) to which T-overhangs had been attached. Blue/white selection of recombinants was performed on LB plates containing 50 µg/ml ampicillin, on to which 50 µl X-gal (20 mg/ml dimethyl sulphoxide) had been spread and allowed to dry on a sterile laminar flow bench. Minipreps of white colonies were checked by double digests with EcoRV/Xba I, and PstI digestion. Large scale preparations of the recombinant plasmids were then made using Quiagen (Quiagen), and this DNA was used for sequencing.

Thermal Sequencing

Thermal sequencing was performed using the following primers (Pharmacia).

5'fluorescein-d[CAG CGT TGT AAA ACG ACG GCC AGT]-3' (SEQ ID NO:15)
5'fluorescein-d[CAG GAA ACA GCT ATG AC]-3' (SEQ ID NO:16)

Reagents used were from an Autoread 1000 sequencing kit (Pharmacia) with the exception of the thermostable polymerase, thermo sequenase (Amersham Life Science).

0.5–1 µg of plasmid DNA was taken up in 21 µl of water. Reaction mixtures were set up as follows:

| Fluorescent marker (1–2 pmol) | 1 µl |
|---|---|
| Plasmid DNA | 5 µl |
| A, C, G or T reagents | 2 µl |

The samples were heated to 95° C. and then immediately subjected to 25 cycles of the following temperature programme:

| | |
|---|---|
| 95° C. | 30 s |
| 60° C. | 30 s |

Sequencing Using the Autoread 1000 Sequencing Kit (Pharmacia)

The following primers, which complement the nucleotide sequence of nagB, were synthesised for sequencing using the Autoread 1000 sequencing kit (Pharmacia).

```
206-222        GCTTTAAGCACGTTGTC (SEQ ID NO:17)
225-209 (rev)  GGTGACAACGTGCTTAA (SEQ ID NO:18)
719-703 (rev)  TTTGCGACGCGAGTGTC (SEQ ID NO:19)
431-415 (rev)  TATTCGTCCTGCACATC (SEQ ID NO:20)
```

The concentrations of the plasmid templates were adjusted to approximately 20 μg/μl. Primer annealing was performed in the following reaction mixture.

| | |
|---|---|
| Template DNA | 10 μl |
| Primer (1–2 pmol) | 2 μl |
| Annealing buffer | 2 μl |
| Sterile water | 1 μl |

The annealing mixtures were vortexed, briefly centrifuged, and incubated at 65° C. for 10 minutes. The reactions were allowed to cool to room temperature over a period of 45 minutes, and then briefly centrifuged.

Each annealing temperature was mixed with 2 μl of Fluore-dATP labelling reagent. 2 μl of diluted T7 DNA polymerase (4 U/μl) were added to each, and the reaction was incubated at 37° C. for ten minutes. Following this primer labelling reaction, the mixture were maintained at 37° C. while 1 μl of extension buffer, and 3.5 μl dimethyl sulphoxide were added. 5.4 μl of each primer labelling reaction mixture were immediately added to 3 μl of each nucleotide mix (A, C, G, and T) and incubated at 37° C. for a further five minutes. Reactions were terminated by the addition of 5 μl of Stop Solution.

Electrophoresis

Electrophoresis of both types of sequencing reaction was carried out using a Pharmacia ALF automated sequencer. Samples were heated to 90° C. for two minutes before loading 8 μl aliquots onto the sequencing gel.

Figure 1:
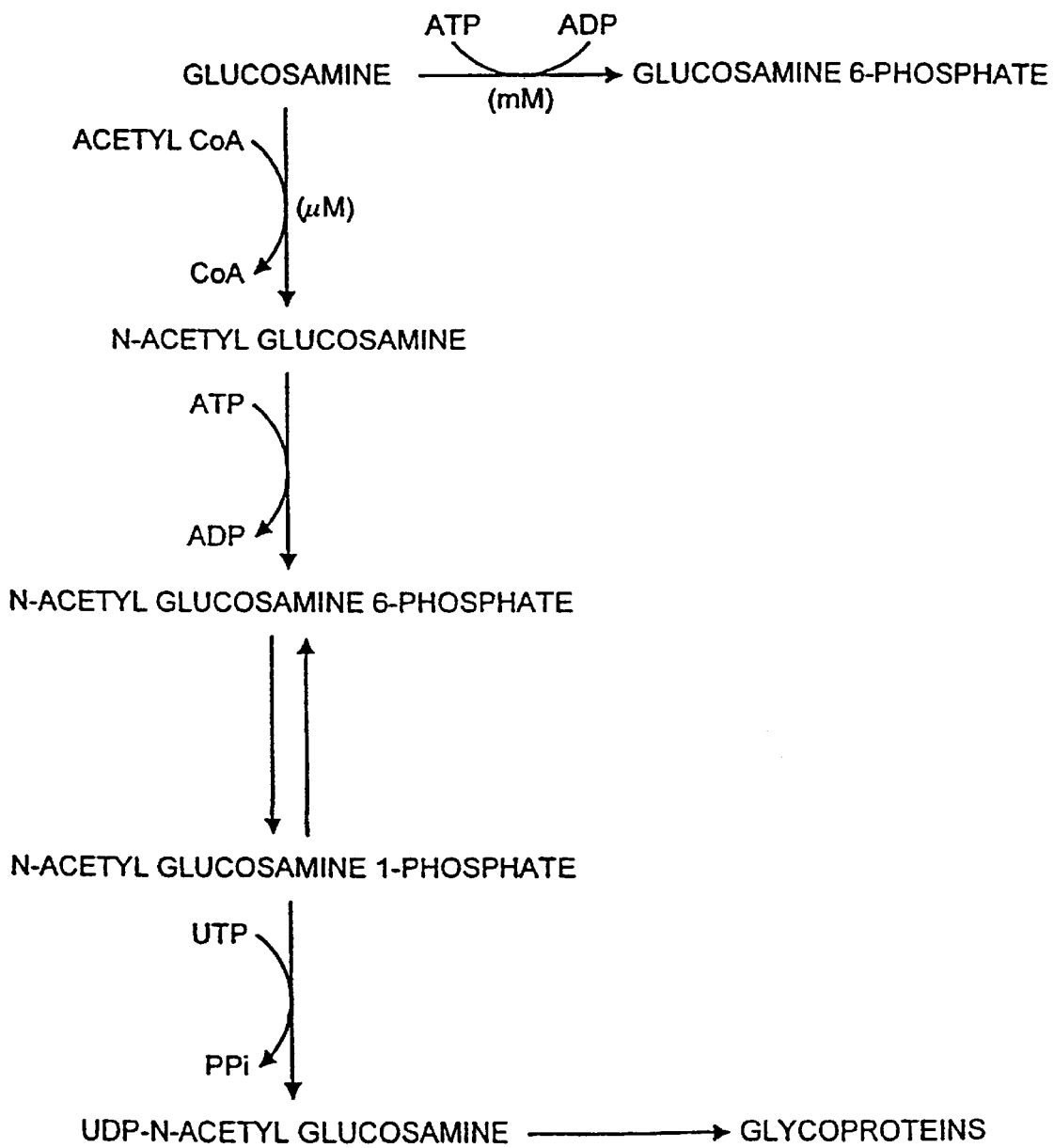
FIG. 1, which is a schematic diagram of a metabolic pathway.
Figure 2:
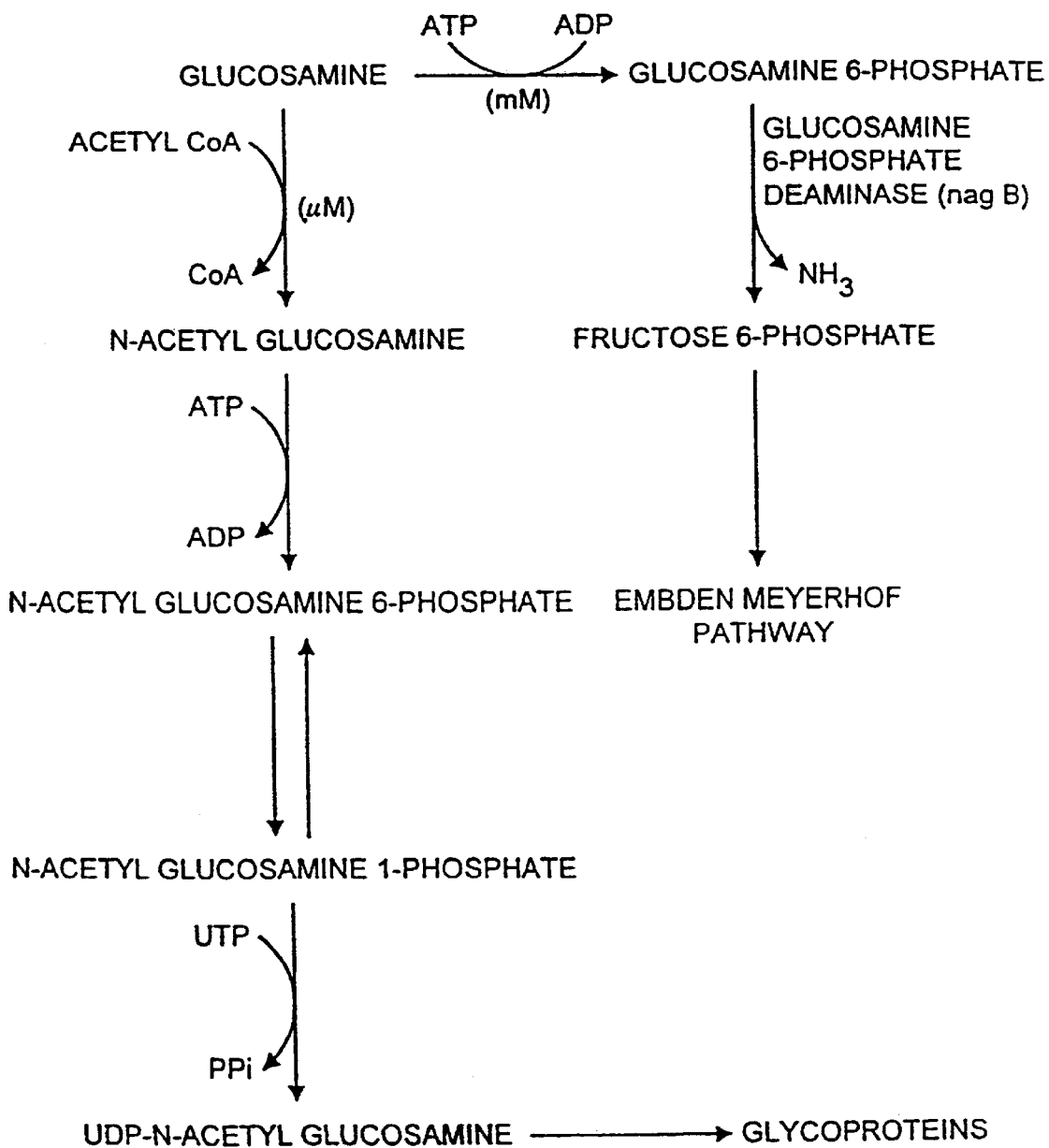
FIG. 2, which is a schematic diagram of a metabolic pathway.
Figure 3:
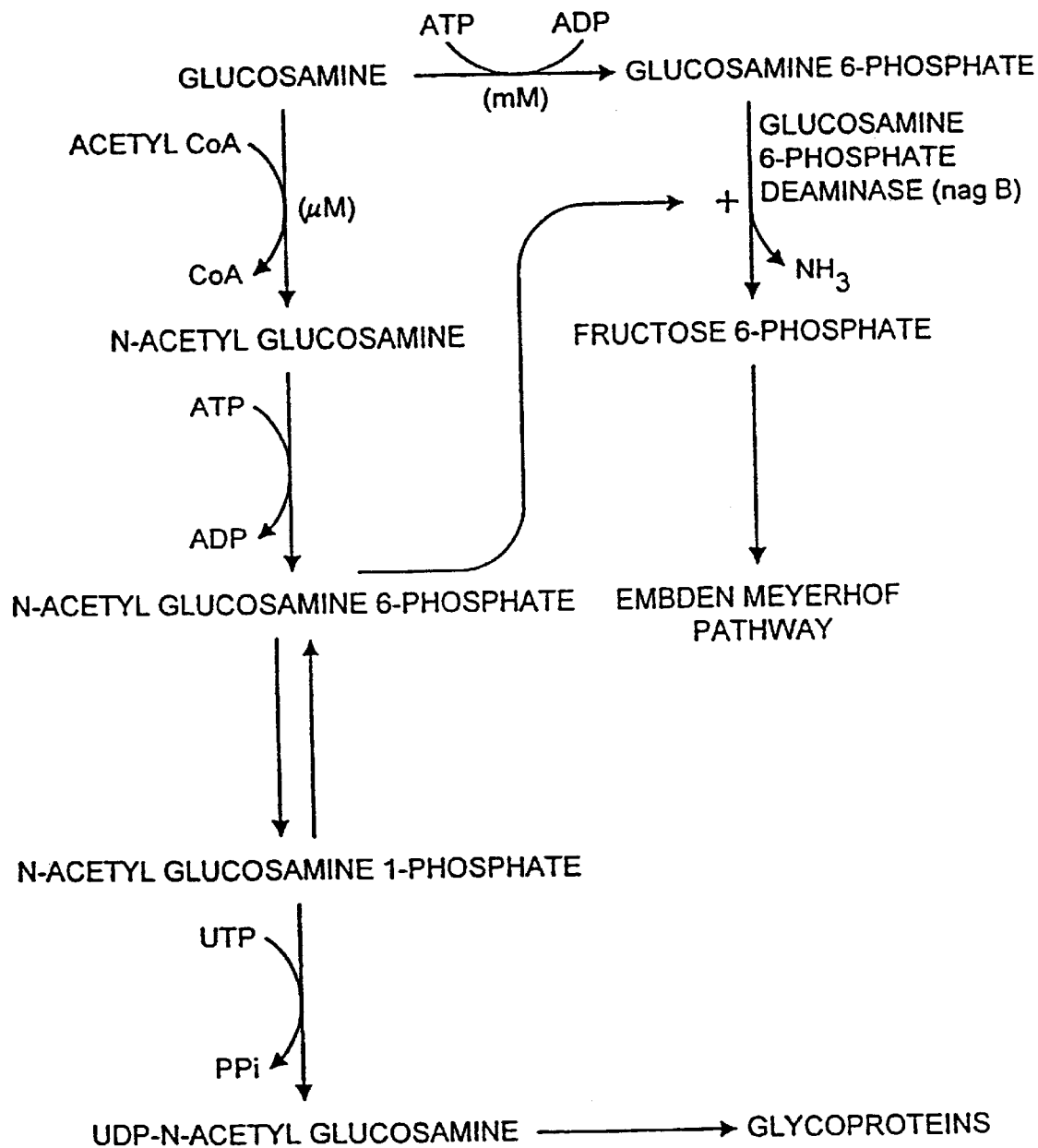
FIG. 3, which is a schematic diagram of a metabolic pathway.
Figure 6:
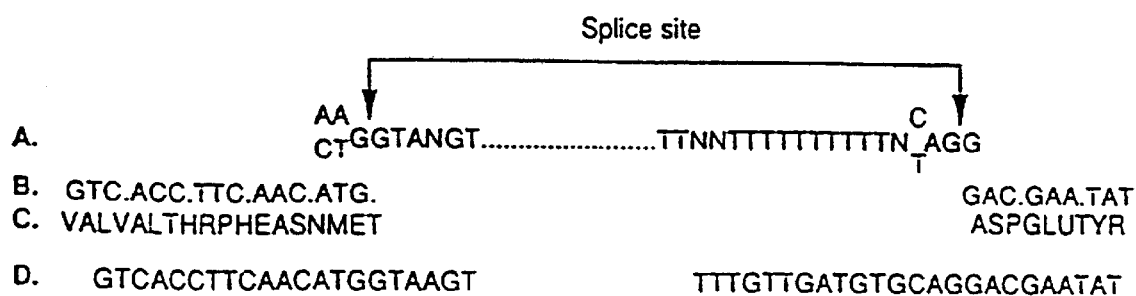
FIGS. 6A–6D, which present some nucleotide sequences.
Figure 8:
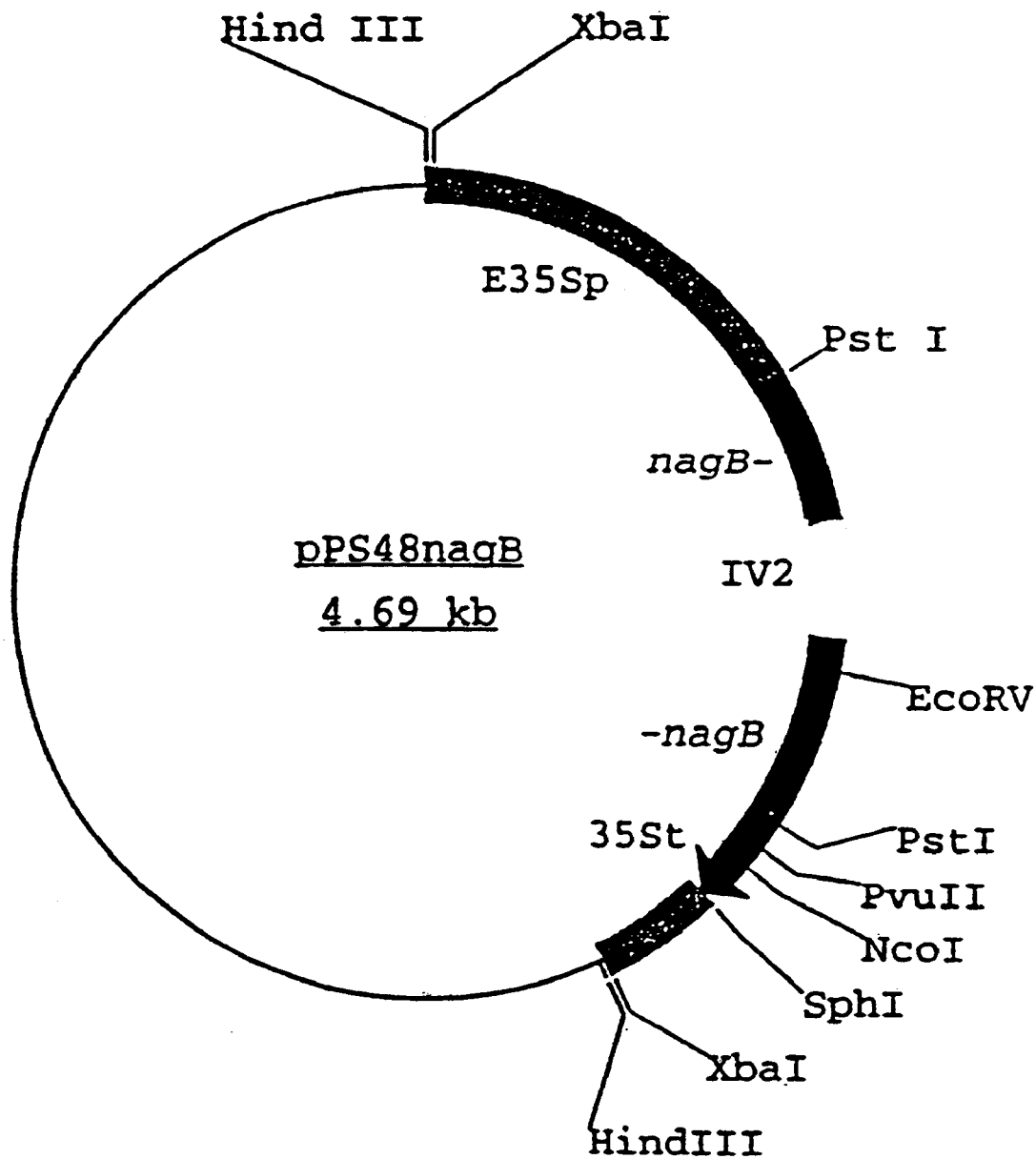
FIG. 8, which presents a schematic diagram of a plasmid.
Figure 9:
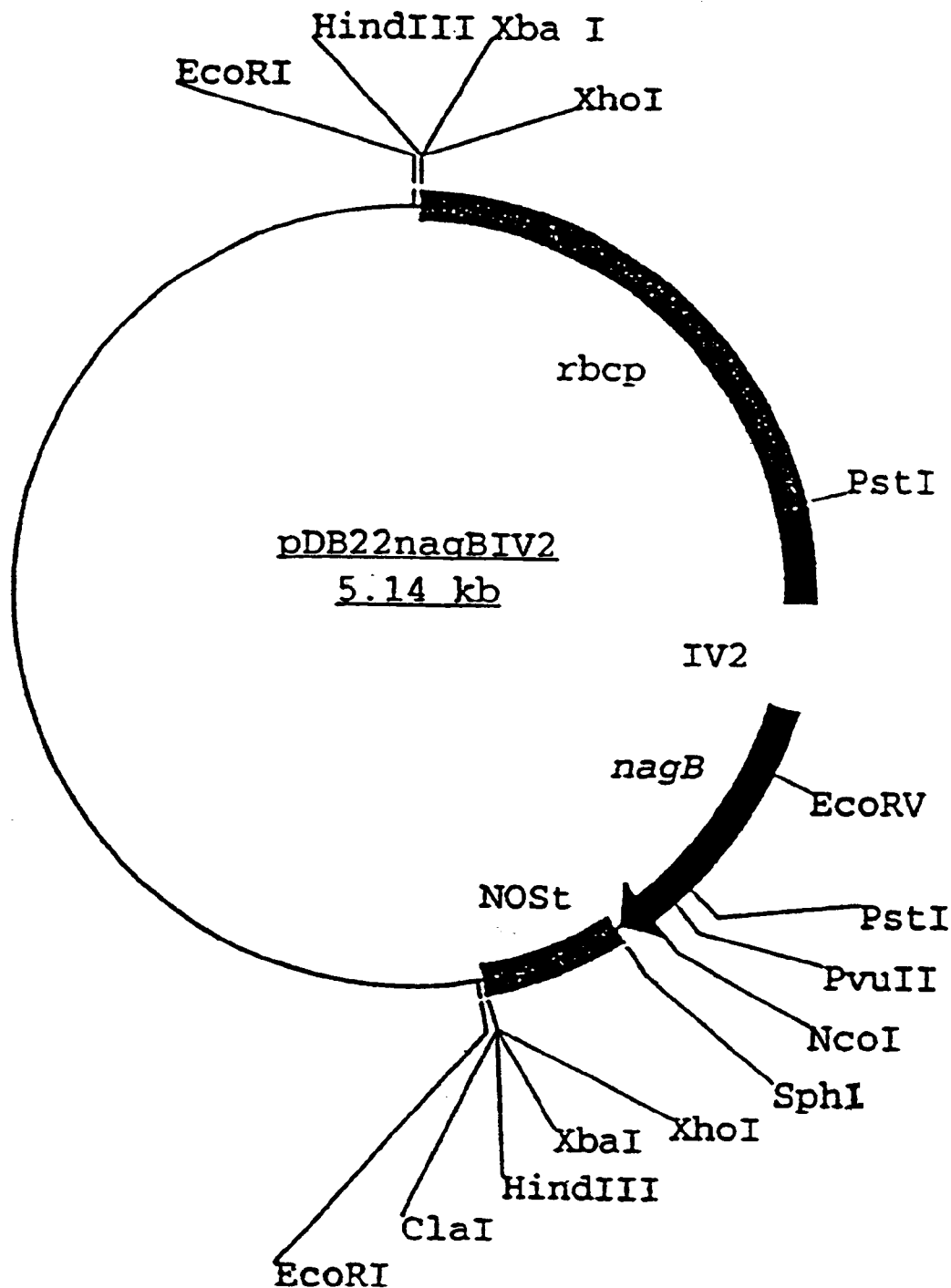
FIG. 9, which presents a schematic diagram of a plasmid.

Ligation of nagB Constructions into Plant Expression Cassettes, and Cloning into a Plant Transformation Vector Clones of the nagB, and nagB containing the IV2 intron, in pT7Blue, were confirmed by sequencing to have the correct nucleic acid sequence. These were excised from pT7Blue as BglII/XhoI fragments and directionally cloned into the CamV 35S expression cassette of BamHI/SalI cut pPS48 (see FIG. 8). The nagB construction, into which the IV2 intron had been spliced, was also cloned, in the same manner, between the rubisco small subunit promoter and the nopaline synthase terminator of pDB22 (see FIG. 9). The nagB constructions, ligated into expression cassettes in this manner, were excised from pPS48 and pDB22, with adjacent promoters and terminators, as HindIII fragments, and ligated into the unique HindIII site of pVictor IV GNG.

Figure 10:
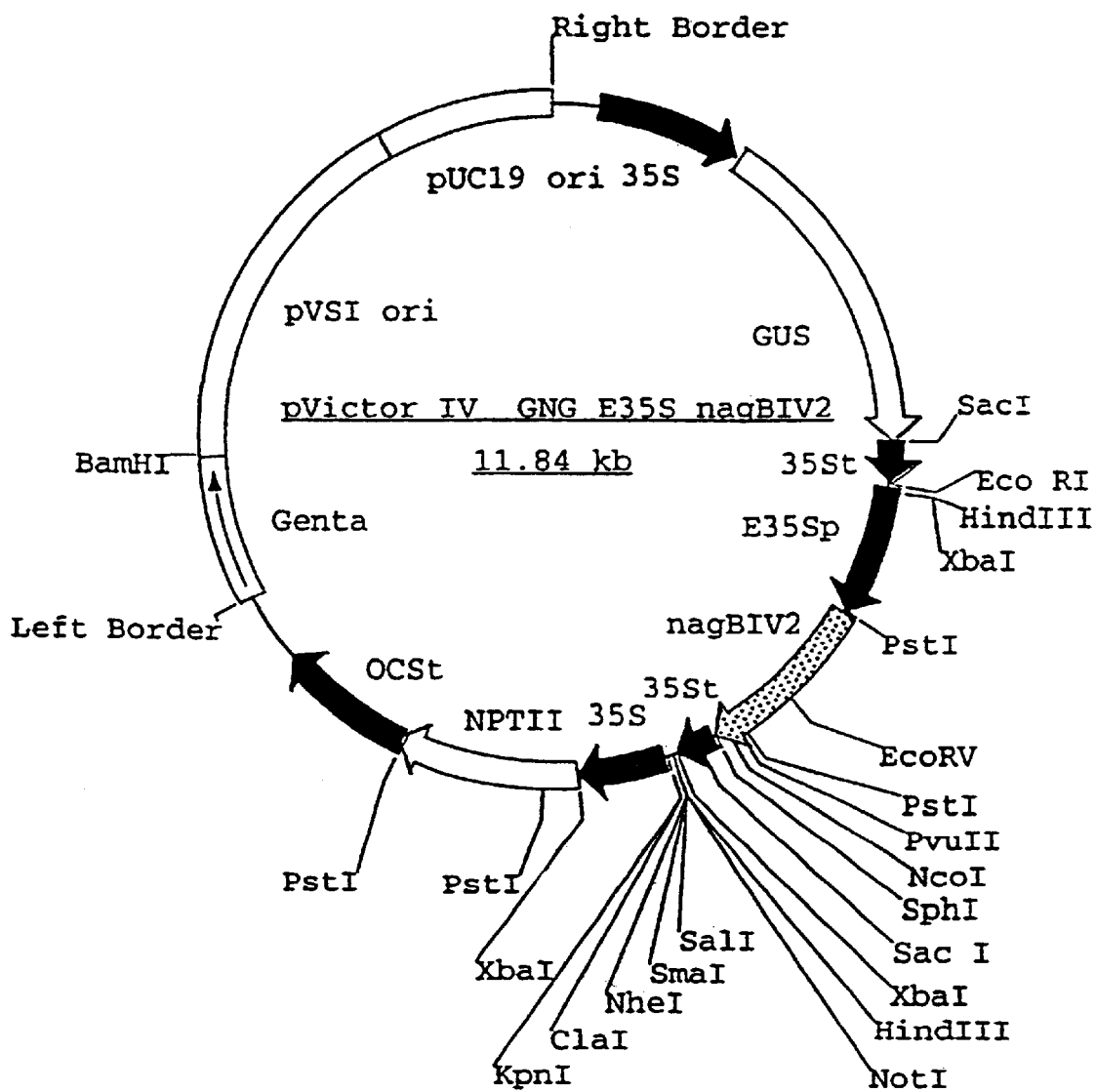
FIG. 10, which presents a schematic diagram of a plasmid.

The plasmid containing the nagB coding region, into which the IV2 intron had been spliced, and which is ligated into a CaMV 35S expression cassette, was named termed pvictor IV GNG E35S nagB IV2 (see FIG. 10).

Figure 11:
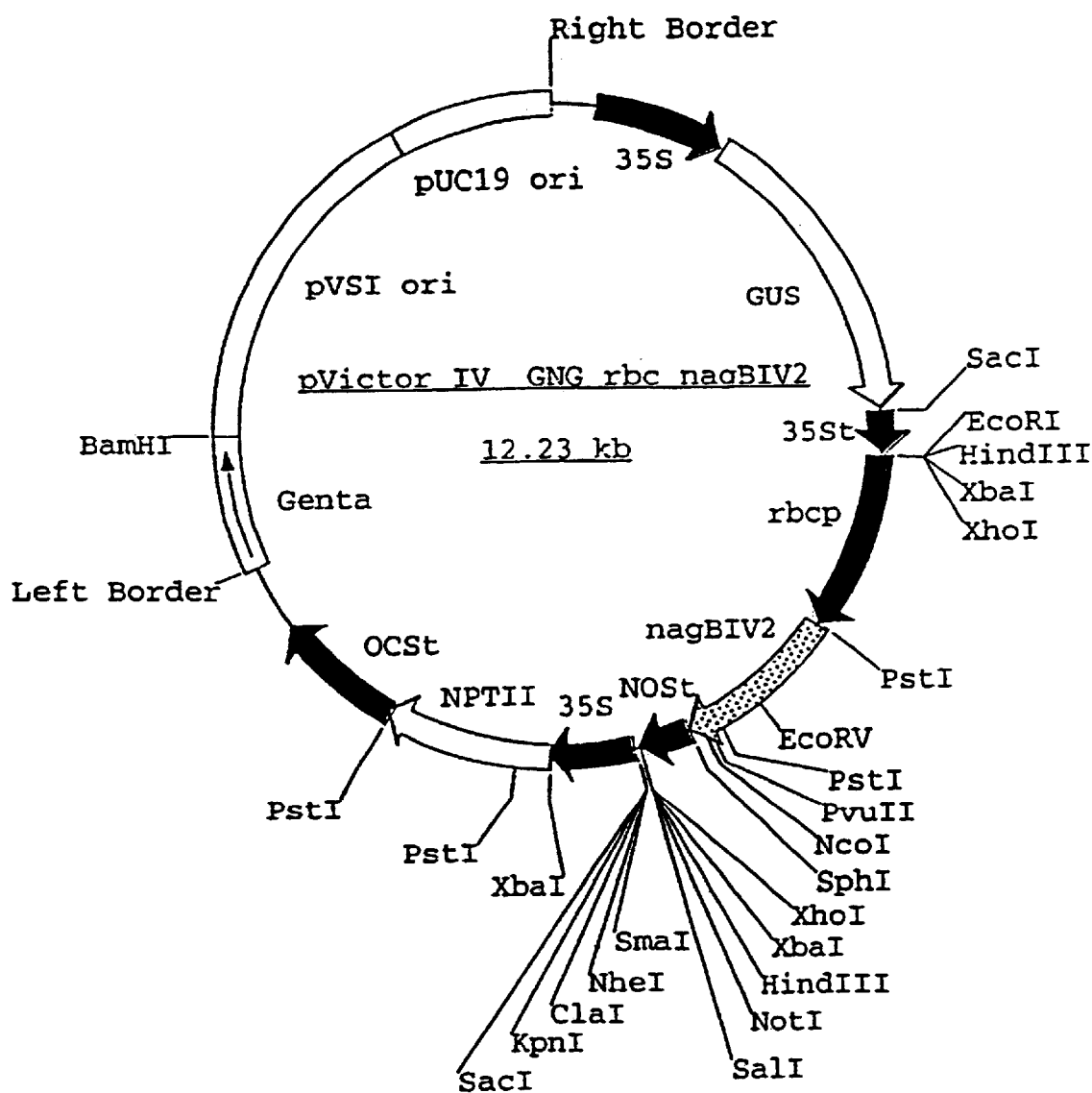
FIG. 11, which presents a schematic diagram of a plasmid.

The plasmid containing the nagB coding region, into which the IV2 intron had been spliced, and which is ligated into a rubisco small subunit promoter/nopaline synthase expression cassette, was termed pVictor IV GNG rbc nagB IV2 (see FIG. 11).

The plasmid formed, which contains the unmodified nagB coding region within a CaMV 35S expression cassette, was termed pVictor IV GNG E35S nagB (see FIG. 12).

Toxicity Studies

Dose-response Curve

Figure 20:
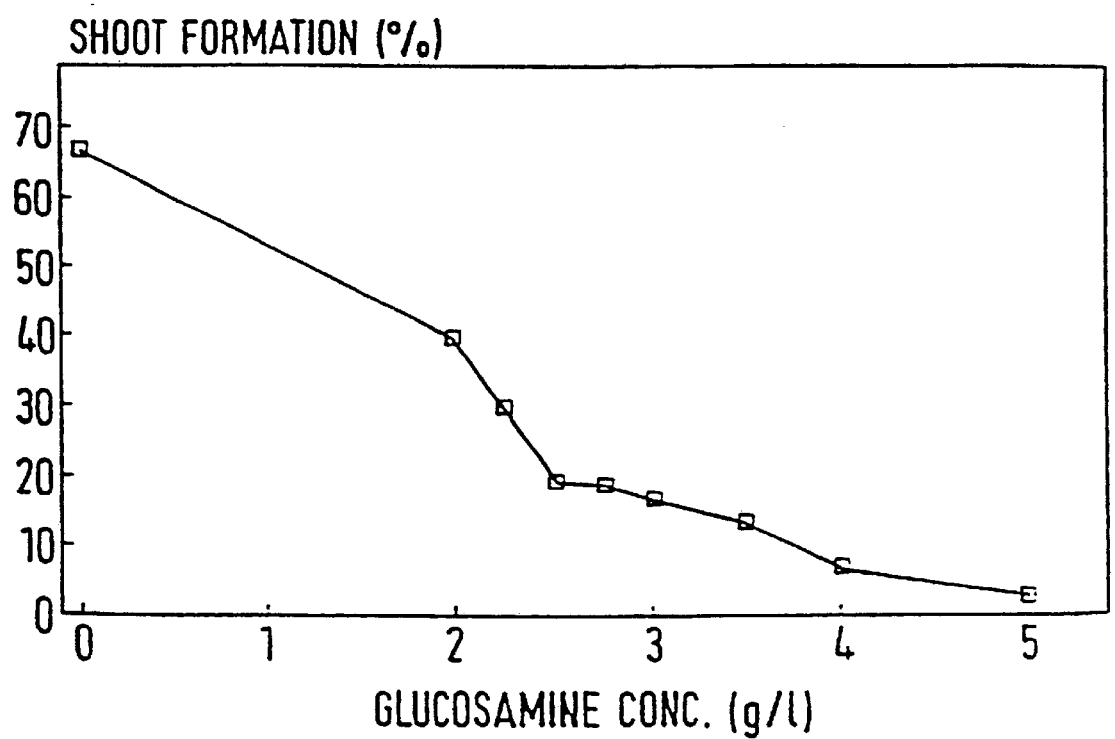
FIG. 20, which presents a graph.

In order to establish the toxicity of glucosamine to guar explants, a dose-response curve with glucosamine concentrations ranging from 0 to 5.0 g/l was made using non-transgenic guar cotyledons as explants. The effect on shoot formation on the explants was used to determine the toxicity of glucosamine (FIG. 20).

The guar explants were obtained as follows. Guar seeds were sterilized in a 2.5% sodium hypochlorite solution at pH 7.0 added two drops of Tween 80 pr 100 ml solution. The seeds were stirred for 25 minutes in this solution and then washed five times with sterile water. Seeds were sown on germination medium (4.43 g/l MSMO (Sigma M6899), 20 g/l sucrose, 8.0 g/l agar, pH adjusted to 5.8 with KOH) and placed at 25° C. for 11–13 days at a 12 h/12 h day/night regime.

The cotyledons including about 2 mm of hypocotyl were excised from the seedlings and were used as explants for this experiment as well as for transformation experiments. The cotyledons were placed on selection medium containing various concentrations of glucosamine.

Selection medium:

3.2 g/l Gamborg B5 (Sigma G5893)

20 g/l sucrose 1.0 mg/l benzylaminopurine 0.05 mg/A gibberellic acid (GA3)

1.0 μM silver thiosulphate 1.0 mg/l $NiCl_2$, 6 $H_2O$ 0.5 mg/l 2-(p-chlorophenoxy)-2-methylpropionic acid 30 mg/l cefotaxime 30 mg/l sulbactam (Betamaze)

0–5 g/l D-glucosamine, HCl (according to the experiment)

pH 5.7

After three weeks, the percentage of explants forming shoots on the various glucosamine containing media were determined and the results are given in FIG. 20.

Factors Affecting the Toxicity of Glucosamine

Figure 21:
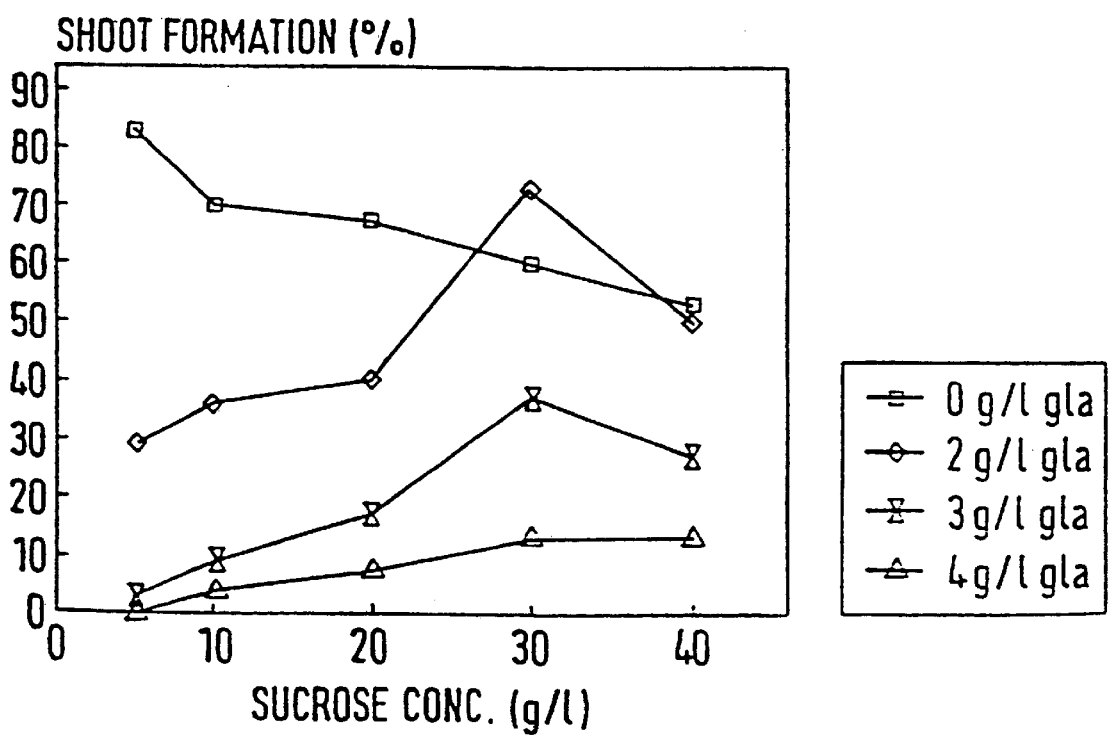
FIG. 21, which presents a graph.

In order to be able to find appropriate selection conditions, some factors affecting the toxicity of glucosamine were studied. Initially, sucrose was tested at various concentrations (5–40 g/l) in the selection medium. The results, which are shown in FIG. 21, show that higher concentrations of sucrose reduce the toxic effect of glucosamine for the plant cells being investigated. It is expected that other saccharides such glucose, fructose, maltose, mannose etc may also affect the effect of glucosamine.

Next, the effect of the concentration of the Gamborg B5 salts in the selection medium was tested in the presence of glucosamine (3.0 g/l). We investigated the use of these salts with a view to decreasing the carbon content of the medium.

The results are as follows:

| Gamborg B5 salts in selection medium (g/l) | Shoot formation on guar explants (%) |
|---|---|
| 3.2 | 17.4 |
| 2.4 | 9.1 |
| 1.6 | 6.2 |

It is to be noted that a 50% reduction of the Gamborg B5 salts in the selection medium had no significant effect on shoot formation in the absence of glucosamine.

Hence, it is possible to vary selection medium to affect the effect of glucosamine and hence, the outcome of transformation experiments using glucosamine selection.

Transformation Studies

The following example demonstrates that the E coli nagB gene can be used as a means to provide selection of transformed cells, such as transgenic guar (Cyamopsis tetragonoloba) shoots, on or in media containing glucosamine as selective agent.

Transgenic Gaur Plants

Transformation of guar cotyledonary explants was performed according to Joersbo and Okkels (PCT/DK95/00221) using Agrobacterium tumefaciens LBA4404 harbouring the plasmid shown in FIG. 10.

Selection of transgenic shoots was accomplished using the above-mentioned selection medium with various concentrations of glucosamine, sucrose and Garnborg B5 salts. After four weeks the shoots were harvested and all explants were transferred to fresh selection medium (same composition) and after another four weeks of selection the last shoots were harvested.

After harvest, the shoots were analysed for β-glucuronidase (GUS) activity using the histochemical assay (Jefferson et al, 1987, EMBO J 6: 3901–3907). The number of GUS-positive shoots are given in the table below.

| Sucrose (g/l) | Glucosamine (g/l) | B5-salts (g/l) | No of GUS-positive shoots |
|---|---|---|---|
| 10 | 2.5 | 3.2 | 2 |
| 20 | 2.5 | 2.4 | 1 |
| 20 | 3.0 | 2.4 | 1 |

Thus, transgenic shoots were obtained on selection media with different contents of glucosamine, sucrose and Gamborg B5 salts indicating that the selection medium can be varied significantly and remain useful for the selection of transgenic shoots.

Transgenic Potato Plants

General teachings on potato transformation may be found in our copending patent applications PCT/EP96/03053, PCT/EP96/03052 and PCT/EP94/01082 (the contents of each of which are incorporated herein by reference).

For the present studies, the following protocol was adopted.

Plasmid Construction

The disarmed Agrobacterium tumefaciens strain LBA 4404, containing the helper vir plasmid pRAL4404 (Hoekema et al, 1983 Nature 303 pp 179–180), was cultured on YMB agar ($K_2HPO_4.3H_2O$ 660 mg $l^{-1}$, $MgSO_4$ 200 mg $l^{-1}$, NaCl 100 mg $l^{-1}$, mannitol 10 g $l^{-1}$, yeast extract 400 mg $l^{-1}$, 0.8% w/v agar, pH 7.0) containing 100 mg $l^{-1}$ rifampicin and 500 mg $l^{-1}$ streptomycin sulphate. Transformation with pVICTOR IV GNG E35S nagB IV2 or pVICTOR IV GNG rbc nagB IV2 or pVICTOR IV GNG E35 S nagB was accomplished using the freeze-thaw method of Holters et al (1978 Mol Gen Genet 163 181–187) and transformants were selected on YMB agar containing 100 mg $l^{-1}$ rifampicin and 500 mg $l^{-1}$ streptomycin, and 50 mg $l^{-1}$ gentamycin sulphate. Transformation with a control construct lacking the nagB gene was performed in the same manner.

Transformation of Plants

Shoot cultures of Solanum tuberosum cv Saturna were maintained on LS agar containing Murashige Skoog basal salts (Sigma M6899) (Murashige and Skoog, 1965, Physiol Plant 15 473–497) with 2 $\mu$M silver thiosulphate, and nutrients and vitamins as described by Linsmaier and Skoog (1965 Physiol Plant 18 100–127). Cultures were maintained at 25° C. with a 16 h daily photoperiod. After approximately 40 days, subculturing was performed during and the shoots cut into mononodal segments of approximately 8 mm length.

Shoot cultures of approximately 40 days maturity (5–6 cm height) were cut into 8 mm internodal segments and/or leaves were cut off and wounded by making 24 small cuts over the midrib of the leaf. These were then placed into liquid LS-medium containing Agrobacterium tumefaciens transformed with pVICTOR IV GNG E35 S nagB IV2 or pVICTOR IV GNG rbc nagB IV2 or pVICTOR IV GNG E35S nagB ($A_{660}$=0.5, pathlength 1 cm). Following incubation at room temperature for 30 minutes, the segments were dried by blotting on to sterile filter paper and transferred to LS agar (0.8% w/v containing 2 mg $l^{-1}$ 2,4-D and 500 $\mu$g $l^{-1}$ trans-zeatin. The explants were covered with filter paper, moistened with LS medium, and covered with a cloth for three days at 25° C. Following this treatment, the segments can be washed with liquid LS medium containing 800 mg $l^{-1}$ carbenicillin, and then transferred on to LS agar (0.8% w/v) containing 1 mg $l^{-1}$ trans-zeatin, 100 mg $l^{-1}$ gibberellic acid (GA3), with sucrose (eg 7.5 g $l^{-1}$). This agar can optionally contain glucosamine (eg 2.5 g $l^{-1}$). The segments were sub-cultured to fresh substrate each 34 weeks. In 3 to 4 weeks, shoots develop from the segments and the formation of new shoots continued for 3–4 months.

The regenerated shoots are maintained on substrate composed of LS-substrate, 0.002 mM STS (Silthiosulfat) and agar (8 g/l). Carbenicillin (800 mg/l) can be added if desired.

The transgenic plants may be verified by performing a GUS assay on the cointroduced β-glucuronidase gene according to Hodal, L. et al. (Pl. Sci. (1992), 87: 115–122).

Alternatively, the transgenic genotype of the regenerated shoot may be verified by performing NPTII assays (Radke, S. E. et al, Theor. Appl. Genet. (1988), 75: 685–694) or by performing PCR analysis according to Wang et al (1993, NAR 21 pp 4153–4154).

The shoots (height approximately 2–3 cms) were transplanted from rooting substrate to soil and placed in a growth chamber (21° C., 16 hour light 200–400 uE/m²/sec).

When the plants were well established they were transferred to the greenhouse, where they were grown until tubers had developed and the upper part of the plants were senescing.

Harvesting

The potatoes were harvested after about 3–6 months and then analysed.

The transformed shoots can be distinguished from the non-transformed shoots by adding glucosamine to their substrate. After harvest of the shoots, the transformed shoots can be selected by adding high amounts of glucosamine to the shoot medium. The transformed shoots will have the ability to use glucosamine and will survive.

Analysis of Transformants

In order to confirm the integration of nagB, genomic DNA may be isolated by the method of Dellaporta et al (1983 Plant Mol Biol Rep 1 19–21) and samples of this DNA, digested with EcoRI subjected to electrophoresis in an 0.8% w/v agarose gel and transferred to Hybond N+ membranes (Amersham) by Southern blotting (Southern, 1975 J Mol Biol 98 503–517). Probes for the coding region of nagB may be used as templates for random primed synthesis of $^{32}$P-labelled probe after the method of Feinberg and Vogelstein (1983 Anal Bioch 137 266–267) and hybridised to the Southern blots at high stringency (65° C., 0.1×SSC).

The results using media comprising 7.5 g/l of sucrose are shown in the following Tables.

| Glucos-amine (g/l) | NH$_4$/NO$_3$ (g/l) | Number of transformed areas per explant | Number of transgenic shoots | Transformation frequency (%) (Number transgenic shoots/started explants) |
| --- | --- | --- | --- | --- |
| 2 | 1650 | 0 | 0 | 0 |
| 2 | 1298 | 0.025 | 0 | 0 |
| 2.5 | 1650 | 0 | 0 | 0 |
| 2.5 | 1189 | 0 | 0 | 0 |
| 3 | 1650 | 0 | 0 | 0 |
| 3 | 1093 | 0 | 0 | 0 |
| 0 | 1650 | 1.08 | 3 | 7.5 |
| 0 | 1298 | 2.73 | 6 | 15 |
| 0 | 1189 | 2.50 | 12 | 30 |
| 0 | 1093 | 1.40 | 12 | 30 |

| Glucosamine (g/l) | Number of transformed areas per explant | Number of transgenic shoots | Transformation frequency (number transgenic shoots/started explants) |
| --- | --- | --- | --- |
| 0 | 5.4 | 12 | 24 |
| 1 | 3.8 | 1 | 2 |
| 2.5 | 0 | 0 | 0 |
| 5 | 0 | 0 | 0 |
| 7.5 | 0 | 0 | 0 |
| 10 | 0 | 0 | 0 |

The results show that the nagB gene provides a selection system for the transformed potato cells.

In addition, subsequent studies showed that transformed potatoes may be exposed to a medium comprising glucosamine so as to ensure the selection thereof.

The results also show that in some instances lowering the content of NH$_4$NO$_3$ makes the glucosamine less toxic. However, when lowering the concentration of NH$_4$NO$_3$ the efficiency of the inserted genes in terms of transformation events goes up.

Transgenic Maize Plants

Introduction

Since the first publication of production of transgenic plants in 1983 (Leemans, 1993 Biotechnology 11 s22), there have been numerous publications of production of transgenic plants including especially dicotyledon crop plants.

Until very recently there were very few reports on successful production of transgenic monocotyledononary crop plants. This relatively slow development within monocots were due to two causes. Firstly, until the early 1980s, efficient regeneration of plants from cultured cells and tissues of monocots had proven very difficult. This problem was ultimately solved by the culture of explants from immature and embryogenic tissue, which retain their morphogenic potential on nutrient media containing plant growth regulators. Secondly, the monocots are not a natural host for *Agrobacterium tumefaciens,* meaning that the successful developed techniques within the dicots using their natural vector *Agrobacterium tumefaciens* was unsuccessful for many years in the monocots.

Nevertheless, it is now possible to successfully transformation and produce fertile transgenic plants of maize using methods such as: (1) Silicon Carbide Whiskers; (2) Particle Bombardment; (3) DNA Uptake by PEG treated protoplast; or (4) DNA Uptake in Electroporation of Tissue. Each of these methods—which are reviewed by Thompson (1995 Euphytica 85 pp 75–80)—may be used to prepare inter alia transgenic maize according to the present invention.

In particular, the particle Gun method has been successfully used for the transformation of monocots. However, EP-A-0604662 reports on a different method of transforming monocotyledons. The method comprises transforming cultured tissues of a monocotyledon under or after dedifferentiation with Agrobacterium containing a super binary vector as a selection means a hygromycin-resistant gene was used. Production of transgenic calli and plant was demonstrated using the hygromycin selection. This method may be used to prepare inter alia transgenic maize according to the present invention.

Subsequent to the method of EP-A-0604662, EP-A-0672752 reports on non-dedifferentiated immature embryos. In this regard, both hygromycin-resistance and PPT-resistance genes were used as the selection means, with PPT giving rise to 10% or more independent transformed plants. This method may be used to prepare inter alia transgenic maize according to the present invention.

To date, it would appear that transgenic maize plants can be successfully produced from easily-culturable varieties—such as the inbred fine A188. In this regard, see the teachings of Ishida et al (1996 Nature Biotechnology 14 pp 745–750). The method disclosed by these workers may be used to prepare inter alia transgenic maize according to the present invention.

Vasil (1996 Nature Biotechnology 14 pp 702–703) presents a further review article on transformation of maize.

Even though it is possible to prepare transformed maize by use of, for example, particle Gun mediated transformation, for the present studies the following protocol is adopted.

Plasmid Construction

The disarmed *Agrobacterium tumefaciens* strain LBA 4404, containing the helper vir plasmid pRAL4404 (Hoekema et al, 1983 Nature 303 pp 179–180), was cultured on YMB agar (K$_2$HPO$_4$.3H$_2$O 660 mg l$^{-1}$, MgSO$_4$ 200 mg l$^{-1}$, NaCl 100 mg l$^{-1}$, mannitol 10 g l$^{-1}$, yeast extract 400 mg l$^{-1}$, 0.8% w/v agar, pH 7.0) containing 100 mg l$^{-1}$ rifampicin and 500 mg l$^1$streptomycin sulphate. Transformation with pVICTOR IV GNG E35S nagB Iv2 or pVICTOR IV GNG rbc nagB IV2 or pVICTOR IV GNG E35S nagB was accomplished using the freeze-thaw method of Holters et al (1978 Mol Gen Genet 163 181–187) and transformants were selected on YMB agar containing 100 mg l$^{-1}$ rifampicin and 500 mg l$^{-1}$ streptomycin, and 50 mg l$^{-1}$ gentamycin sulphate. Transformation with a control construct lacking the nagB gene was performed in the same manner.

Isolation and Cocultivation of Explants

Immature embryos of, for example, maize line A188 of the size between 1.5 to 2.5 mm were isolated and cocultivated with *Agrobacterium tumefaciens* strain LBA 4404 in N6AS for 2–3 days at 25° C. under illumination. Thereafter, the embryos were washed with sterilized water containing 250 mg/l of cefotaxime and transferred to an LS medium and 250 mg/l cefotaxime and glucosamine in concentrations of up to 100 mg/l (the medium is hereafter called LSS1).

Conditions for the Selection of Transgenic Plants

The explants were cultured for three weeks on LSS1 medium and then transferred to an LS medium containing glucosamine and cefotaxime. After three weeks on this medium, green shoots were isolated and tested for Gus activity.

Rooting of Gus Positive Shoots

Gus positive shoots were transferred to an MS medium containing 2 mg/l for rooting. After four weeks on this medium, plantlets are transferred to pots with sterile soil for acclimatisation.

Discussion

In these studies the coding region of the gene coding for the enzyme glucosamine-6-phosphate deaminase has been cloned and inserted into a plant expression cassette. This gene provides a useful selection means for plant transformation, wherein the selection means is capable of enabling the selection of a transformed cell over a non-transformed cell. In this regard, expression of this enzyme in plants relieves inhibition of metabolism by exogenously supplied glucosamine, which can advantageously serve as both a carbohydrate and nitrogen source for the transformed cells. The glucosamine can even used as a supplement for decreased levels of sucrose and ammonium salts in the tissue culture medium. At present, it is believed that the selection system has the added benefit of being self-regulated. As well as acting as a substrate for hexokinase, the glucosainine rapidly saturates the pathway leading to glycoprotein synthesis, with a consequent build up of N-acetyl glucosamine 6-phosphate. This in turn activates the glucosamine-6-phosphate deaminase, the activity of which will drop when exogenous supply of glucosamine is removed.

Thus, glucosamine 6-phosphate deaminase provides a useful alternative selection means to those that are currently available, particularly as it can be supplied as a source of nitrogen, which is much more limiting to plant growth than carbon alone.

In addition, glucosamine 6-phosphate deaminase provides a further useful alternative selection means to those that are currently available as it can be supplied as a source of nitrogen and carbon.

As an aside, we have found that for some plant cells there is an interaction between the levels of sucrose and glucosamine. In this regard, our preliminary findings suggest that for some plant cells as the concentration of sucrose decreases so the glucosamine becomes even more toxic for non-transformed plants. This would mean that the ingredients of the medium could be chosen to provide even more advantageous selection conditions for the transformed cells and plants.

Summary

The present invention therefore relates to a selection method for selecting from a population of cells one or more selectable genetically transformed cells—as well as constructs, vector, plasmids, cells and organisms for use in that method, in addition to constructs, vector, plasmids, cells and organisms prepared by use of such a method. In the method, the population of cells comprises selectable genetically transformed cells and possible non-transformed cells. Each of the selectable genetically transformed cells comprises a first expressable nucleotide sequence and optionally a second expressable nucleotide sequence. In the method, a component or a metabolic derivative thereof when present in a low concentration in a medium is a nutrient for both the selectable genetically transformed cells and the non-transformed cells. In the method, the component or the metabolic derivative thereof when present in a high concentration in a medium is toxic to the non-transformed cells but not the selectable genetically transformed cells. The first nucleotide sequence codes for a gene product capable of converting the component or the metabolic derivative thereof when present in a high concentration in a medium to a nutrient for the selectable genetically transformed cells. The method comprises the step of introducing the population of cells to a medium comprising a high concentration of the component or the metabolic derivative thereof. In the method, the component or the metabolic derivative thereof is a source of both carbohydrate and nitrogen for the selectable genetically transformed cells. Alternatively, in the method if a portion of the component serves as a metabolic substrate and is metabolically converted to a derivatised substrate, then that derivatised substrate is capable of providing an allosteric effect on the gene product.

Other modifications of the present invention will be apparent to those skilled in the art.

What is claimed is:

1. A selection method for selecting genetically transformed plant cells from a population of plant cells, comprising:
   transforming a population of plant cells with an expressible nucleotide sequence having at least 75% identity to SEQ ID NO: 1 and which encodes an enzyme having glucosamine-6-phosphate deaminase activity that converts a component or a metabolic derivative thereof when present in a high concentration in a medium into a nutrient, thereby producing a population of genetically transformed and non-transformed cells;
   introducing said population of plant cells to a medium comprising said component or metabolic derivative thereof, wherein the component or the metabolic derivative thereof is present in said medium in a high concentration and is toxic to said non-transformed plant cells and is a source of both carbohydrate and nitrogen for the selectable, genetically transformed plant cells or if a portion of the component serves as a metabolic substrate and is metabolically converted to a derivatized substrate, then that derivatized substrate provides an allosteric effect on the gene product; and
   culturing said plant cells thereby selecting at least a portion of said transformed plant cells over said non-transformed plant cells; and, wherein said enzyme having glucosamine-6-phosphate deaminase activity converts glucosamine-6-phosphate to fructose-6-phosphate.

2. The selection method of claim 1, wherein the population of cells is further transformed with a second expressible nucleotide sequence.

3. The selection method of claim 1, wherein said medium comprises said high concentration at a concentration greater than about 3.0 g/l.

4. The selection method of claim 1, wherein said component or metabolic derivative comprises a chemical group selected from the group consisting of an amine group and a phosphate group.

5. The selection method of claim 4, wherein said component is glucosamine.

6. The selection method of claim 4, wherein said metabolic derivative is glucosamine-6-phosphate.

7. The selection method of claim 1, wherein the expressible nucleotide sequence comprises an intron.

8. The selection method of claim 1, wherein the enzyme glucosamine-6-phosphate deaminase has the amino acid sequence shown as SEQ ID No. 3 or a sequence having at least 75% identity to SEQ ID No. 3.

9. The selection method of claim 1, wherein the enzyme glucosamine-6-phosphate deaminase is encoded by either the nucleotide sequence shown as SEQ ID No. 1 or a sequence having at least 75% identity to SEQ ID No:1 or the nucleotide sequence shown as SEQ ID No. 2.

10. The selection method of claim 1, wherein the method is carried out in vitro.

11. A composition comprising a population of transformed and non-transformed plant cells, said transformed plant cells being transformed with an expressible nucleotide sequence having at least 75% identity to SEQ ID NO: 1 and which encodes an enzyme having glucosamine-6-phosphate deaminase activity which converts a component or a metabolic derivative thereof into a nutrient, and a medium comprising said component or metabolic derivative thereof, wherein the component or the metabolic derivative thereof is present in said medium in a high concentration and is toxic to said non-transformed plant cells; and, wherein said enzyme having glucosamine-6-phosphate deaminase activity converts glucosamine-6-phosphate to fructose-6-phosphate.

12. The composition of claim 11, wherein the medium comprises glucosamine or glucosamine-6-phosphate.

13. The composition of claim 11, wherein the enzyme glucosamine-6-phosphate deaminase has the amino acid sequence shown as SEQ ID No. 3 or a sequence having at least 75% identity to SEQ ID No. 3.

14. The composition of claim 11, wherein the expressible nucleotide sequence has either the nucleotide sequence shown as SEQ ID No. 1 or a sequence having at least 75% identity to SEQ ID No: 1 and encoding glucosamine-6-phosphate deaminase, or the nucleotide sequence shown as SEQ ID No. 2.

15. A construct for genetically transforming a non-transformed plant cell to produce a selectable genetically transformed plant cell, said construct comprising: a plant promoter operably linked to an expressible nucleotide sequence encoding a glucosamine-6-phosphate deaminase gene product and having at least 75% identity to SEQ ID NO: 1; and, wherein said glucosamine-6-phosphate deaminase gene product converts glucosamine-6-phosphate to fructose-6-phosphate.

16. The construct of claim 15, wherein the enzyme glucosamine-6-phosphate deaminase has the amino acid sequence shown as SEQ ID No. 3 or a sequence having at least 75% identity to SEQ ID No. 3.

17. The construct of claim 15, wherein the enzyme glucosamine-6-phosphate deaminase is encoded by either the nucleotide sequence shown as SEQ ID No. 1 or a sequence having at least 75% identity to SEQ ID No: 1 or the nucleotide sequence shown as SEQ ID No. 2.

18. A kit comprising the construct of claim 15 and a component which is either a substrate for the glucosamine-6-phosphate deaminase or is a metabolic precursor to such a substrate.

19. A transgenic plant produced from a cell transformed with an expressible nucleotide sequence having at least 75% identity to SEQ ID NO: 1 and encoding an enzyme having glucosamine-6-phosphate deaminase activity.

20. The plant of claim 19, wherein said plant is selected from the group consisting of gourd, potato and maize.

21. An *E. coli* strain selected from the group consisting of NCIMB 40852, NCIMB 40853, and NCIMB 40854.

22. An isolated or purified polynucleotide having a sequence which comprises SEQ ID No: 2.

23. The selection method of claim 9, wherein the sequence having at least 75% identity to SEQ ID NO: 1 further comprises an intron.

24. The composition of claim 14, wherein the sequence having at least 75% identity to SEQ ID NO: 1 further comprises an intron.

25. The construct of claim 17, wherein the sequence having at least 75% identity to SEQ ID NO: 1 further comprises an intron.

* * * * *

SEQUENCE LISTING

```
<160> NUMBER OF SEQ ID NOS:  23

<210> SEQ ID NO 1
<211> LENGTH: 834
<212> TYPE: DNA
<213> ORGANISM: Escherichia coli
<220> FEATURE:
<221> NAME/KEY: CDS
<222> LOCATION: (0)...(0)
<223> OTHER INFORMATION: Glucosamine-6-Phosphate Deaminase

<400> SEQUENCE: 1
gatctaaaca acaacatgag actgatcccc ctgactaccg ctgaacaggt cggcaaatgg      60
```

-continued

```
gctgctcgcc atatcgtcaa tcgtatcaat gcgttcaaac cgactgccga tcgtccgttt    120
gtactgggcc tgccgactgg cggcacgccg atgaccacct ataaagcgtt agtcgaaatg    180
cataaagcag gccaggtcag ctttaagcac gttgtcacct tcaacatgga cgaatatgtc    240
ggtctgccga agagcatccc ggaaagctac tacagcttta tgcaccgtaa tttcttcgat    300
cacgttgata ttccagcaga aaacatcaac cttctcaacg gcaacgcccc ggatatcgac    360
gccgagtgcc gccagtatga agaaaaaatc cgttcttacg gaaaaattca tctgtttatg    420
ggcggtgtag gtaacgacgg tcatattgca tttaacgaac cggcgtcttc tctggcttct    480
cgtactcgta tcaaaaccct gactcatgac actcgcgtcg caaactctcg tttctttgat    540
aacgatgtta atcaggtgcc aaaatatgcc ctgactgtcg tgttggtac actgctggat    600 gccgaagaag tgatgattct ggtgctgggt agccagaaag cactggcgct gcaggccgcc    660
gttgaaggtt gcgtgaacca tatgtggacc atcagctgtc tgcaactgca tccgaaagcg    720
atcatggtgt gcgatgaacc ttccaccatg gagctgaaag ttaagacttt aagatatttc    780
aatgaattag aagcagaaaa atatcaaggt ctgtaattgt tatccctgct cgag           834

<210> SEQ ID NO 2
<211> LENGTH: 1034
<212> TYPE: DNA
<213> ORGANISM: Escherichia coli
<220> FEATURE:
<221> NAME/KEY: CDS
<222> LOCATION: (0)...(0)
<223> OTHER INFORMATION: Glucosamine-6-Phosphate deaminase.

<400> SEQUENCE: 2
tgcagagatc taaacaacaa catgagactg atcccctga ctaccgctga acaggtcggc      60
aaatgggctg ctcgccatat cgtcaatcgt atcaatgcgt tcaaaccgac tgccgatcgt    120
ccgtttgtac tgggcctgcc gactggcggc acgccgatga ccacctataa agcgttagtc    180
gaaatgcata agcaggcca ggtcagcttt aagcacgttg tccacttcaa catggtaagt    240
ttctgcttct acctttgata tatataat aattatcatt aattagtagt aatataatat      300
ttcaaatatt tttttcaaaa taaagaatg tagtatatag caattgcttt tctgtagttt     360
ataagtgtgt atattttaat ttataacttt tctaatatat gaccaaaatt tgttgatgtg    420
caggacgaat atgtcggtct gccgaaagag catccggaaa gctactacag ctttatgcac    480
cgtaatttct tcgatcacgt tgatattcca gcagaaaaca tcaaccttct caacggcaac    540
gccccggata tcgacgccga gtgccgccag tatgaagaaa aaatccgttc ttacggaaaa    600
attcatctgt ttatgggcgg tgtaggtaac gacggtcata ttgcatttaa cgaaccggcg    660
tcttctctgg cttctcgtac tcgtatcaaa accctgactc atgacactcg cgtcgcaaac    720
tctcgtttct ttgataacga tgttaatcag gtgccaaaat atgccctgac tgtcgtgtt    780 ggtacactgc tggatgccga agaagtgatg attctggtgc tgggtagcca gaaagcactg    840
gcgctgcagg ccgccgttga aggttgcgtg aaccatatgt ggaccatcag ctgtctgcaa    900
ctgcatccga aagcgatcat ggtgtgcgat gaaccttcca ccatggagct gaaagttaag    960
actttaagat atttcaatga attagaagca gaaaatatca aggtctgta attgttatcc    1020 ctgctcgagg catg                                                      1034

<210> SEQ ID NO 3
<211> LENGTH: 266
<212> TYPE: PRT
```

-continued

```
<213> ORGANISM: Escherichia coli

<400> SEQUENCE: 3

Met Arg Leu Ile Pro Leu Thr Thr Ala Glu Gln Val Gly Lys Trp Ala
1               5                   10                  15

Ala Arg His Ile Val Asn Arg Ile Asn Ala Phe Lys Pro Thr Ala Asp
            20                  25                  30

Arg Pro Phe Val Leu Gly Leu Pro Thr Gly Thr Pro Met Thr Thr
        35                  40                  45

Tyr Lys Ala Leu Val Glu Met His Lys Ala Gly Gln Val Ser Phe Lys
    50                  55                  60

His Val Val Thr Phe Asn Met Asp Glu Tyr Val Gly Leu Pro Lys Glu
65                  70                  75                  80

His Pro Glu Ser Tyr Tyr Ser Phe Met His Arg Asn Phe Phe Asp His
                85                  90                  95

Val Asp Ile Pro Ala Glu Asn Ile Asn Leu Leu Asn Gly Asn Ala Pro
            100                 105                 110

Asp Ile Asp Ala Glu Cys Arg Gln Tyr Glu Glu Lys Ile Arg Ser Tyr
        115                 120                 125

Gly Lys Ile His Leu Phe Met Gly Gly Val Gly Asn Asp Gly His Ile
    130                 135                 140

Ala Phe Asn Glu Pro Ala Ser Ser Leu Ala Ser Arg Thr Arg Ile Lys
145                 150                 155                 160

Thr Leu Thr His Asp Thr Arg Val Ala Asn Ser Arg Phe Phe Asp Asn
                165                 170                 175

Asp Val Asn Gln Val Pro Lys Tyr Ala Leu Thr Val Gly Val Gly Thr
            180                 185                 190

Leu Leu Asp Ala Glu Glu Val Met Ile Leu Val Leu Gly Ser Gln Lys
        195                 200                 205

Ala Leu Ala Leu Gln Ala Ala Val Glu Gly Cys Val Asn His Met Trp
    210                 215                 220

Thr Ile Ser Cys Leu Gln Leu His Pro Lys Ala Ile Met Val Cys Asp
225                 230                 235                 240

Glu Pro Ser Thr Met Glu Leu Lys Val Lys Thr Leu Arg Tyr Phe Asn
                245                 250                 255

Glu Leu Glu Ala Glu Asn Ile Lys Gly Leu
            260                 265

<210> SEQ ID NO 4
<211> LENGTH: 9
<212> TYPE: PRT
<213> ORGANISM: Artificial Sequence
<220> FEATURE:
<223> OTHER INFORMATION: Conserved amino acid sequence of
      Glucosamine-6-Phosphate Deaminase.

<400> SEQUENCE: 4

Val Val Thr Phe Asn Met Asp Glu Tyr
1               5

<210> SEQ ID NO 5
<211> LENGTH: 248
<212> TYPE: PRT
<213> ORGANISM: Candida Albicans

<400> SEQUENCE: 5

Met Arg Gln Ala Ile Phe Ser Asn Pro Asn Asp Ala Ala Glu Tyr Leu
1               5                   10                  15
```

Ala Asn Tyr Ile Ile Ala Lys Ile Asn Ser Thr Pro Arg Thr Phe Val
            20                  25                  30

Leu Gly Leu Pro Thr Gly Ser Ser Pro Glu Gly Ile Tyr Ala Lys Leu
        35                  40                  45

Ile Glu Ala Asn Lys Gln Gly Arg Val Ser Phe Lys Asn Val Val Thr
50                  55                  60

Phe Asn Met Asp Glu Tyr Leu Gly Phe Ala Pro Ser Asp Leu Gln Ser
65                  70                  75                  80

Tyr His Tyr Phe Met Tyr Asp Lys Phe Asn His Ile Asp Ile Pro
                85                  90                  95

Arg Glu Asn Ile His Ile Leu Asn Gly Leu Ala Ala Asn Ile Asp Glu
            100                 105                 110

Glu Cys Ala Asn Tyr Glu Lys Lys Ile Lys Gln Tyr Gly Arg Ile Asp
            115                 120                 125

Leu Phe Leu Gly Gly Leu Gly Pro Glu Gly His Leu Ala Phe Asn Glu
130                 135                 140

Ala Gly Ser Ser Arg Asn Ser Lys Thr Arg Lys Val Glu Leu Val Glu
145                 150                 155                 160

Ser Thr Ile Lys Ala Asn Cys Arg Phe Phe Gly Asn Asp Glu Ser Lys
            165                 170                 175

Val Pro Lys Tyr Ala Leu Ser Val Gly Ile Ser Thr Ile Leu Asp Asn
            180                 185                 190

Ser Asp Glu Ile Ala Ile Ile Val Leu Gly Lys Ser Lys Gln Phe Ala
            195                 200                 205

Leu Asp Lys Thr Val Asn Gly Lys Pro Asn Asp Pro Lys Tyr Pro Ser
210                 215                 220

Ser Tyr Leu Gln Asp His Ala Asn Val Leu Ile Val Cys Asp Asn Ala
225                 230                 235                 240

Ala Ala Gly Leu Lys Ser Lys Leu
                245

<210> SEQ ID NO 6
<211> LENGTH: 38
<212> TYPE: DNA
<213> ORGANISM: Artificial Sequence
<220> FEATURE:
<223> OTHER INFORMATION: B134 primer.

<400> SEQUENCE: 6
taagatctaa acaacaacat gagactgatc cccctgac                    38

<210> SEQ ID NO 7
<211> LENGTH: 28
<212> TYPE: DNA
<213> ORGANISM: Artificial Sequence
<220> FEATURE:
<223> OTHER INFORMATION: B137 primer.

<400> SEQUENCE: 7
acctcgagca gggataacaa ttacagac                              28

<210> SEQ ID NO 8
<211> LENGTH: 29
<212> TYPE: DNA
<213> ORGANISM: Artificial Sequence
<220> FEATURE:
<223> OTHER INFORMATION: B507 primer.

<400> SEQUENCE: 8

```
tgcagagatc taaacaacaa catgagact                                      29

<210> SEQ ID NO 9
<211> LENGTH: 27
<212> TYPE: DNA
<213> ORGANISM: Artificial Sequence
<220> FEATURE:
<223> OTHER INFORMATION: B511 primer.

<400> SEQUENCE: 9
catgcctcga gcagggataa caattac                                        27

<210> SEQ ID NO 10
<211> LENGTH: 34
<212> TYPE: DNA
<213> ORGANISM: Artificial Sequence
<220> FEATURE:
<223> OTHER INFORMATION: B506 primer.

<400> SEQUENCE: 10
tagaagcaga aacttaccat gttgaaggtg acaa                                34

<210> SEQ ID NO 11
<211> LENGTH: 34
<212> TYPE: DNA
<213> ORGANISM: Artificial Sequence
<220> FEATURE:
<223> OTHER INFORMATION: B508 primer.

<400> SEQUENCE: 11
ttgtcacctt caacatggta agtttctgct tcta                                34

<210> SEQ ID NO 12
<211> LENGTH: 34
<212> TYPE: DNA
<213> ORGANISM: Artificial Sequence
<220> FEATURE:
<223> OTHER INFORMATION: B509 primer.

<400> SEQUENCE: 12
agaccgacat attcgtcctc cacatcaaca aatt                                34

<210> SEQ ID NO 13
<211> LENGTH: 34
<212> TYPE: DNA
<213> ORGANISM: Artificial Sequence
<220> FEATURE:
<223> OTHER INFORMATION: B510 primer.

<400> SEQUENCE: 13
aatttgttga tgtgcaggac gaatatgtcg gtct                                34

<210> SEQ ID NO 14
<211> LENGTH: 27
<212> TYPE: DNA
<213> ORGANISM: Artificial Sequence
<220> FEATURE:
<223> OTHER INFORMATION: B511 primer.

<400> SEQUENCE: 14
catgcctcga gcagggataa caattac                                        27

<210> SEQ ID NO 15
<211> LENGTH: 24
<212> TYPE: DNA
```

```
<213> ORGANISM: Artificial Sequence
<220> FEATURE:
<223> OTHER INFORMATION: Sequencing Primer, 5'fluorescein labelled.

<400> SEQUENCE: 15
cagcgttgta aaacgacggc cagt                                          24

<210> SEQ ID NO 16
<211> LENGTH: 17
<212> TYPE: DNA
<213> ORGANISM: Artificial Sequence
<220> FEATURE:
<223> OTHER INFORMATION: Sequencing Primer, 5'fluorescein labelled.

<400> SEQUENCE: 16
caggaaacag ctatgac                                                  17

<210> SEQ ID NO 17
<211> LENGTH: 17
<212> TYPE: DNA
<213> ORGANISM: Artificial Sequence
<220> FEATURE:
<223> OTHER INFORMATION: Primer which complements the nucleotide
      sequence of nagB.

<400> SEQUENCE: 17
gctttaagca cgttgtc                                                  17

<210> SEQ ID NO 18
<211> LENGTH: 17
<212> TYPE: DNA
<213> ORGANISM: Artificial Sequence
<220> FEATURE:
<223> OTHER INFORMATION: Primer which complements the nucleotide
      sequence of nagB (rev).

<400> SEQUENCE: 18
ggtgacaacg tgcttaa                                                  17

<210> SEQ ID NO 19
<211> LENGTH: 17
<212> TYPE: DNA
<213> ORGANISM: Artificial Sequence
<220> FEATURE:
<223> OTHER INFORMATION: Primer which complements the nucleotide
      sequence of nagB (rev).

<400> SEQUENCE: 19
tttgcgacgc gagtgtc                                                  17

<210> SEQ ID NO 20
<211> LENGTH: 17
<212> TYPE: DNA
<213> ORGANISM: Artificial Sequence
<220> FEATURE:
<223> OTHER INFORMATION: Primer which complements the nucleotide
      sequence of nagB (rev).

<400> SEQUENCE: 20
tattcgtcct gcacatc                                                  17

<210> SEQ ID NO 21
<211> LENGTH: 28
<212> TYPE: DNA
<213> ORGANISM: Artificial Sequence
<220> FEATURE:
<223> OTHER INFORMATION: Consensus sequence for plant introns.
```

```
<221> NAME/KEY: misc_feature
<222> LOCATION: (1)...(28)
<223> OTHER INFORMATION: n = A,T,C or G

<400> SEQUENCE: 21
mwggtangtt tnntttttt tttnyagg                                    28

<210> SEQ ID NO 22
<211> LENGTH: 24
<212> TYPE: DNA
<213> ORGANISM: Artificial Sequence
<220> FEATURE:
<223> OTHER INFORMATION: DNA sequence of nagB consensus region.

<400> SEQUENCE: 22
gtcaccttca acatggacga atat                                       24

<210> SEQ ID NO 23
<211> LENGTH: 45
<212> TYPE: DNA
<213> ORGANISM: Artificial Sequence
<220> FEATURE:
<223> OTHER INFORMATION: DNA sequence of splice sites of IV2 intron in
      nagB.

<400> SEQUENCE: 23
gtcaccttca acatggtaag ttttgttgat gtgcaggacg aatat                45
```